(12) United States Patent
Basarab et al.

(10) Patent No.: US 7,674,801 B2
(45) Date of Patent: Mar. 9, 2010

(54) ALKYL UREA SUBSTITUTED PYRIDINES

(75) Inventors: Gregory Steven Basarab, Waltham, MA (US); Shanta Bist, Waltham, MA (US); John Irvin Manchester, Waltham, MA (US); Brian Sherer, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/950,105

(22) Filed: Dec. 4, 2007

(65) Prior Publication Data

US 2008/0132546 A1    Jun. 5, 2008

Related U.S. Application Data

(60) Provisional application No. 60/868,501, filed on Dec. 4, 2006.

(51) Int. Cl.
   *C07D 471/04*    (2006.01)
(52) U.S. Cl. .............. 514/300; 514/312; 514/334; 514/335; 514/336; 546/121; 546/154; 546/256; 546/257; 546/261; 546/270.1; 546/270.4
(58) Field of Classification Search .......... 546/121, 546/256
   See application file for complete search history.

(56) References Cited

FOREIGN PATENT DOCUMENTS

| WO | WO/2005090328 | * | 9/2005 |
|----|---------------|---|--------|
| WO | 2006/038116 A2 | | 4/2006 |
| WO | 2007/107758 A1 | | 9/2007 |
| WO | 2007/148093 A1 | | 12/2007 |

OTHER PUBLICATIONS

Kelly et al. Total Synthesis of Dimethyl Sulfomycinamate. 1996, Journal of Organic Chemistry, 61, 4623-4633.*
Charifson, Paul, S., et al., Novel Dual-Targeting Benzimidazole Urea Inhibitors of DNA Gyrase and Topoisomerase IV Possessing Potent Antibacterial Activity: Intelligent Design and Evolution through the Judicious Use of Structure-Guided Design and Structure-Activity Relationships, J. Med. Chem., 2008, pp. 5243-5263, vol. 51(17).

* cited by examiner

*Primary Examiner*—James O Wilson
*Assistant Examiner*—Brian McDowell

(57) ABSTRACT

Compounds of formula (I) and their pharmaceutically acceptable salts are described. Processes for their preparation, pharmaceutical compositions containing them, their use as medicaments and their use in the treatment of bacterial infections are also described.

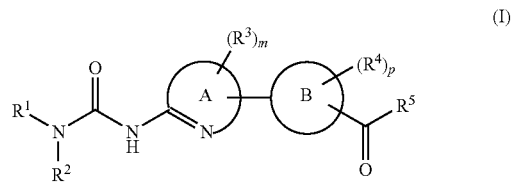

17 Claims, No Drawings

ALKYL UREA SUBSTITUTED PYRIDINES

RELATED APPLICATIONS

This application claims the benefit of U.S. provisional application No. 60/868,501, filed on Dec. 4, 2006, the entire teachings of which are incorporated herein by reference.

The present invention relates to compounds which demonstrate antibacterial activity, processes for their preparation, pharmaceutical compositions containing them as the active ingredient, to their use as medicaments and to their use in the manufacture of medicaments for use in the treatment of bacterial infections in warm-blooded animals such as humans. In particular this invention relates to compounds useful for the treatment of bacterial infections in warm-blooded animals such as humans, more particularly to the use of these compounds in the manufacture of medicaments for use in the treatment of bacterial infections in warm-blooded animals such as humans.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded as effective against both Gram-positive and certain Gram-negative pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant *staphylococcus aureus* (MRSA), methicillin resistant coagulase negative staphylococci (MRCNS), penicillin resistant *Streptococcus pneumoniae* and multiple resistant *Enterococcus faecium*.

The preferred clinically effective antibiotic for treatment of last resort of such resistant Gram-positive pathogens is vancomycin. Vancomycin is a glycopeptide and is associated with various toxicities, including nephrotoxicity. Furthermore, and most importantly, antibacterial resistance to vancomycin and other glycopeptides is also appearing. This resistance is increasing at a steady rate rendering these agents less and less effective in the treatment of Gram-positive pathogens. There is also now increasing resistance appearing towards agents such as β-lactams, quinolones and macrolides used for the treatment of upper respiratory tract infections, also caused by certain Gram negative strains including *H. influenzae* and *M. catarrhalis*.

Consequently, in order to overcome the threat of widespread multi-drug resistant organisms, there is an on-going need to develop new antibiotics, particularly those with either a novel mechanism of action and/or containing new pharmacophoric groups.

Deoxyribonucleic acid (DNA) gyrase is a member of the type II family of topoisomerases that control the topological state of DNA in cells (Champoux, J. J.; 2001. Ann. Rev. Biochem. 70: 369-413). Type II topoisomerases use the free energy from adenosine triphosphate (ATP) hydrolysis to alter the topology of DNA by introducing transient double-stranded breaks in the DNA, catalyzing strand passage through the break and resealing the DNA. DNA gyrase is an essential and conserved enzyme in bacteria and is unique among topoisomerases in its ability to introduce negative supercoils into DNA. The enzyme consists of two subunits, encoded by gyrA and gyrB, forming an $A_2B_2$ tetrameric complex. The A subunit of gyrase (GyrA) is involved in DNA breakage and resealing and contains a conserved tyrosine residue that forms the transient covalent link to DNA during strand passage. The B subunit (GyrB) catalyzes the hydrolysis of ATP and interacts with the A subunit to translate the free energy from hydrolysis to the conformational change in the enzyme that enables strand-passage and DNA resealing.

Another conserved and essential type II topoisomerase in bacteria, called topoisomerase IV, is primarily responsible for separating the linked closed circular bacterial chromosomes produced in replication. This enzyme is closely related to DNA gyrase and has a similar tetrameric structure formed from subunits homologous to Gyr A and to Gyr B. The overall sequence identity between gyrase and topoisomerase IV in different bacterial species is high. Therefore, compounds that target bacterial type II topoisomerases have the potential to inhibit two targets in cells, DNA gyrase and topoisomerase IV; as is the case for existing quinolone antibacterials (Maxwell, A. 1997, Trends Microbiol. 5: 102-109).

DNA gyrase is a well-validated target of antibacterials, including the quinolones and the coumarins. The quinolones (e.g. ciprofloxacin) are broad-spectrum antibacterials that inhibit the DNA breakage and reunion activity of the enzyme and trap the GyrA subunit covalently complexed with DNA (Drlica, K., and X. Zhao, 1997, Microbiol. Molec. Biol. Rev. 61: 377-392). Members of this class of antibacterials also inhibit topoisomerase IV and as a result, the primary target of these compounds varies among species. Although the quinolones are successful antibacterials, resistance generated primarily by mutations in the target (DNA gyrase and topoisomerase IV) is becoming an increasing problem in several organisms, including *S. aureus* and *Streptococcus pneumoniae* (Hooper, D. C., 2002, The Lancet Infectious Diseases 2: 530-538). In addition, quinolones, as a chemical class, suffer from toxic side effects, including arthropathy that prevents their use in children (Lipsky, B. A. and Baker, C. A., 1999, Clin. Infect. Dis. 28: 352-364). Furthermore, the potential for cardiotoxicity, as predicted by prolongation of the $QT_c$ interval, has been cited as a toxicity concern for quinolones.

There are several known natural product inhibitors of DNA gyrase that compete with ATP for binding the GyrB subunit (Maxwell, A. and Lawson, D. M. 2003, Curr. Topics in Med. Chem. 3: 283-303). The coumarins are natural products isolated from *Streptomyces* spp., examples of which are novobiocin, chlorobiocin and coumermycin A1. Although these compounds are potent inhibitors of DNA gyrase, their therapeutic utility is limited due to toxicity in eukaryotes and poor penetration in Gram-negative bacteria (Maxwell, A. 1997, Trends Microbiol. 5: 102-109). Another natural product class of compounds that targets the GyrB subunit is the cyclothialidines, which are isolated from *Streptomyces filipensis* (Watanabe, J. et al 1994, J. *Antibiot.* 47: 32-36). Despite potent activity against DNA gyrase, cyclothialidine is a poor antibacterial agent showing activity only against some eubacterial species (Nakada, N, 1993, *Antimicrob. Agents Chemother.* 37: 2656-2661).

Synthetic inhibitors that target the B subunit of DNA gyrase and topoisomeraseIV are known in the art. For example, coumarin-containing compounds are described in patent application number WO 99/35155, 5,6-bicyclic heteroaromatic compounds are described in patent application WO 02/060879, and pyrazole compounds are described in patent application WO 01/52845 (U.S. Pat. No. 6,608,087). AstraZeneca has also published certain applications describing anti-bacterial compounds: WO2005/026149, WO2006/

087544, WO2006/087548, WO2006/087543, WO2006/092599 and WO2006/092608.

We have discovered a new class of compounds which are useful for inhibiting DNA gyrase and/or topoisomerase IV.

According to the present invention there is provided a compound of formula (I):

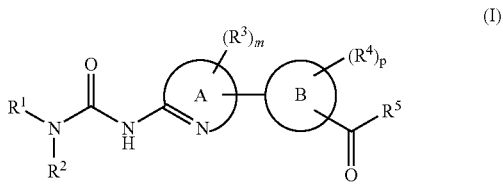

wherein:

$R^1$ is selected from $C_{1-6}$alkyl, $C_{2-6}$alkenyl, $C_{2-6}$alkynyl or $C_{3-6}$cycloalkyl; wherein $R^1$ may be optionally substituted on carbon by one or more $R^6$;

$R^2$ is selected from hydrogen or $C_{1-6}$alkyl; wherein said $C_{1-6}$alkyl may be optionally substituted by one or more groups independently selected from halo, cyano, hydroxy, nitro and amino;

or $R^1$ and $R^2$ together with the nitrogen to which they are attached form a heterocyclic ring; wherein said heterocyclic ring may be optionally substituted on carbon by one or more $R^7$; and wherein if said heterocyclic ring contains an —NH— moiety that nitrogen may be optionally substituted by a group selected from $R^8$;

$R^3$ and $R^4$ are substituents on carbon and are each independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, N—($C_{1-6}$alkoxy)carbamoyl, N,N—($C_{1-6}$alkoxy)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, carbocyclyl-$R^9$— or heterocyclyl-$R^{10}$—; wherein $R^3$ and $R^4$ independently of each other may be optionally substituted on carbon by one or more $R^{11}$; and wherein if said heterocyclyl contains an —NH— moiety that nitrogen may be optionally substituted by a group selected from $R^{12}$ m is 0, 1, or 2; wherein the values of $R^3$ may be the same or different;

p is 0, 1, or 2; wherein the values of $R^4$ may be the same or different;

Ring A is a nitrogen containing 5 or 6 membered heterocyclic group; wherein the nitrogen drawn is =N— and is ortho to the $R^1R^2NC(O)NH$ group of formula (I); and wherein if said heterocyclic group contains an —NH— moiety that nitrogen may be optionally substituted by a group selected from $R^{13}$;

Ring B is carbocyclyl or heterocyclyl; wherein if said heterocyclyl contains an —NH— moiety that nitrogen may be optionally substituted by a group selected from $R^{14}$;

$R^5$ is selected from hydroxy, $C_{1-6}$alkoxy, —N($R^{15}$)($R^{16}$) and a nitrogen linked heterocyclyl; wherein said $C_{1-6}$alkoxy may be optionally substituted on carbon by one or more $R^{17}$; and wherein if said nitrogen linked heterocyclyl contains an —NH— moiety that nitrogen may be optionally substituted by a group selected from $R^{18}$;

$R^6$, $R^7$, $R^{11}$ and $R^{17}$ are substituents on carbon and are each independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^6$, $R^7$, $R^{11}$ and $R^{17}$ independently of each other may be optionally substituted on carbon by one or more $R^{19}$; and wherein if said heterocyclyl contains an —NH— moiety that nitrogen may be optionally substituted by a group selected from $R^{20}$;

$R^{15}$ and $R^{16}$ are independently selected from hydrogen, $C_{1-6}$alkyl, $C_{1-6}$alkoxy, $C_{1-6}$alkanoyl, carbocyclyl or heterocyclyl; wherein $R^{15}$ and $R^{16}$ independently of each other may be optionally substituted on carbon by one or more $R^{21}$; and wherein if said heterocyclyl contains an —NH— moiety that nitrogen may be optionally substituted by a group selected from $R^{22}$;

$R^8$, $R^{12}$, $R^{13}$, $R^{14}$, $R^{18}$, $R^{20}$ and $R^{22}$ are independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^8$, $R^{12}$, $R^{13}$, $R^{14}$, $R^{18}$, $R^{20}$ and $R^{22}$ independently of each other may be optionally substituted on carbon by one or more $R^{23}$;

$R^9$ and $R^{10}$ are independent selected from a direct bond, —O—, —N($R^{24}$)—, —C(O)—, —N($R^{25}$)C(O)—, —C(O)N($R^{26}$)—, —S(O)$_s$—, —SO$_2$N($R^{27}$)— or —N($R^{28}$)SO$_2$—; wherein $R^{24}$, $R^{25}$, $R^{26}$, $R^{27}$ and $R^{28}$ are independently selected from hydrogen or $C_{1-6}$alkyl and s is 0-2; and $R^{19}$, $R^{21}$ and $R^{23}$ are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof;

with the proviso that said compound is not (i) 5-[2-[[(ethylamino)carbonyl]amino]pyridin-4-yl]-4-methyl-4H-1,2,4-triazole-3-carboxylic acid ethyl ester or (ii) benzoic acid, 4-[2-[[(4-methyl-1-piperazinyl)carbonyl]amino]-4-thiazolyl]-, methyl ester.

In some embodiments, compounds of formula (I), or pharmaceutically acceptable salts thereof, the following provisos also apply:

a) the compounds do not include (iii) 4-((4E)-4-{[5-(dimethylamino)-2-thienyl]methylene}-3-{[(methylamino)carbonyl]amino}-5-oxo-4,5-dihydro-1H-pyrazol-1-yl)benzoic acid; or (iv) 5-((4E)-4-{[5-(diethylamino)-2-furyl]methylene}-3-{[(methylamino)carbonyl]amino}-5-oxo-4,5-dihydro-1H-pyrazol-1-yl)isophthalic acid; and/or b) when ring A is a thiazolyl, $R^1$ is not a $C_{1-6}$alkyl which is substituted with an optionally substituted heterocycle or an optionally substituted N—($C_{1-6}$alkyl)carbamoyl; and/or c) when ring A is a thiazolyl, $R^5$ is not morpholino.

In this specification the term alkyl includes both straight and branched chain alkyl groups. For example, "$C_{1-6}$alkyl" includes methyl, ethyl, propyl, isopropyl and t-butyl. However references to individual alkyl groups such as propyl are specific for the straight chain version only. An analogous convention applies to other generic terms.

As used herein, the term "$C_{1-6}$haloalkyl" refers to an alkyl group that has from 1 to 6 carbon atoms in which one or more of the carbon atoms are substituted with a halo group. Representative haloalkyl groups include —$CF_3$, —$CHF_2$, —$CCl_3$, —$CH_2CH_2Br$, —$CH_2CH(CH_2CH_2Br)CH_3$, —$CHICH_3$, and the like.

As used herein, the term "halo" refers to fluoro, chloro, bromo, and iodo.

Where optional substituents are chosen from one or more groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a —$CH_2$— group can optionally be replaced by a —C(O)— and a ring sulphur atom may be optionally oxidised to form the S-oxide(s). In one aspect of the invention a "heterocyclyl" is a saturated, partially saturated or unsaturated, monocyclic ring containing 5 or 6 atoms of which at least one atom is chosen from nitrogen, sulphur or oxygen, it may, unless otherwise specified, be carbon or nitrogen linked, a —$CH_2$— group can optionally be replaced by a —C(O)— and a ring sulphur atom may be optionally oxidised to form the S-oxides. In a further aspect of the invention a "heterocyclyl" is an unsaturated, carbon-linked, monocyclic ring containing 5 or 6 atoms of which at least one atom is chosen from nitrogen, sulphur or oxygen. Examples and suitable values of the term "heterocyclyl" are morpholino, piperidyl, pyridyl, pyranyl, pyrrolyl, pyrazolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, quinolin-4(1H)-one, pyridin-2(1H)-one, imidazo[1,2-a]pyridinyl, 1-isoquinolone, 2-pyrrolidone, 4-thiazolidone, pyridine-N-oxide and quinoline-N-oxide. Further examples and suitable values of the term "heterocyclyl" are thiazolyl, quinolinyl, benzothiazolyl, pyrimidinyl and pyridyl. Suitable examples of "a nitrogen linked heterocyclyl" are morpholino, piperazin-1-yl, piperidin-1-yl and imidazol-1-yl.

"$R^1$ and $R^2$ together with the nitrogen to which they are attached form a heterocyclic ring" said heterocyclic ring is a saturated, partially saturated or unsaturated, mono or bicyclic ring containing 4-12 atoms of which one atom is the nitrogen linked to the —C(O)NH— of formula (I), (XIV), (XV), (XVI), or (XVII) and the other atoms are selected from carbon, nitrogen, sulphur or oxygen, wherein a —$CH_2$— group can optionally be replaced by a —C(O)— and a ring sulphur atom may be optionally oxidised to form the S-oxide(s). Suitable examples of this "heterocyclic ring" are morpholino, piperazin-1-yl, piperidin-1-yl and imidazol-1-yl.

A "carbocyclyl" is a saturated, partially saturated or unsaturated, mono or bicyclic carbon ring that contains 3-12 atoms; wherein a —$CH_2$— group can optionally be replaced by a —C(O)—. Particularly "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. A particular example of "carbocyclyl" is phenyl.

Ring A is a "nitrogen containing 5 or 6 membered heterocyclic group; wherein the nitrogen drawn is =N— and is ortho to the $R^1R^2$NC(O)NH group of formula (I)". Said "heterocyclic group" is a partially saturated or unsaturated, monocyclic ring containing 5 or 6 atoms of which at least one atom is the nitrogen drawn in formula (I) and the others are chosen from carbon, nitrogen, sulphur or oxygen, which may, unless otherwise specified, be carbon or nitrogen linked, wherein a —$CH_2$— group can optionally be replaced by a —C(O)— and a ring sulphur atom may be optionally oxidised to form the S-oxide(s). The nitrogen drawn in formula (I) is connected by a double bond to the $R^1R^2$NC(O)NH group and has and a single bond on its other side. Suitable examples of this ring are pyridyl, thiazolyl, oxazolyl, pyrazolyl, imidazolyl, pyrrolyl, pyrimidinyl, pyridazinyl and pyrazinyl. If further clarification is required Ring A as a thiazole or pyridyl would be in the following orientation:

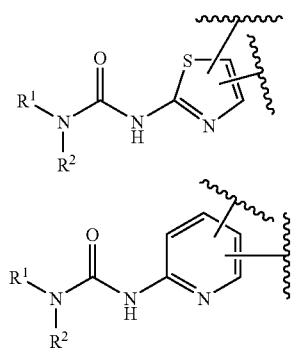

An example of "$C_{1-6}$alkanoyloxy" is acetoxy. Examples of "$C_{1-6}$alkoxycarbonyl" are methoxycarbonyl, ethoxycarbonyl, n- and t-butoxycarbonyl. Examples of "$C_{1-6}$alkoxycarbonylamino" are methoxycarbonylamino, ethoxycarbonylamino, n- and t-butoxycarbonylamino. Examples of "$C_{1-6}$alkoxy" are methoxy, ethoxy and propoxy. Examples of "$C_{1-6}$alkanoylamino" are formamido, acetamido and propionylamino. Examples of "$C_{1-6}$alkylS(O)$_a$ wherein a is 0 to 2" are methylthio, ethylthio, methylsulphinyl, ethylsulphinyl, mesyl and ethylsulphonyl. Examples of "$C_{1-6}$alkanoyl" are propionyl and acetyl. Examples of "N—($C_{1-6}$alkyl)amino" are methylamino and ethylamino. Examples of "N,N—($C_{1-6}$alkyl)$_2$amino" are di-N-methylamino, di-(N-ethyl)amino and N-ethyl-N-methylamino. Examples of "$C_{2-4}$alkenyl" are vinyl, allyl and 1-propenyl. Examples of "$C_{2-4}$alkynyl" are ethynyl, 1-propynyl and 2-propynyl. Examples of "N—($C_{1-6}$alkyl)sulphamoyl" are N-(methyl)sulphamoyl and N-(ethyl)sulphamoyl. Examples of "N,N—($C_{1-6}$alkyl)$_2$sulphamoyl" are N,N-(dimethyl)sulphamoyl and N-(methyl)-N-(ethyl)sulphamoyl. Examples of "N—($C_{1-6}$alkyl)carbamoyl" are methylaminocarbonyl and ethylaminocarbonyl. Examples of "N,N—($C_{1-6}$alkyl)$_2$carbamoyl" are dimethylaminocarbonyl and methylethylaminocarbonyl. Examples of "N—($C_{1-6}$alkoxy)carbamoyl" are methoxyaminocarbonyl and isopropoxyaminocarbonyl. Examples of "N—($C_{1-6}$alkyl)-N—($C_{1-6}$alkoxy)carbamoyl" are N-methyl-N-methoxyaminocarbonyl and N-methyl-N-ethoxyaminocarbonyl. Examples of "$C_{3-6}$cycloalkyl" are cyclopropyl, cyclobutyl, cyclopropyl and cyclohexyl.

Examples of "N'—(C$_{1-6}$alkyl)ureido" are N'-methylureido and N'-isopropylureido. Examples of "N',N'—(C$_{1-6}$alkyl)$_2$ureido" are N'N'-dimethylureido and N'-methyl-N'-isopropylureido. Examples of "N'—(C$_{1-6}$alkyl)hydrazinocarbonyl" are N'-methylhydrazinocarbonyl and N'-isopropylhydrazinocarbonyl. Examples of "N',N'—(C$_{1-6}$alkyl)$_2$hydrazinocarbonyl" are N'N'-dimethylhydrazinocarbonyl and N'-methyl-N'-isopropylhydrazinocarbonyl. Examples of "C$_{1-6}$ alkylsulphonylamino" are methylsulphonylamino, isopropylsulphonylamino and t-butylsulphonylamino. Examples of "C$_{1-6}$alkylsulphonylaminocarbonyl" are methylsulphonylaminocarbonyl, isopropylsulphonylaminocarbonyl and t-butylsulphonylaminocarbonyl. Examples of "C$_{1-6}$ lkylsulphonyl" are methylsulphonyl, isopropylsulphonyl and t-butylsulphonyl. Examples of "C$_{3-6}$cycloalkyl" are cyclopropyl and cyclohexyl.

A compound of formula (I), (XIV), (XV), (XVI), (XVII), (XVIII), (XIX), or (XX), may form stable acid or basic salts, and in such cases administration of a compound as a salt may be appropriate, and pharmaceutically acceptable salts may be made by conventional methods such as those described following.

Suitable pharmaceutically-acceptable salts include acid addition salts such as methanesulfonate, tosylate, α-glycerophosphate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

Within the present invention it is to be understood that a compound of the formula (I), (XIV), (XV), (XVI), (XVII), (XVIII), (XIX), or (XX), or a salt thereof may exhibit the phenomenon of tautomerism and that the formulae drawings within this specification can represent only one of the possible tautomeric forms. It is to be understood that the invention encompasses any tautomeric form which inhibits DNA gyrase and/or topoisomerase IV and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein. The same applies to compound names.

It will be appreciated by those skilled in the art that certain compounds of formula (I), (XIV), (XV), (XVI), (XVII), (XVIII), (XIX), or (XX), contain an asymmetrically substituted carbon and/or sulphur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the inhibition of DNA gyrase and/or topoisomerase IV, it being well known in the art how to prepare optically-active forms (for example, by resolution of the racemic form by recrystallization techniques, by synthesis from optically-active starting materials, by chiral synthesis, by enzymatic resolution, by biotransformation, or by chromatographic separation using a chiral stationary phase) and how to determine efficacy for the inhibition of DNA gyrase and/or topoisomerase IV by the standard tests described hereinafter.

It is also to be understood that certain compounds of the formula (I), (XIV), (XV), (XVI), (XVII), (XVIII), (XIX), or (XX), and salts thereof can exist in solvated as well as unsolvated forms such as, for example, hydrated forms. It is to be understood that the invention encompasses all such solvated forms which inhibit DNA gyrase and/or topoisomerase IV.

There follow particular and suitable values for certain substituents and groups referred to in this specification. These values may be used where appropriate with any of the definitions and embodiments disclosed hereinbefore, or hereinafter. For the avoidance of doubt each stated species represents a particular and independent aspect of this invention.

In one embodiment of the compounds represented by formula (I), Ring A is selected from the group consisting of pyridyl, pyrimidinyl, and thiazolyl.

In another embodiment of the compounds represented by formula (I), the compounds of the invention are represented by formula (XIV):

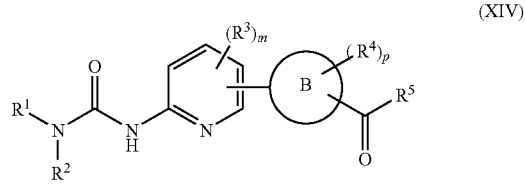

(XIV)

or a pharmaceutically acceptable salt thereof, wherein $R^1$, $R^2$, $R^3$, $R^4$, $R^5$, Ring B, m and p are defined as for formula (I).

In another embodiment of the compounds represented by formula (I), the compounds of the invention are represented by formula (XV):

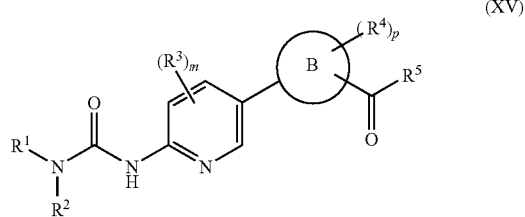

(XV)

or a pharmaceutically acceptable salt thereof, wherein $R^1$, $R^2$, $R^3$, $R^4$, $R^5$, Ring B, m and p are defined as for formula (I).

In another embodiment of the compounds represented by formula (I), the compounds of the invention are represented by formula (XVI):

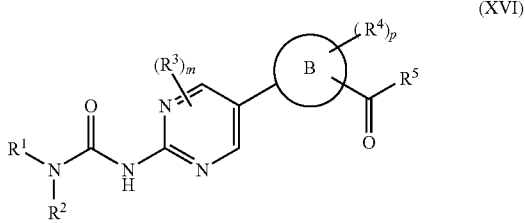

(XVI)

or a pharmaceutically acceptable salt thereof, wherein $R^1$, $R^2$, $R^3$, $R^4$, $R^5$, Ring B, m and p are defined as for formula (I).

In another embodiment of the compounds represented by formula (I), the compounds of the invention are represented by formula (XVII):

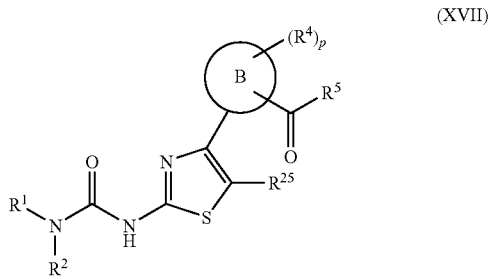

(XVII)

or a pharmaceutically acceptable salt thereof, wherein $R^{25}$ is H or $R^3$; and $R^1$, $R^2$, $R^3$, $R^4$, $R^5$, Ring B, and p are defined as for formula (I).

In one embodiment of the compounds represented by formula (I), (XVI), (XV), (XVI) or (XVII), Ring B is selected from the group consisting of thiazolyl, pyridinyl, 1,3-benzothiazolyl, phenyl, imidazo[1,2-a]pyridinyl, 4-oxo-1H-quinolinyl, and 2-oxo-1H-pyridinyl.

In another embodiment of the compounds represented by formula (I), (XVI), (XV), or (XVI), m is 0.

In another embodiment of the compounds represented by formula (I), (XVI), (XV), or (XVI), m is 1.

In another embodiment of the compounds represented by formula (I), (XVI), (XV), or (XVI), m is 2.

In another embodiment of the compounds represented by formula (I), (XVI), (XV), (XVI) or (XVII), $R^3$, for each occurrence, is independently selected from the group consisting of pyridinyl, phenyl, and thiazolyl, wherein the pyridinyl, phenyl or thiazolyl may be optionally substituted on one or more carbon atoms with one or more $R^{11}$.

In another embodiment of the compounds represented by formula (I), (XVI), (XV), (XVI) or (XVII), $R^{11}$, for each occurrence, is independently selected from the group consisting of a halo, a $C_{1-4}$alkyl, and a $C_{1-4}$haloalkyl.

In another embodiment of the compounds represented by formula (I), (XVI), (XV), (XVI) or (XVII), p is 0.

In another embodiment of the compounds represented by formula (I), (XVI), (XV), (XVI) or (XVII), p is 1.

In another embodiment of the compounds represented by formula (I), (XVI), (XV), (XVI) or (XVII), p is 2.

In another embodiment of the compounds represented by formula (I), (XVI), (XV), (XVI) or (XVII), $R^4$, for each occurrence, is independently selected from the group consisting of carbamoyl, an N—($C_{1-6}$alkyl)carbamoyl, an N,N—($C_{1-6}$alkyl)carbamoyl, a $C_{1-6}$alkoxycarbonyl, carboxy, oxo, hydroxy, a $C_{1-6}$alkyl, a $C_{1-6}$alkanoyl, a N—($C_{1-6}$alkoxy)carbamoyl, an imidazolyl, and a 1H-1,2,4-triazolyl, wherein the N—($C_{1-6}$alkyl)carbamoyl, N,N—($C_{1-6}$alkyl)carbamoyl, $C_{1-6}$alkoxycarbonyl, $C_{1-6}$alkyl, $C_{1-6}$alkanoyl, N—($C_{1-6}$alkoxy)carbamoyl, imidazolyl, and 1H-1,2,4-triazolyl may be optionally substituted on one or more carbon atoms with one or more $R^{11}$; and wherein the hydrogen of the —NH— of the imidazoyly and 1H-1,2,4-triazolyl optionally may be replaced with $R^{12}$.

In another embodiment of the compounds represented by formula (I), (XVI), (XV), (XVI) or (XVII), $R^{11}$, for each occurrence, is independently selected from the group consisting of a $C_{1-4}$alkyl, a $C_{1-4}$alkoxy, and a $C_{1-4}$alkoxy$C_{1-4}$alkyl; and $R^{12}$, for each occurrence is independently selected from the group consisting of $C_{1-4}$alkyl and a $C_{1-4}$alkoxy$C_{1-4}$alkyl.

In another embodiment of the compounds represented by formula (I), the compounds of the invention are represented by formula (XVIII):

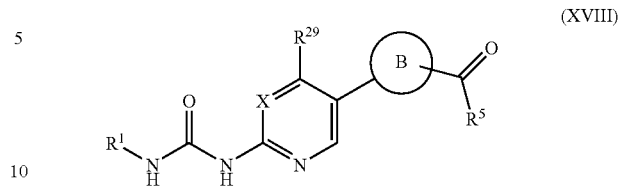

(XVIII)

or a pharmaceutically acceptable salt thereof, wherein:

X is CH or N; and $R^{29}$ is a 6-membered aryl or a 5- or 6-membered heteroaryl, wherein the aryl or heteroaryl is optionally substituted on one or more carbon atom with one or more $R^{11}$; and wherein if the heteroaryl comprises a —NH— moiety the hydrogen may be optionally substituted with a group selected from $R^8$.

In one embodiment of the compounds represented by formula (XVIII), Ring B is selected from the group consisting of phenyl, pyridinyl, and thiazolyl.

In another embodiment of the compounds represented by formula (XVIII), $R^{29}$ is selected from the group consisting of pyridinyl, thiazolyl, and phenyl, wherein the pyridinyl, thiazolyl or phenyl may be optionally substituted on one or more carbon atom with one or more $R^{11}$.

In another embodiment of the compounds represented by formula (I), the compounds of the invention are represented by formula (XIX):

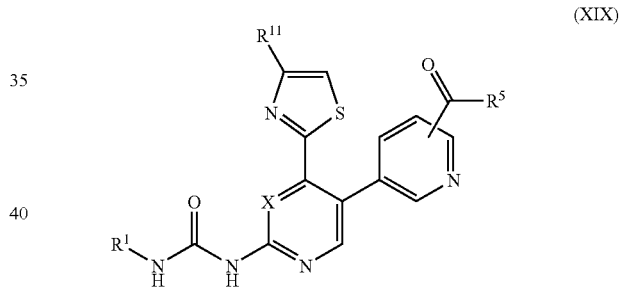

(XIX)

or a pharmaceutically acceptable salt thereof, wherein $R^1$, $R^5$, and $R^{11}$ are defined as for formula (I), and X is defined as in formula (XVIII).

In another embodiment of the compounds represented by formula (I), the compounds of the invention are represented by formula (XX):

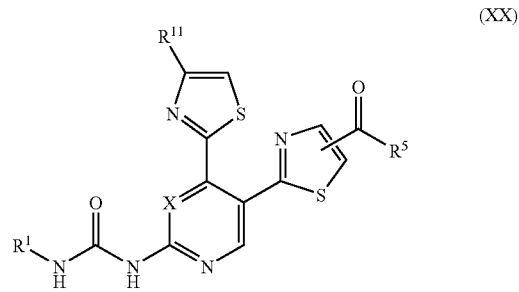

(XX)

or a pharmaceutically acceptable salt thereof, wherein $R^1$, $R^5$, and $R^{11}$ are defined as for formula (I), and X is defined as in formula (XVIII).

In another embodiment of the compounds represented by formula (I), (XVI), (XV), (XVI), (XVII), (XVIII), (XIX), or (XX), $R^{11}$ is a halo, a $C_{1-4}$alkyl, a $C_{1-4}$haloalkyl, or phenyl.

In another embodiment of the compounds represented by formula (I), (XVI), (XV), (XVI), (XVII), (XVIII), (XIX), or (XX), $R^1$ is $C_{1-6}$alkyl.

In another embodiment of the compounds represented by formula (I), (XVI), (XV), (XVI), (XVII), (XVIII), (XIX), or (XX), $R^1$ is ethyl.

In another embodiment of the compounds represented by formula (I), (XVI), (XV), (XVI), (XVII), (XVIII), (XIX), or (XX), $R^2$ is hydrogen.

In another embodiment of the compounds represented by formula (I), (XVI), (XV), or (XVI), m is 0.

In one embodiment of the compounds represented by formula (I), (XVI), (XV), (XVI), or (XVII), $R^4$ is a substituent on carbon and is selected from carboxy, carbamoyl, $C_{1-6}$alkanoyl, N—($C_{1-6}$alkyl)carbamoyl, N—($C_{1-6}$alkoxy)carbamoyl or $C_{1-6}$alkoxycarbonyl.

In another embodiment of the compounds represented by formula (I), (XVI), (XV), (XVI), or (XVII), $R^4$ is a substituent on carbon and is selected from carboxy, carbamoyl, acetyl, N-(butyl)carbamoyl, N-(methoxy)carbamoyl, ethoxycarbonyl or isopropoxycarbonyl.

In another embodiment of the compounds represented by formula (I), (XVI), (XV), (XVI), or (XVII), p is 0 or 1.

In another embodiment of the compounds represented by formula (I), (XVI), (XV), (XVI), or (XVII), p is 0.

In another embodiment of the compounds represented by formula (I), (XVI), (XV), (XVI), or (XVII), p is 1.

In one embodiment of the compounds represented by formula (I), Ring A is a nitrogen containing 5 or 6 membered heterocyclic group; wherein the nitrogen drawn is =N— and is ortho to the $R^1R^2NC(O)NH$ group of formula (I); selected from pyridyl, thiazolyl and pyrimidinyl.

In another embodiment of the compounds represented by formula (I), Ring A is a nitrogen containing 5 or 6 membered heterocyclic group; wherein the nitrogen drawn is =N— and is ortho to the $R^1R^2NC(O)NH$ group of formula (I); selected from pyridyl.

In another embodiment of the compounds represented by formula (I), Ring A is a nitrogen containing 5 or 6 membered heterocyclic group; wherein the nitrogen drawn is =N— and is ortho to the $R^1R^2NC(O)NH$ group of formula (I); selected from thiazolyl.

In another embodiment of the compounds represented by formula (I), Ring A is a nitrogen containing 5 or 6 membered heterocyclic group; wherein the nitrogen drawn is =N— and is ortho to the $R^1R^2NC(O)NH$ group of formula (I); selected from pyrimidinyl.

In one embodiment of the compounds represented by formula (I), (XVI), (XV), or (XVI), (XVII), or (XVIII), Ring B is carbocyclyl.

In another embodiment of the compounds represented by formula (I), (XVI), (XV), or (XVI), (XVII), or (XVIII), Ring B is or heterocyclyl; wherein if said heterocyclyl contains an —NH— moiety that nitrogen may be optionally substituted by a group selected from $R^{14}$.

In another embodiment of the compounds represented by formula (I), (XVI), (XV), or (XVI), (XVII), or (XVIII), Ring B is pyridyl, thiazolyl, benzothiazolyl, phenyl and imidazo[1,2-a]pyridinyl.

In another embodiment of the compounds represented by formula (I), (XVI), (XV), or (XVI), (XVII), or (XVIII), Ring B is pyridyl.

In another embodiment of the compounds represented by formula (I), (XVI), (XV), or (XVI), (XVII), or (XVIII), Ring B is thiazolyl.

In another embodiment of the compounds represented by formula (I), (XVI), (XV), or (XVI), (XVII), or (XVIII), Ring B is benzothiazolyl.

In another embodiment of the compounds represented by formula (I), (XVI), (XV), or (XVI), (XVII), or (XVIII), Ring B is phenyl.

In another embodiment of the compounds represented by formula (I), (XVI), (XV), or (XVI), (XVII), or (XVIII), Ring B is imidazo[1,2-a]pyridinyl.

In another embodiment of the compounds represented by formula (I), (XVI), (XV), or (XVI), (XVII), or (XVIII), Ring B is quinolin-4(1H)-one.

In another embodiment of the compounds represented by formula (I), (XVI), (XV), or (XVI), (XVII), or (XVIII), Ring B is pyridin-2(1H)-one.

In one embodiment of the compounds represented by formula (I), (XVI), (XV), (XVI), (XVII), (XVIII), (XIX), or (XX), $R^5$ is selected from hydroxy, —N($R^{15}$)($R^{16}$) and a nitrogen linked heterocyclyl; wherein if said nitrogen linked heterocyclyl contains an —NH— moiety that nitrogen may be optionally substituted by a group selected from $R^{18}$.

In another embodiment of the compounds represented by formula (I), (XVI), (XV), (XVI), (XVII), (XVIII), (XIX), or (XX), $R^5$ is hydroxy, amino, a $C_{1-4}$alkoxy, an N—($C_{1-4}$alkyl)amino, an N,N—($C_{1-4}$alkyl)amino, or an N—($C_{3-6}$cycloalkyl)amino, wherein the $C_{1-4}$alkoxy is optionally substituted on one or more carbon atoms with one or more $R^{17}$; and wherein N—($C_{1-4}$alkyl)amino, N,N—($C_{1-4}$alkyl)amino, or N—($C_{3-6}$cycloalkyl)amino may be optionally substituted on one or more carbon atoms with one or more $R^{21}$.

In another embodiment of the compounds represented by formula (I), (XVI), (XV), (XVI), (XVII), (XVIII), (XIX), or (XX), $R^5$ is selected from hydroxy, $C_{1-6}$alkoxy and —N($R^{15}$)($R^{16}$); wherein $R^{15}$ and $R^{16}$ are independently selected from hydrogen, $C_{1-6}$alkyl, $C_{1-6}$alkoxy or carbocyclyl.

In another embodiment of the compounds represented by formula (I), (XVI), (XV), (XVI), (XVII), (XVIII), (XIX), or (XX), $R^5$ is selected from hydroxy, methoxy, ethoxy and —N($R^{15}$)($R^{16}$); wherein $R^{15}$ and $R^{16}$ are independently selected from hydrogen, methyl, butyl, methoxy or cyclopropyl.

In another embodiment of the compounds represented by formula (I), (XVI), (XV), (XVI), (XVII), (XVIII), (XIX), or (XX), $R^5$ is selected from hydroxy, methoxy, ethoxy, methylamino, butylamino, cyclopropylamino and methoxyamino.

Therefore in a further aspect of the invention there is provided a compound of formula (I) (as depicted above) wherein:

$R^1$ is $C_{1-6}$alkyl;

$R^2$ is hydrogen;

m is 0;

$R^4$ is a substituent on carbon and is selected from carboxy, carbamoyl, $C_{1-6}$alkanoyl, N—($C_{1-6}$alkyl)carbamoyl, N—($C_{1-6}$alkoxy)carbamoyl or $C_{1-6}$alkoxycarbonyl;

p is 0 or 1;

Ring A is a nitrogen containing 5 or 6 membered heterocyclic group; wherein the nitrogen drawn is =N— and is ortho to the $R^1R^2NC(O)NH$ group of formula (I); selected from pyridyl, thiazolyl and pyrimidinyl;

Ring B is pyridyl, thiazolyl, benzothiazolyl, phenyl and imidazo[1,2-a]pyridinyl;

$R^5$ is selected from hydroxy, $C_{1-6}$alkoxy and —N($R^{15}$)($R^{16}$); and $R^{15}$ and $R^{16}$ are independently selected from hydrogen, $C_{1-6}$alkyl, $C_{1-6}$alkoxy or carbocyclyl;

or a pharmaceutically acceptable salt thereof.

Therefore in a further aspect of the invention there is provided a compound of formula (I) (as depicted above) wherein:
$R^1$ is ethyl;
$R^2$ is hydrogen;
m is 0;
$R^4$ is a substituent on carbon and is selected from carboxy, carbamoyl, acetyl, N-(butyl)carbamoyl, N-(methoxy)carbamoyl, ethoxycarbonyl or isopropoxycarbonyl;
p is 0 or 1;
Ring A is a nitrogen containing 5 or 6 membered heterocyclic group; wherein the nitrogen drawn is =N— and is ortho to the $R^1R^2NC(O)NH$ group of formula (I); selected from pyridyl, thiazolyl and pyrimidinyl;
Ring B is pyridyl, thiazolyl, benzothiazolyl, phenyl and imidazo[1,2-a]pyridinyl; and
$R^5$ is selected from hydroxy, methoxy, ethoxy, methylamino, butylamino, cyclopropylamino and methoxyamino;
or a pharmaceutically acceptable salt thereof.

Therefore in a further aspect of the invention there is provided a compound of formula (XIV), (XV), or (XVI) (as depicted above) wherein:
$R^1$ is $C_{1-6}$alkyl;
$R^2$ is hydrogen;
m is 0;
$R^4$ is a substituent on carbon and is selected from carboxy, carbamoyl, $C_{1-6}$alkanoyl, N—($C_{1-6}$alkyl)carbamoyl, N—($C_{1-6}$alkoxy)carbamoyl or $C_{1-6}$alkoxycarbonyl;
p is 0 or 1;
Ring B is pyridyl, thiazolyl, benzothiazolyl, phenyl and imidazo[1,2-a]pyridinyl;
$R^5$ is selected from hydroxy, $C_{1-6}$alkoxy and —N($R^{15}$)($R^{16}$); and
$R^{15}$ and $R^{16}$ are independently selected from hydrogen, $C_{1-6}$alkyl, $C_{1-6}$alkoxy or carbocyclyl;
or a pharmaceutically acceptable salt thereof.

Therefore in a further aspect of the invention there is provided a compound of formula (XIV), (XV), or (XVI) (as depicted above) wherein:
$R^1$ is ethyl;
$R^2$ is hydrogen;
m is 0;
$R^4$ is a substituent on carbon and is selected from carboxy, carbamoyl, acetyl, N-(butyl)carbamoyl, N-(methoxy)carbamoyl, ethoxycarbonyl or isopropoxycarbonyl;
p is 0 or 1;
Ring B is pyridyl, thiazolyl, benzothiazolyl, phenyl and imidazo[1,2-a]pyridinyl; and
$R^5$ is selected from hydroxy, methoxy, ethoxy, methylamino, butylamino, cyclopropylamino and methoxyamino;
or a pharmaceutically acceptable salt thereof.

Therefore in a further aspect of the invention there is provided a compound of formula (XVII) (as depicted above) wherein:
$R^1$ is $C_{1-6}$alkyl;
$R^2$ is hydrogen;
$R^4$ is a substituent on carbon and is selected from carboxy, carbamoyl, $C_{1-6}$alkanoyl, N—($C_{1-6}$alkyl)carbamoyl, N—($C_{1-6}$alkoxy)carbamoyl or $C_{1-6}$alkoxycarbonyl;
p is 0 or 1;
Ring B is pyridyl, thiazolyl, benzothiazolyl, phenyl and imidazo[1,2-a]pyridinyl;
$R^5$ is selected from hydroxy, $C_{1-6}$alkoxy and —N($R^{15}$)($R^{16}$); and
$R^{15}$ and $R^{16}$ are independently selected from hydrogen, $C_{1-6}$alkyl, $C_{1-6}$alkoxy or carbocyclyl;
or a pharmaceutically acceptable salt thereof.

Therefore in a further aspect of the invention there is provided a compound of formula (XVII) (as depicted above) wherein:
$R^1$ is ethyl;
$R^2$ is hydrogen;
$R^4$ is a substituent on carbon and is selected from carboxy, carbamoyl, acetyl, N-(butyl)carbamoyl, N-(methoxy)carbamoyl, ethoxycarbonyl or isopropoxycarbonyl;
p is 0 or 1;
Ring B is pyridyl, thiazolyl, benzothiazolyl, phenyl and imidazo[1,2-a]pyridinyl; and
$R^5$ is selected from hydroxy, methoxy, ethoxy, methylamino, butylamino, cyclopropylamino and methoxyamino;
or a pharmaceutically acceptable salt thereof.

Therefore in a further aspect of the invention there is provided a compound of formula (XVIII) (as depicted above) wherein:
$R^1$ is $C_{1-6}$alkyl;
Ring B is pyridyl, thiazolyl, benzothiazolyl, phenyl and imidazo[1,2-a]pyridinyl;
$R^5$ is selected from hydroxy, $C_{1-6}$alkoxy and —N($R^{15}$)($R^{16}$); and
$R^{15}$ and $R^{16}$ are independently selected from hydrogen, $C_{1-6}$alkyl, $C_{1-6}$alkoxy or carbocyclyl;
$R^{29}$ is selected from the group consisting of pyridinyl, thiazolyl, and phenyl, wherein the pyridinyl, thiazolyl or phenyl may be optionally substituted on one or more carbon atom with one or more $R^{11}$; and
$R^{11}$, for each occurrence, is independently selected from halo, $C_{1-6}$alkyl, or $C_{1-6}$haloalkyl;
or a pharmaceutically acceptable salt thereof.

Therefore in a further aspect of the invention there is provided a compound of formula (XVIII) (as depicted above) wherein:
$R^1$ is ethyl;
Ring B is pyridyl, thiazolyl, benzothiazolyl, phenyl and imidazo[1,2-a]pyridinyl; and
$R^5$ is selected from hydroxy, methoxy, ethoxy, methylamino, butylamino, cyclopropylamino and methoxyamino;
$R^{29}$ is selected from the group consisting of pyridinyl, thiazolyl, and phenyl, wherein the pyridinyl, thiazolyl or phenyl may be optionally substituted on one or more carbon atom with one or more $R^{11}$; and
$R^{11}$, for each occurrence, is independently selected from fluoro, trifluoromethyl, or ethyl;
or a pharmaceutically acceptable salt thereof.

Therefore in a further aspect of the invention there is provided a compound of formula (XIX) or (XX) (as depicted above) wherein:
$R^1$ is $C_{1-6}$alkyl;
$R^5$ is selected from hydroxy, $C_{1-6}$alkoxy and —N($R^{15}$)($R^{16}$); and
$R^{15}$ and $R^{16}$ are independently selected from hydrogen, $C_{1-6}$alkyl, $C_{1-6}$alkoxy or carbocyclyl; and
$R^{11}$ is halo, $C_{1-6}$alkyl, or $C_{1-6}$haloalkyl;
or a pharmaceutically acceptable salt thereof.

Therefore in a further aspect of the invention there is provided a compound of formula (XVIII) or (XX) (as depicted above) wherein:
$R^1$ is ethyl;
$R^5$ is selected from hydroxy, methoxy, ethoxy, methylamino, butylamino, cyclopropylamino and methoxyamino; and
$R^{11}$, for each occurrence, is independently selected from fluoro, trifluoromethyl, or ethyl;
or a pharmaceutically acceptable salt thereof.

Particular compounds of the invention are the compounds of the Examples, each of which provides a further independent aspect of the invention. In further aspects, the present invention also comprises any two or more compounds of the Examples.

In one embodiment of the invention are provided compounds of formula (I), (XIV), (XV), (XVI), (XVII), (XVIII), (XIX), or (XX), in an alternative embodiment are provided pharmaceutically-acceptable salts of compounds of formula (I), (XIV), (XV), (XVI), (XVII), (XVIII), (XIX), or (XX).

In a further aspect the present invention provides a process for preparing a compound of formula (I), (XIV), (XV), (XVI), (XVII), (XVIII), (XIX), or (XX), or a pharmaceutically-acceptable salt thereof.

Another aspect of the present invention provides a process for preparing a compound of formula (I), or any embodiment thereof, or a pharmaceutically acceptable salt thereof which process (wherein variable groups are, unless otherwise specified, as defined in formula (I)) comprises of:

Process a) reacting an amine of formula (II):

(II)

with an acid of formula (III):

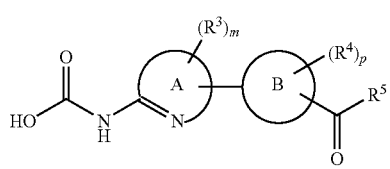
(III)

or an activated derivative thereof;

Process b) reacting an acid of formula (IV):

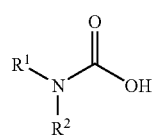
(IV)

or an activated derivative thereof; with an amine of formula (V):

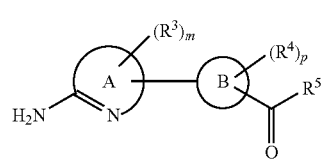
(V)

Process c) for compounds of formula (I) wherein $R^2$ is hydrogen; reacting an isocyanate of formula (VI):

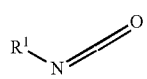
(VI)

with a compound of formula (V);

Process d) reacting an isocyanate of formula (VII):

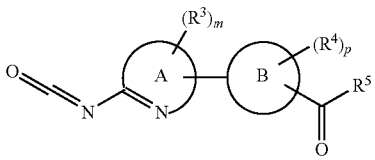
(VII)

with a compound of formula (II);

Process e) for compounds of formula (I) wherein Ring A is attached to a double bond of Ring B and Ring B is attached to a double bond of Ring A; reacting a compound of formula (VIII):

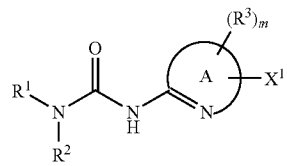
(VIII)

with a compound of formula (IX):

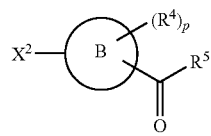
(IX)

wherein one of $X^1$ and $X^2$ is a displaceable group "L" and the other is an organometallic reagent "M";

Process f) for compounds of formula (I) wherein $R^5$ is hydroxy; deprotecting a compound of formula (X):

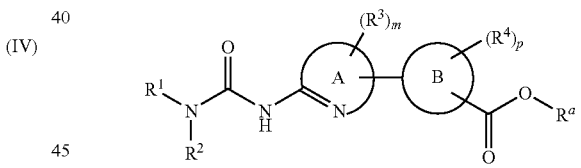
(X)

wherein $R^a$ is a carboxy protecting group;

Process g) for compounds of formula (I) wherein $R^5$ is —$N(R^{15})(R^{16})$ or a nitrogen linked heterocyclyl; reacting a compound of formula (XI):

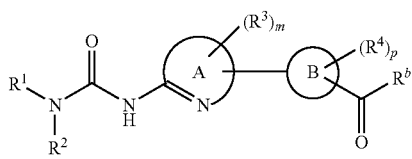
(XI)

wherein $R^b$ is hydroxy or a displaceable group; with a compound of formula (XII) or (XIII):

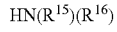
(XII)

(XIII)

wherein Ring X is an —NH— containing heterocyclyl; and thereafter if necessary:

i) converting a compound of the formula (I) into another compound of the formula (I);

ii) removing any protecting groups;

iii) forming a pharmaceutically acceptable salt.

$R^a$ is a carboxy protecting group, suitable carboxy protecting groups are defined herein below.

L is a displaceable group, suitable values for L include chloro, bromo, tosyl and trifluoromethylsulphonyloxy.

M is an organometallic reagent, suitable values for M include organoboron and organotin reagents, in particular $B(OR^z)_2$ where $R^z$ is hydrogen or $C_{1-6}$alkyl for example $B(OH)_2$; and $Sn(R^y)_3$ where $R^y$ is $C_{1-6}$alkyl for example $Sn(Bu)_3$.

A suitable displaceable group for $R^b$ may be an ester group, for example $C_{1-6}$alkoxy esters, allyloxy ester, benzyloxy ester, activated esters including esters formed with 1-hydroxybenzotriazole, 1-[bis(dimethylamino)methylene]-1H-1,2,3-triazolo[4,5-b]pyridinum 3-oxide hexafluorophosphate, 1-(3-dimethylaminopropyl)3-ethylcarbodiimide hydrochloride and catbonyldiimidazole; or a halo group, for example chloro or bromo.

Specific reaction conditions for the above reactions are as follows. Process a) and Process b) Amines and acids may be coupled together in the presence of a suitable coupling reagent. Standard peptide coupling reagents known in the art can be employed as suitable coupling reagents, or for example carbonyldiimidazole and dicyclohexyl-carbodiimide (DCC) or 1-ethyl-3-(3-dimethyllaminopropyl)carbodiimide (EDC), optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Compounds of formula (III) may be prepared according to the following scheme:

Scheme 1

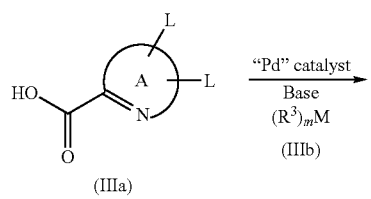

(IIIa)

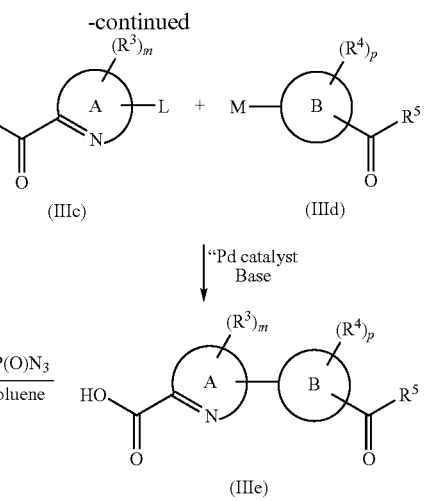

Where L and M are as defined herein above.

Compounds of formula (V) may be prepared according to the following scheme:

Scheme 2

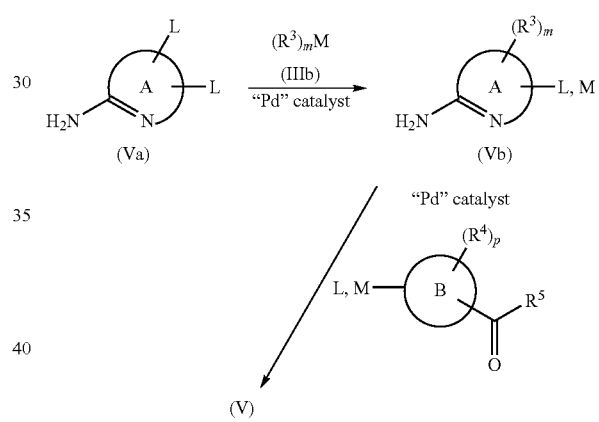

Where L and M are as defined herein above.

Compounds of formula (II), (IIIa), (IIIb), (Va) and (IV) are commercially available compounds, or they are known in the literature or they may be prepared by standard processes known in the art.

Process c) and Process d) Isocyanates and amines may be coupled together in a suitable solvent such as chloroform, dicholormethane, toluene, or N-methylpyrrolidine in the presence of base such as triethylamine and with the addition of heat.

Compounds of formula (VII) may be prepared according to the following scheme:

Scheme 3

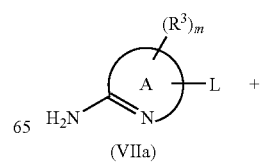

(VIIa)

-continued

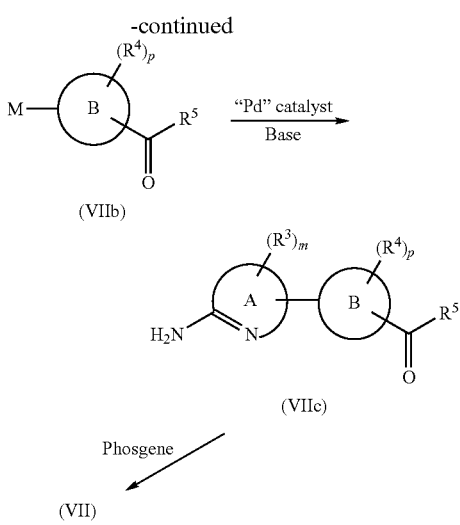

Where L and M are as defined herein above.

Compounds of formula (VI), (VIIa) and (VIIb) are commercially available compounds, or they are known in the literature or they may be prepared by standard processes known in the art.

Process e) Compounds of formula (VIII) and (IX) may be reacted together by coupling chemistry utilizing an appropriate catalyst. Such reactions are well known in the art. For example, where M is an organoboron group, Pd(PPh$_3$)$_4$ and a suitable base such as sodium carbonate can be utilized. In the case where M is an organotin reagent, Pd(PPh$_3$)$_4$ can be utilized as the catalyst. The reactions take place in suitable solvents and may require thermal conditions.

Compounds of formula (VIII) may be prepared according to the following scheme:

Scheme 4

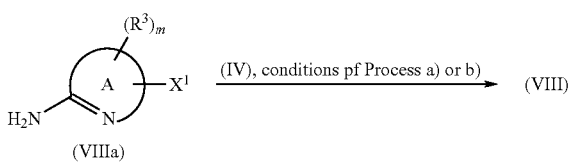

Compounds of formula (VIIIa) and (IX) are commercially available compounds, or they are known in the literature or they may be prepared by standard processes known in the art.

Process f) suitable carboxy deprotection conditions are outlined herein below.

Compounds of formula (X) may be prepared by suitable variations of the reactions described herein to make compounds of formula (I).

Process g) Suitable conditions for this reaction are outlined in Process a) or Process b).

Compounds of formula (XI) may be prepared by suitable variations of the reactions described herein to make compounds of formula (I).

Compounds of formula (XII) and (XIII) are commercially available compounds, or they are known in the literature or they may be prepared by standard processes known in the art.

The formation of a pharmaceutically-acceptable salt is within the skill of an ordinary organic chemist using standard techniques.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. The reagents used to introduce such ring substituents are either commercially available or are made by processes known in the art.

Introduction of substituents into a ring may convert one compound of the formula (I) into another compound of the formula (I). Such reactions and modifications include, for example, introduction of a substituent by means of an aromatic substitution reaction, reduction of substituents, alkylation of substituents, oxidation of substituents, esterification of substituents, amidation of substituents, formation of heteroaryl rings. The reagents and reaction conditions for such procedures are well known in the chemical art. Particular examples of aromatic substitution reactions include the introduction of alkoxides, diazotization reactions followed by introduction of thiol group, alcohol group, halogen group. Examples of modifications include; oxidation of alkylthio to alkylsulphinyl or alkylsulphonyl.

The skilled organic chemist will be able to use and adapt the information contained and referenced within the above references, and accompanying Examples therein and also the Examples herein, to obtain necessary starting materials, and products. If not commercially available, the necessary starting materials for the procedures such as those described above may be made by procedures which are selected from standard organic chemical techniques, techniques which are analogous to the synthesis of known, structurally similar compounds, or techniques which are analogous to the above described procedure or the procedures described in the examples. It is noted that many of the starting materials for synthetic methods as described above are commercially available and/or widely reported in the scientific literature, or could be made from commercially available compounds using adaptations of processes reported in the scientific literature. The reader is further referred to Advanced Organic Chemistry, 4$^{th}$ Edition, by Jerry March, published by John Wiley & Sons 1992, for general guidance on reaction conditions and reagents.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, Protective Groups in Organic Synthesis, John Wiley and Sons, 1991).

Examples of a suitable protecting group for a hydroxy group is, for example, an acyl group, for example an alkanoyl group such as acetyl, an aroyl group, for example benzoyl, a silyl group such as trimethylsilyl or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl may be removed, for example, by fluoride or by aqueous acid; or an arylmethyl group such as a benzyl group may be removed, for example, by hydrogenation in the presence of a catalyst such as palladium-on-carbon.

A suitable protecting group for an amino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine or 2-hydroxyethylamine, or with hydrazine.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon, or for example, an allyl group which may be removed, for example, by use of a palladium catalyst such as palladium acetate.

The protecting groups may be removed at any convenient stage in the synthesis using conventional techniques well known in the chemical art, or they may be removed during a later reaction step or work-up.

When an optically active form of a compound of the invention is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

Enzyme Potency Testing Methods

Compounds were tested for inhibition of GyrB ATPase activity using an ammonium molybdate/malachite green-based phosphate detection assay (Lanzetta, P. A., L. J. Alvarez, P. S. Reinach, and O. A. Candia, 1979, 100: 95-97). Assays were performed in multiwell plates in 100 µl reactions containing: 50 mM TRIS buffer pH 7.5, 75 mM ammonium acetate, 5.5 mM magnesium chloride, 0.5 mM ethylenediaminetetraacetic acid, 5% glycerol, 1 mM 1,4-Dithio-DL-threitol, 200 nM bovine serum albumin, 16 µg/ml sheared salmon sperm DNA, 4 nM E. coli GyrA, 4 nM E. coli GyrB, 250 µM ATP, and compound in dimethylsulfoxide. Reactions were quenched with 150 µl of ammonium molybdate/malachite green detection reagent containing 1.2 mM malachite green hydrochloride, 8.5 mM ammonium molybdate tetrahydrate, and 1 M hydrochloric acid. Plates were read in an absorbance plate reader at 625 nm and percent inhibition values were calculated using dimethylsulfoxide (2%)-containing reactions as 0% inhibition and novobiocin-containing (2 µM) reactions as 100% inhibition controls. Compound potency was based on $IC_{50}$ measurements determined from reactions performed in the presence of 10 different compound concentrations.

Compounds were tested for inhibition of topoisomerase IV ATPase activity as described above for GyrB except the 100 µl reactions contained the following: 20 mM TRIS buffer pH 8, 50 mM ammonium acetate, 8 mM magnesium chloride, 5% glycerol, 5 mM 1,4-Dithio-DL-threitol, 0.005% Brij-35, 5 µg/ml sheared salmon sperm DNA, 10 nM E. coli ParC, 10 nM E. coli ParE, 160 µM ATP, and compound in dimethylsulfoxide. Compound potency was based on $IC_{50}$ measurements determined from reactions performed in the presence of 10 different compound concentrations.

Compounds of the invention generally have $IC_{50}$ values of <200 µg/ml in one or both assays described herein above.

Compounds were tested for inhibition of GyrB ATPase activity using an ammonium molybdate/malachite green-based phosphate detection assay (Lanzetta, P. A., L. J. Alvarez, P. S. Reinach, and O. A. Candia, 1979, 100: 95-97). Assays were performed in multiwell plates in 100 µl reactions containing: 50 mM Hepes buffer pH 7.5, 75 mM ammonium acetate, 8.0 mM magnesium chloride, 1.0 mM ethylenediaminetetraacetic acid, 5% glycerol, 2 mM 1,4-Dithio-DL-threitol, 400 nM bovine serum albumin, 5 µg/ml sheared salmon sperm DNA, 1.25 nM E. coli GyrA, 1.25 nM S. aureus GyrB, 500 µM ATP, and compound in dimethylsulfoxide. Reactions were quenched with 150 µl of ammonium molybdate/malachite green detection reagent containing 1.2 mM malachite green hydrochloride, 8.5 mM ammonium molybdate tetrahydrate, and 1 M hydrochloric acid. Plates were read in an absorbance plate reader at 650 nm and percent inhibition values were calculated using dimethylsulfoxide (2%)-containing reactions as 0% inhibition and novobiocin-containing (2 µM) reactions as 100% inhibition controls. Compound potency was based on $IC_{50}$ measurements determined from reactions performed in the presence of 10 different compound concentrations.

Table 1 shows S. aureus (SAU) GyrB ATPase $IC_{50}$ values for representative compounds of the invention.

TABLE 1

| Example Number | $IC_{50}$ (µM) |
|---|---|
| 17 | 0.266 |
| 19 | 0.846 |
| 36 | 0.0168 |
| 39 | 0.014 |

Table 2 shows S. aureus (SAU) GyrB ATPase percent inhibition for compounds of the invention at a compound concentration of 12.5 µM unless otherwise noted.

TABLE 2

| Example Number | % Inhibition (µM) |
|---|---|
| 1 | 3.02 |
| 2 | 99.14 |
| 3 | 55.01 |
| 4 | 84.03 |

TABLE 2-continued

| Example Number | % Inhibition (μM) |
|---|---|
| 5 | 63.73 |
| 6 | 99.74 |
| 7 | 97.38 |
| 8 | 81.52 |
| 9 | 93.50 |
| 10 | 92.57 |
| 11 | Not available |
| 12 | 92.58 |
| 13 | 98.96 |
| 14 | 99.45* |
| 15 | 97.89 |
| 16 | 1.28* |
| 17 | 99.12 |
| 18 | 100.72 |
| 19 | 95.06 |
| 20 | 98.41 |
| 21 | 77.09 |
| 22 | 99.7 |
| 23 | 92.46 |
| 24 | 99.13 |
| 25 | 99.53 |
| 26 | 70.54 |
| 27 | 99.13 |
| 28 | 96.82 |
| 29 | 13.61 |
| 30 | 62.90 |
| 31 | 100.06 |
| 32 | 2.66 |
| 33 | 38.16 |
| 34 | 42.48* |
| 35 | 96.68* |
| 36 | 4.84 |
| 37 | 98.86 |
| 38 | 91.81 |
| 39 | 98.99 |
| 40 | 83.74 |
| 41 | 26.89 |
| 42 | Not available |
| 43 | Not available |
| 44 | Not available |
| 45 | Not available |
| 46 | 83.41 |
| 47 | 91.72 |
| 48 | 101.04 |
| 49 | 37.80 |
| 50 | Not available |
| 51 | 62.07 |
| 52 | Not available |
| 53 | Not available |
| 54 | 89.84 |
| 55 | 86.4 |
| 56 | 84.07 |
| 57 | 80.11 |
| 58 | 89.32 |
| 59 | Not available |
| 60 | Not available |
| 61 | 92.85 |
| 62 | Not available |
| 63 | Not available |
| 64 | 92.59 |
| 65 | Not available |
| 66 | Not available |
| 67 | 92.51 |
| 68 | Not available |
| 69 | 88.52 |
| 70 | 88.23 |
| 71 | 92.98 |
| 72 | 80.32 |
| 73 | Not available |
| 74 | 0.95 |
| 75 | 93.47 |
| 76 | 88.19 |
| 77 | 101.46 |
| 78 | Not available |
| 79 | Not available |
| 80 | Not available |
| 81 | Not available |
| 82 | Not available |
| 83 | 86.87 |
| 84 | Not available |
| 85 | 94.93 |
| 86 | 99.88 |
| 87 | Not available |
| 88 | Not available |
| 89 | 86.13 |
| 90 | 19.71 |
| 91 | 100.94 |
| 92 | 101.43 |
| 93 | 99.14 |
| 94 | 98.94 |
| 95 | 100.11 |
| 96 | 95.42 |
| 97 | 101.37 |
| 98 | 99.33 |
| 99 | 102.40 |
| 100 | 99.68 |
| 101 | 98.26 |
| 102 | 98.20 |
| 103 | 96.04 |
| 104 | 89.92 |
| 105 | 94.75 |
| 106 | 93.1 |
| 107 | 83.95 |
| 108 | 100.44 |
| 109 | 99.48 |
| 110 | 100.89 |
| 111 | 100.96 |
| 112 | 99.91 |
| 113 | 101.53 |
| 114 | 105.38 |
| 115 | 99.18 |
| 116 | 98.74 |
| 117 | 101.33 |
| 118 | 101.75 |
| 119 | 102.99 |
| 120 | Not available |
| 121 | 81.82 |
| 122 | 85.75 |
| 123 | 96.24 |
| 124 | 95.06 |
| 125 | 107.06 |
| 126 | 96.24 |
| 127 | 96.99 |
| 128 | 91.47 |
| 129 | 100.02 |
| 130 | 98.67 |
| 131 | 59.98 |
| 132 | Not available |
| 133 | Not available |
| 134 | 7.09 |
| 135 | 0.52 |
| 136 | 60.97 |
| 137 | 86.92 |
| 138 | 94.77 |
| 139 | 96.72 |
| 140 | 76.56 |
| 141 | 99.23 |
| 142 | 0.68 |
| 143 | 99.11 |
| 144 | 38.56 |
| 145 | 100.53 |
| 146 | 64.3 |
| 147 | 94.65 |
| 148 | 94.15 |
| 149 | 97.52 |
| 150 | 100.30 |
| 151 | 97.71 |
| 152 | 69.36 |
| 153 | 71.43 |
| 154 | 99.81 |
| 155 | 82.32 |
| 156 | 42.95 |
| 157 | 101.23 |
| 158 | 92.60 |

TABLE 2-continued

| Example Number | % Inhibition (μM) |
| --- | --- |
| 159 | 95.32 |
| 160 | 95.49 |
| 161 | 101.17 |
| 162 | 100.67 |
| 163 | 97.75 |
| 164 | 88.11 |
| 165 | Not available |

*Note: Percent inhibition was measured at a compound concentration of 5 μM.

Bacterial Susceptibility Testing Methods

Compounds were tested for antimicrobial activity by susceptibility testing in liquid media. Compounds were dissolved in dimethylsulfoxide and tested in 10 doubling dilutions in the susceptibility assays. The organisms used in the assay were grown overnight on suitable agar media and then suspended in a liquid medium appropriate for the growth of the organism. The suspension was a 0.5 McFarland and a further 1 in 10 dilution was made into the same liquid medium to prepare the final organism suspension in 100 μL. Plates were incubated under appropriate conditions at 37° C. for 24 hrs prior to reading. The Minimum Inhibitory Concentration was determined as the lowest drug concentration able to reduce growth by 80% or more.

Example 26 had an MIC of 2.0 μg/ml against *Streptococcus pneumoniae*.

According to a further feature of the invention there is provided a compound of the formula (I), (XIV), (XV), (XVI), (XVII), (XVIII), (XIX), or (XX), or a pharmaceutically-acceptable salt thereof for use in a method of treatment of the human or animal body by therapy.

In one embodiment, the invention provides a method of treating a bacterial infection in an animal, such as a human, comprising administering to the animal or human an effective amount of a compound of any one of formulas (I), (XIV), (XV), (XVI), (XVII), (XVIII), (XIX), and (XX), or a pharmaceutically acceptable salt thereof.

We have found that compounds of the present invention inhibit bacterial DNA gyrase and/or topoisomerase IV and are therefore of interest for their antibacterial effects. In one aspect of the invention the compounds of the invention inhibit bacterial DNA gyrase and are therefore of interest for their antibacterial effects. In one aspect of the invention, the compounds of the invention inhibit topoisomerase IV and are therefore of interest for their antibacterial effects. In one aspect of the invention, the compounds of the invention inhibit both DNA gyrase and topoisomerase IV and are therefore of interest for their antibacterial effects. Thus, the compounds of the invention are useful in treating or preventing bacterial infections.

In one aspect of the invention an "infection" or "bacterial infection" refers to an infection caused by *Acinetobacter baumanii*. In one aspect of the invention an "infection" or "bacterial infection" refers to an infection caused by *Acinetobacter haemolyticus*. In one aspect of the invention an "infection" or "bacterial infection" refers to an infection caused by *Acinetobacter junii*. In one aspect of the invention an "infection" or "bacterial infection" refers to an infection caused by *Acinetobacter johnsonii*. In one aspect of the invention an "infection" or "bacterial infection" refers to an infection caused by *Acinetobacter lwoffi*. In one aspect of the invention an "infection" or "bacterial infection" refers to an infection caused by *Bacteroides bivius*. In one aspect of the invention an "infection" or "bacterial infection" refers to an infection caused by *Bacteroides fragilis*. In one aspect of the invention an "infection" or "bacterial infection" refers to an infection caused by *Burkholderia cepacia*. In one aspect of the invention an "infection" or "bacterial infection" refers to an infection caused by *Campylobacter jejuni*. In one aspect of the invention an "infection" or "bacterial infection" refers to an infection caused by *Chlamydia pneumoniae*. In one aspect of the invention an "infection" or "bacterial infection" refers to an infection caused by *Chlamydia urealyticus*. In one aspect of the invention an "infection" or "bacterial infection" refers to an infection caused by *Chlamydophila pneumoniae*. In one aspect of the invention an "infection" or "bacterial infection" refers to an infection caused by *Clostridium difficile*. In one aspect of the invention an "infection" or "bacterial infection" refers to an infection caused by *Enterobacter aerogenes*. In one aspect of the invention an "infection" or "bacterial infection" refers to an infection caused by *Enterobacter cloacae*. In one aspect of the invention an "infection" or "bacterial infection" refers to an infection caused by *Enterococcus faecalis*. In one aspect of the invention an "infection" or "bacterial infection" refers to an infection caused by *Enterococcus faecium*. In one aspect of the invention an "infection" or "bacterial infection" refers to an infection caused by *Escherichia coli*. In one aspect of the invention an "infection" or "bacterial infection" refers to an infection caused by *Gardnerella vaginalis*. In one aspect of the invention an "infection" or "bacterial infection" refers to an infection caused by *Haemophilus parainfluenzae*. In one aspect of the invention an "infection" or "bacterial infection" refers to an infection caused by *Haemophilus influenzae*. In one aspect of the invention an "infection" or "bacterial infection" refers to an infection caused by *Helicobacter pylori*. In one aspect of the invention an "infection" or "bacterial infection" refers to an infection caused by *Klebsiella pneumoniae*. In one aspect of the invention an "infection" or "bacterial infection" refers to an infection caused by *Legionella pneumophila*. In one aspect of the invention an "infection" or "bacterial infection" refers to an infection caused by Methicillin-resistant *Staphylococcus aureus*. In one aspect of the invention an "infection" or "bacterial infection" refers to an infection caused by Methicillin-susceptible *Staphylococcus aureus*. In one aspect of the invention an "infection" or "bacterial infection" refers to an infection caused by *Moraxella catarrhalis*. In one aspect of the invention an "infection" or "bacterial infection" refers to an infection caused by *Morganella morganii*. In one aspect of the invention an "infection" or "bacterial infection" refers to an infection caused by *Mycoplasma pneumoniae*. In one aspect of the invention an "infection" or "bacterial infection" refers to an infection caused by *Neisseria gonorrhoeae*. In one aspect of the invention an "infection" or "bacterial infection" refers to an infection caused by Penicillin-resistant *Streptococcus pneumoniae*. In one aspect of the invention an "infection" or "bacterial infection" refers to an infection caused by Penicillin-susceptible *Streptococcus pneumoniae*. In one aspect of the invention an "infection" or "bacterial infection" refers to an infection caused by *Peptostreptococcus magnus*. In one aspect of the invention an "infection" or "bacterial infection" refers to an infection caused by *Peptostreptococcus micros*. In one aspect of the invention an "infection" or "bacterial infection" refers to an infection caused by *Peptostreptococcus anaerobius*. In one aspect of the invention an "infection" or "bacterial infection" refers to an infection caused by *Peptostreptococcus asaccharolyticus*. In one aspect of the invention an "infection" or "bacterial infection" refers to an infection caused by *Peptostreptococcus prevotii*. In one aspect of the invention an "infection" or "bacterial infection" refers to an infection caused by *Peptostreptococcus tetradius*. In one aspect of the invention an "infection" or "bacterial infection" refers to an infection caused by *Peptostreptococcus vaginalis*. In one aspect of the invention an "infection" or "bacterial infection" refers to an infection caused by *Proteus mirabilis*. In one aspect of the invention an "infection" or "bacterial infection" refers to an infection caused by *Pseudomonas aeruginosa*. In one aspect of the invention an "infection" or "bacterial infection" refers to an infection caused by Quinolone-Resistant *Staphylococcus aureus*. In one aspect of the invention an "infection" or "bacterial infection" refers to an infection caused by Quinolone-Resistant *Staphylococcus epidermis*. In one aspect of the invention an "infection" or "bacterial infection" refers to an infection caused by *Salmonella typhi*. In one aspect of the invention an "infection" or "bacterial infection" refers to an infection caused by *Salmonella paratyphi*. In one aspect of the invention an "infection" or "bacterial infection" refers to an infection caused by *Salmonella enteritidis*. In one aspect of the invention an "infection" or "bacterial infection" refers to an infection caused by *Salmonella typhimurium*. In one aspect of the invention an "infection" or "bacterial infection" refers to an infection caused by *Serratia marcescens*. In one aspect of the invention an "infection" or "bacterial infection" refers to an infection caused by *Staphylococcus aureus*. In one aspect of the invention an "infection" or "bacterial infection" refers to an infection caused by *Staphylococcus epidermidis*. In one aspect of the invention an "infection" or "bacterial infection" refers to an infection caused by *Staphylococcus saprophyticus*. In one aspect of the invention an "infection" or "bacterial infection" refers to an infection caused by *Streptoccocus agalactiae*. In one aspect of the invention an "infection" or "bacterial infection" refers to an infection caused by *Streptococcus pneumoniae*. In one aspect of the invention an "infection" or "bacterial infection" refers to an infection caused by *Streptococcus pyogenes*. In one aspect of the invention an "infection" or "bacterial infection" refers to an infection caused by *Stenotrophomonas maltophilia*. In one aspect of the invention an "infection" or "bacterial infection" refers to an infection caused by *Ureaplasma urealyticum*. In one aspect of the invention an "infection" or "bacterial infection" refers to an infection caused by Vancomycin-Resistant *Enterococcus faecium*. In one aspect of the invention an "infection" or "bacterial infection" refers to an infection caused by Vancomycin-Resistant *Enterococcus faecalis*. In one aspect of the invention an "infection" or "bacterial infection" refers to an infection caused by Vancomycin-Resistant *Staphylococcus aureus*. In one aspect of the invention an "infection" or "bacterial infection" refers to an infection caused by Vancomycin-Resistant *Staphylococcus epidermis*. In one aspect of the invention an "infection" or "bacterial infection" refers to an infection caused by *Mycobacterium tuberculosis*, In one aspect of the invention an "infection" or "bacterial infection" refers to an infection caused by *Clostridium perfringens*, In one aspect of the invention an "infection" or "bacterial infection" refers to an infection caused by *Klebsiella oxytoca*, In one aspect of the invention an "infection" or "bacterial infection" refers to an infection caused by *Neisseria miningitidis*. In one aspect of the invention an "infection" or "bacterial infection" refers to an infection caused by *Fusobacterium* spp, In one aspect of the invention an "infection" or "bacterial infection" refers to an infection caused by *Peptococcus* spp. In one aspect of the invention an "infection" or "bacterial infection" refers to an infection caused by *Proteus vulgaris*, In one aspect of the invention an "infection" or "bacterial infection" refers to an infection caused by Coagulase-negative *Staphylococcus* (including *Staphylococcus lugdunensis, Staphylococcus capitis, Staphylococcus hominis*, and *Staphylococcus saprophyticus*).

In one aspect of the invention an "infection" or "bacterial infection" refers to an infection caused by *Acinetobacter* spp. In one aspect of the invention an "infection" or "bacterial infection" refers to an infection caused by *Bacteroides* spp. In one aspect of the invention an "infection" or "bacterial infection" refers to an infection caused by *Burkholderia* spp. In one aspect of the invention an "infection" or "bacterial infection" refers to an infection caused by *Campylobacter* spp. In one aspect of the invention an "infection" or "bacterial infection" refers to an infection caused by *Chlamydia* spp. In one aspect of the invention an "infection" or "bacterial infection" refers to an infection caused by *Chlamydophila* spp. In one aspect of the invention an "infection" or "bacterial infection" refers to an infection caused by *Clostridium* spp. In one aspect of the invention an "infection" or "bacterial infection" refers to an infection caused by *Enterobacter* spp. In one aspect of the invention an "infection" or "bacterial infection" refers to an infection caused by *Enterococcus* spp. In one aspect of the invention an "infection" or "bacterial infection" refers to an infection caused by *Escherichia* spp. In one aspect of the invention an "infection" or "bacterial infection" refers to an infection caused by *Gardnerella* spp. In one aspect of the invention an "infection" or "bacterial infection" refers to an infection caused by *Haemophilus* spp. In one aspect of the invention an "infection" or "bacterial infection" refers to an infection caused by *Helicobacter* spp. In one aspect of the invention an "infection" or "bacterial infection" refers to an infection caused by *Klebsiella* spp. In one aspect of the invention an "infection" or "bacterial infection" refers to an infection caused by *Legionella* spp. In one aspect of the invention an "infection" or "bacterial infection" refers to an infection caused by *Moraxella* spp. In one aspect of the invention an "infection" or "bacterial infection" refers to an infection caused by *Morganella* spp. In one aspect of the invention an "infection" or "bacterial infection" refers to an infection caused by *Mycoplasma* spp. In one aspect of the invention an "infection" or "bacterial infection" refers to an infection caused by *Neisseria* spp. In one aspect of the invention an "infection" or "bacterial infection" refers to an infection caused by *Peptostreptococcus* spp. In one aspect of the invention an "infection" or "bacterial infection" refers to an infection caused by *Proteus* spp. In one aspect of the invention an "infection" or "bacterial infection" refers to an infection caused by *Pseudomonas* spp. In one aspect of the invention an "infection" or "bacterial infection" refers to an infection caused by *Salmonella* spp. In one aspect of the invention an "infection" or "bacterial infection" refers to an infection caused by *Serratia* spp. In one aspect of the invention an "infection" or "bacterial infection" refers to an infection caused by *Staphylococcus* spp. In one aspect of the invention an "infection" or "bacterial infection" refers to an infection caused by *Streptoccocus* spp. In one aspect of the invention an "infection" or "bacterial infection" refers to an infection caused by *Stenotrophomonas* spp. In one aspect of the invention an "infection" or "bacterial infection" refers to an infection caused by *Ureaplasma* spp. In one aspect of the invention an "infection" or "bacterial infection" refers to an infection caused by aerobes. In one aspect of the invention an "infection" or "bacterial infection" refers to an infection caused by obligate anaerobes. In one aspect of the invention an "infection" or "bacterial infection" refers to an infection caused by facultative anaerobes. In one aspect of the invention an "infection" or "bacterial infection" refers to an infection caused by gram-positive bacteria. In one aspect of the invention an "infection" or "bacterial infection" refers to an infection caused by gram-negative bacteria. In one aspect of the invention an "infection" or "bacterial infection" refers to an infection caused by gram-variable bacteria. In one aspect of the invention an "infection" or "bacterial infection" refers to an infection caused by atypical respiratory pathogens. In one aspect of the invention an "infection" or "bacterial infection" refers to an infection caused by Enterics. In one aspect of the invention an "infection" or "bacterial infection" refers to an infection caused by *Shigella* spp. In one aspect of the invention an "infection" or "bacterial infection" refers to an infection caused by *Citrobacter*.

In one aspect of the invention "infection" or "bacterial infection" refers to a gynecological infection. In one aspect of the invention "infection" or "bacterial infection" refers to a respiratory tract infection (RTI). In one aspect of the invention "infection" or "bacterial infection" refers to a sexually transmitted disease. In one aspect of the invention "infection" or "bacterial infection" refers to a urinary tract infection. In one aspect of the invention "infection" or "bacterial infection" refers to acute exacerbation of chronic bronchitis (ACEB). In one aspect of the invention "infection" or "bacterial infection" refers to acute otitis media. In one aspect of the invention "infection" or "bacterial infection" refers to acute sinusitis. In one aspect of the invention "infection" or "bacterial infection" refers to an infection caused by drug resistant bacteria. In one aspect of the invention "infection" or "bacterial infection" refers to catheter-related sepsis. In one aspect of the invention "infection" or "bacterial infection" refers to chancroid. In one aspect of the invention "infection" or "bacterial infection" refers to chlamydia. In one aspect of the invention "infection" or "bacterial infection" refers to community-acquired pneumonia (CAP). In one aspect of the invention "infection" or "bacterial infection" refers to complicated skin and skin structure infection. In one aspect of the invention "infection" or "bacterial infection" refers to uncomplicated skin and skin structure infection. In one aspect of the invention "infection" or "bacterial infection" refers to endocarditis. In one aspect of the invention "infection" or "bacterial infection" refers to febrile neutropenia. In one aspect of the invention "infection" or "bacterial infection" refers to gonococcal cervicitis. In one aspect of the invention "infection" or "bacterial infection" refers to gonococcal urethritis. In one aspect of the invention "infection" or "bacterial infection" refers to hospital-acquired pneumonia (HAP). In one aspect of the invention "infection" or "bacterial infection" refers to osteomyelitis. In one aspect of the invention "infection" or "bacterial infection" refers to sepsis. In one aspect of the invention "infection" or "bacterial infection" refers to syphilis. In one aspect of the invention "infection" or "bacterial infection" refers to ventilator-associated pneumonia. In one aspect of the invention "infection" or "bacterial infection" refers to intraabdominal infections. In one aspect of the invention "infection" or "bacterial infection" refers to gonorrhoeae. In one aspect of the invention "infection" or "bacterial infection" refers to meningitis. In one aspect of the invention "infection" or "bacterial infection" refers to tetanus. In one aspect of the invention "infection" or "bacterial infection" refers to tuberculosis.

In one embodiment, it is expected that the compounds of the present invention will be useful in treating bacterial infections including, but not limited to community-acquired *pneumoniae*, hospital-acquired *pneumoniae*, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococci.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt thereof.

According to a further feature of the invention there is provided a method for inhibition of bacterial DNA gyrase and/or topoisomerase IV in a warm-blooded animal, such as a human being, in need of such treatment which comprises administering to said animal an effective amount of a compound of formula (I), (XIV), (XV), (XVI), (XVII), (XVIII), (XIX), or (XX), or a pharmaceutically acceptable salt thereof as defined hereinbefore.

According to a further feature of the invention there is provided a method of treating a bacterial infection in a warm-blooded animal, such as a human being, in need of such treatment which comprises administering to said animal an effective amount of a compound of formula (I), (XIV), (XV), (XVI), (XVII), (XVIII), (XIX), or (XX), or a pharmaceutically acceptable salt thereof as defined hereinbefore.

According to a further feature of the invention there is provided a method of treating a bacterial infection selected from community-acquired *pneumoniae*, hospital-acquired *pneumoniae*, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococcii in a warm-blooded animal, such as a human being, in need of such treatment which comprises administering to said animal an effective amount of a compound of formula (I), (XIV), (XV), (XVI), (XVII), (XVIII), (XIX), or (XX), or a pharmaceutically acceptable salt thereof as defined hereinbefore.

A further feature of the present invention is a compound of formula (I), (XIV), (XV), (XVI), (XVII), (XVIII), (XIX), or (XX), and pharmaceutically acceptable salts thereof for use as a medicament. Suitably the medicament is an antibacterial agent.

According to a further aspect of the invention there is provided the use of a compound of formula (I), (XIV), (XV), (XVI), (XVII), (XVIII), (XIX), or (XX), or a pharmaceutically acceptable salt thereof in the manufacture of a medicament for use in the production of an anti-bacterial effect in a warm-blooded animal such as a human being.

According to a further aspect of the invention there is provided the use of a compound of formula (I), (XIV), (XV), (XVI), (XVII), (XVIII), (XIX), or (XX), or a pharmaceutically acceptable salt thereof in the manufacture of a medicament for use in inhibition of bacterial DNA gyrase and/or topoisomerase IV in a warm-blooded animal such as a human being.

Thus according to a further aspect of the invention there is provided the use of a compound of formula (I), (XIV), (XV), (XVI), (XVII), (XVIII), (XIX), or (XX), or a pharmaceutically acceptable salt thereof in the manufacture of a medicament for use in the treatment of a bacterial infection in a warm-blooded animal such as a human being.

Thus according to a further aspect of the invention there is provided the use of a compound of formula (I), (XIV), (XV), (XVI), (XVII), (XVIII), (XIX), or (XX), or a pharmaceutically acceptable salt thereof in the manufacture of a medicament for use in the treatment of a bacterial infection selected from community-acquired *pneumoniae*, hospital-acquired *pneumoniae*, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococci in a warm-blooded animal such as a human being.

According to a further aspect of the invention there is provided a compound of formula (I), (XIV), (XV), (XVI), (XVII), (XVIII), (XIX), or (XX), or a pharmaceutically acceptable salt thereof for use in the production of an antibacterial effect in a warm-blooded animal such as a human being.

According to a further aspect of the invention there is provided a compound of formula (I), (XIV), (XV), (XVI), (XVII), (XVIII), (XIX), or (XX), or a pharmaceutically acceptable salt thereof for use in inhibition of bacterial DNA gyrase and/or topoisomerase IV in a warm-blooded animal such as a human being.

Thus according to a further aspect of the invention there is provided a compound of formula (I), (XIV), (XV), (XVI), (XVII), (XVIII), (XIX), or (XX), or a pharmaceutically acceptable salt thereof for use in the treatment of a bacterial infection in a warm-blooded animal such as a human being.

Thus according to a further aspect of the invention there is provided a compound of formula (I), (XIV), (XV), (XVI), (XVII), (XVIII), (XIX), or (XX), or a pharmaceutically acceptable salt thereof for use in the treatment of a bacterial infection selected from community-acquired *pneumoniae*, hospital-acquired *pneumoniae*, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococci in a warm-blooded animal such as a human being.

In order to use a compound of the formula (I), (XIV), (XV), (XVI), (XVII), (XVIII), (XIX), or (XX), or a pharmaceutically-acceptable salt thereof, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I), (XIV), (XV), (XVI), (XVII), (XVIII), (XIX), or (XX), or a pharmaceutically-acceptable salt thereof, and a pharmaceutically-acceptable diluent or carrier.

According to a further aspect of the invention there is provided a pharmaceutical composition which comprises a compound of formula (I), (XIV), (XV), (XVI), (XVII), (XVIII), (XIX), or (XX), as defined hereinbefore or a pharmaceutically acceptable salt thereof, in association with a pharmaceutically acceptable excipient or carrier for use in producing an anti-bacterial effect in an warm-blooded animal, such as a human being.

According to a further aspect of the invention there is provided a pharmaceutical composition which comprises a compound of formula (I), (XIV), (XV), (XVI), (XVII), (XVIII), (XIX), or (XX), as defined hereinbefore or a pharmaceutically acceptable salt thereof, in association with a pharmaceutically acceptable excipient or carrier for use in inhibition of bacterial DNA gyrase and/or topoisomerase IV in an warm-blooded animal, such as a human being.

According to a further aspect of the invention there is provided a pharmaceutical composition which comprises a compound of formula (I), (XIV), (XV), (XVI), (XVII), (XVIII), (XIX), or (XX), as defined hereinbefore or a pharmaceutically acceptable salt thereof, in association with a pharmaceutically acceptable excipient or carrier for use in the treatment of a bacterial infection in an warm-blooded animal, such as a human being.

According to a further aspect of the invention there is provided a pharmaceutical composition which comprises a compound of formula (I), (XIV), (XV), (XVI), (XVII), (XVIII), (XIX), or (XX), as defined hereinbefore or a pharmaceutically acceptable salt thereof, in association with a pharmaceutically acceptable excipient or carrier for use in the treatment of a bacterial infection selected from community-acquired *pneumoniae*, hospital-acquired *pneumoniae*, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococci in an warm-blooded animal, such as a human being.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The compounds of the invention described herein may be applied as a sole therapy or may involve, in addition to a compound of the invention, one or more other substances and/or treatments. Such conjoint treatment may be achieved by way of the simultaneous, sequential or separate administration of the individual components of the treatment. Where the administration is sequential or separate, the delay in administering the second component should not be such as to lose the beneficial effect of the combination. Suitable classes and substances may be selected from one or more of the following:

i) other antibacterial agents for example macrolides e.g. erythromycin, azithromycin or clarithromycin; quinolones e.g. ciprofloxacin or levofloxacin; β-lactams e.g. penicillins e.g. amoxicillin or piperacillin; cephalosporins e.g. ceftriaxone or ceftazidime; carbapenems, e.g. meropenem or imipenem etc; aminoglycosides e.g. gentamicin or tobramycin; or oxazolidinones; and/or ii) anti-infective agents for example, an antifungal triazole e.g. or amphotericin; and/or iii) biological protein therapeutics for example antibodies, cytokines, bactericidal/permeability-increasing protein (BPI) products; and/or iv) efflux pump inhibitors.

Therefore, in a further aspect of the invention there is provided a compound of the formula (I), (XIV), (XV), (XVI), (XVII), (XVIII), (XIX), or (XX), or a pharmaceutically acceptable salt thereof, and a chemotherapeutic agent selected from:

i) one or more additional antibacterial agents; and/or ii) one or more anti-infective agents; and/or iii) biological protein therapeutics for example antibodies, cytokines, bactericidal/permeability-increasing protein (BPI) products; and/or iv) one or more efflux pump inhibitors.

In another embodiment, the invention relates to a method of treating a bacterial infection in an animal, such as a human, comprising administering to the animal an effective amount of a compound of formula (I), (XIV), (XV), (XVI), (XVII), (XVIII), (XIX), or (XX), or a pharmaceutically acceptable salt thereof, and a chemotherapeutic agent selected from:

i) one or more additional antibacterial agents; and/or ii) one or more anti-infective agents; and/or iii) biological protein therapeutics for example antibodies, cytokines, bactericidal/permeability-increasing protein (BPI) products; and/or iv) one or more efflux pump inhibitors.

As stated above the size of the dose required for the therapeutic or prophylactic treatment of a particular disease state will necessarily be varied depending on the host treated, the route of administration, the severity of the illness being treated, and whether or not an additional chemotherapeutic agent is administered in combination with a compound of the invention. Preferably a daily dose in the range of 1-50 mg/kg is employed. However the daily dose will necessarily be varied depending upon the host treated, the particular route of administration, the severity of the illness being treated, and whether or not an additional chemotherapeutic agent is administered in combination with a compound of the invention. Accordingly the optimum dosage may be determined by the practitioner who is treating any particular patient.

As noted above, one embodiment of the present invention is directed to treating or preventing diseases caused by bacterial infections, wherein the bacteria comprise a GyrB ATPase or topoisomerase IV ATPase enzyme. "Treating a subject with a disease caused by a bacterial infection" includes achieving, partially or substantially, one or more of the following: the reducing or amelioration of the progression, severity and/or duration of the infection, arresting the spread of an infection, ameliorating or improving a clinical symptom or indicator associated with a the infection (such as tissue or serum components), and preventing the reoccurrence of the infection.

As used herein, the terms "preventing a bacterial infection" refer to the reduction in the risk of acquiring the infection, or the reduction or inhibition of the recurrence of the infection. In a preferred embodiment, a compound of the invention is administered as a preventative measure to a patient, preferably a human, before a surgical procedure is preformed on the patient to prevent infection.

As used herein, the term "effective amount" refers to an amount of a compound of this invention for treating or preventing a bacterial infection is an amount which is sufficient to prevent the onset of an infection, reduce or ameliorate the severity, duration, or progression, of an infection, prevent the advancement of an infection, cause the regression of an infection, prevent the recurrence, development, onset or progression of a symptom associated with an infection, or enhance or improve the prophylactic or therapeutic effect(s) of another therapy.

In addition to its use in therapeutic medicine, compounds of formula (I), (XIV), (XV), (XVI), (XVII), (XVIII), (XIX), and (XX), and their pharmaceutically acceptable salts are also useful as pharmacological tools in the development and standardisation of in-vitro and in-vivo test systems for the evaluation of the effects of inhibitors of DNA gyrase and/or topoisomerase IV in laboratory animals such as cats, dogs, rabbits, monkeys, rats and mice, as part of the search for new therapeutic agents.

In the above other, pharmaceutical composition, process, method, use and medicament manufacture features, the alternative and particular embodiments of the compounds of the invention described herein also apply.

EXAMPLES

The invention is now illustrated but not limited by the following Examples in which unless otherwise stated:—

(i) evaporations were carried out by rotary evaporation in-vacuo and work-up procedures were carried out after removal of residual solids by filtration;

(ii) operations were generally carried out at ambient temperature, that is typically in the range 18-26° C. and without exclusion of air unless otherwise stated, or unless the skilled person would otherwise work under an inert atmosphere;

(iii) column chromatography (by the flash procedure) was used to purify compounds and was performed on Merck Kieselgel silica (Art. 9385) unless otherwise stated;

(iv) yields are given for illustration only and are not necessarily the maximum attainable; the structure of the end-products of the invention were generally confirmed by NMR and mass spectral techniques; proton magnetic resonance spectra is quoted and was generally determined in DMSO-$d_6$ unless otherwise stated using a Bruker DRX-300 spectrometer operating at a field strength of 300 MHz. Chemical shifts are reported in parts per million downfield from tetramethysilane as an internal standard (δ scale) and peak multiplicities are shown thus: s, singlet; d, doublet; AB or dd, doublet of doublets; dt, doublet of triplets; dm, doublet of multiplets; t, triplet, m, multiplet; br, broad; fast-atom bombardment (FAB) mass spectral data were generally obtained using a Platform spectrometer (supplied by Micromass) run in electrospray and, where appropriate, either positive ion data or negative ion data were collected or using Agilent 1100 series LC/MSD equipped with Sedex 75ELSD, run in atmospheric pressure chemical ionisation mode and, where appropriate, either positive ion data or negative ion data were collected; mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported;

(vi) each intermediate was purified to the standard required for the subsequent stage and was characterised in sufficient detail to confirm that the assigned structure was correct; purity was assessed by high pressure liquid chromatography, thin layer chromatography, or NMR and identity was determined by infra-red spectroscopy (IR), mass spectroscopy or NMR spectroscopy as appropriate;

(vii) the following abbreviations may be used:
EDC is 1-ethyl-3-(3-dimethyllaminopropyl)carbodiimide
DIEA is diisopropyl ethylamine;
HOBT is 1-hydroxybenzotriazole;
DMF is N,N-dimethylformamide;
SM is starting material;
DMSO is dimethylsulfoxide;
$CDCl_3$ is deuterated chloroform;
MS is mass spectroscopy;
EtOAc is ethyl acetate;
MeOH is methanol;
TFA is trifluoroacetic acid;
TFAA is trifluoroacetic anhydride;
HATU is N-[(dimethylamino)-1H,2,3-triazolo[4,5-b-]pyridin-1-ylmethylene]-N-methylmethanaminium hexafluorophosphate N-oxide;
EtOH is ethanol;
DCM is dichloromethane; and (viii) temperatures are quoted as ° C.

Example 1

Methyl 2-(6-{[(ethylamino)carbonyl]amino}pyridin-3-yl)-1,3-thiazole-5-carboxylate

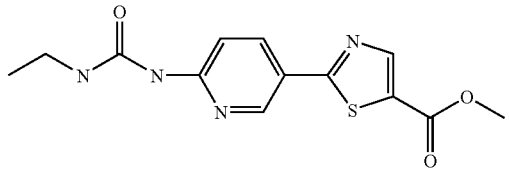

N-Ethyl-N'-[5-(4,4,5,5-tetramethyl-1,3,2-dioxaborolan-2-yl)pyridin-2-yl]urea (Intermediate 1, 0.20 g, 0.69 mmol), methyl 2-bromo-1,3-thiazole-5-carboxylate (0.152 g, 0.69 mmol), tetrakis triphenyl phosphine palladium (0.08 g, 0.069 mmol), and cesium carbonate (0.245 mg, 0.754 mmol) were taken in a microwave vial and degassed with argon. Then dioxane:water (4:1, 3 mL) was added to it and microwaved at 110° C. for half an hour. The reaction mixture was partitioned between water and EtOAc and layers separated. The organic layer was washed with sat. sodium bicarbonate solution, water, brine and dried over magnesium sulfate. The solvent was removed and the residue was purified by flash chromatography eluting with 2% MeOH in DCM to 3% MeOH in DCM. MS (ESP): 307 (M+H$^+$) for $C_{13}H_{14}N_4O_3S$; NMR: 1.09 (t, 3H), 3.16-3.22 (m, 2H), 3.86 (s, 3H), 7.60 (d, 1H), 7.79 (t, 1H), 8.27 (dd, 1H), 8.49 (s, 1H), 8.83 (s, 1H), 9.56 (s, 1H).

Examples 2-16

The following compounds were made by an analogous method to Example 1.

| Ex | Compound | Data | SM |
| --- | --- | --- | --- |
| 2 | Ethyl 2-(6-{[(ethylamino)carbonyl]amino}pyridin-3-yl)-1,3-thiazole-4-carboxylate | MS (ESP): 321 (M + H$^+$) for $C_{14}H_{16}N_4O_3S$; NMR: 1.09 (t, 3H), 1.31 (t, 3H), 3.14-3.22 (m, 2H), 4.32 (q, 2H), 7.60 (d, 1H), 7.80 (brs, 1H), 8.21 (dd, 1H), 8.54 (s, 1H), 8.77 (s, 1H), 9.52 (s, 1H) | Intermediate 1 and ethyl 2-bromo-1,3-thiazole-4-carboxylate |
| 3 | Ethyl 6'-{[(ethylamino)carbonyl]amino}-3,3'-bipyridine-5-carboxylate | MS (ES): 315 (M + H$^+$) for $C_{16}H_{18}N_4O_3$; NMR: 1.09 (t, 3H), 1.35 (t, 3H), 3.14-3.25 (m, 2H), 4.37 (q, 2H), 7.53 (d, 1H), 7.96 (t, 1H), 8.15 (dd, 1H), 8.47 (s, 1H), 8.64 (s, 1H), 9.04 (s, 1H), 9.13 (s, 1H), 9.37 (s, 1H) | Intermediate 1 and ethyl 5-bromonicotinate |
| 4 | Ethyl 2-(6-{[(ethylamino)carbonyl]amino}pyridin-3-yl)-1,3-benzothiazole-7-carboxylate | MS (ES): 371 (M + H$^+$) for $C_{18}H_{18}N_4O_3S$; NMR: 1.10 (t, 3H), 1.40 (t, 3H), 3.20 (m, 2H), 4.44 (q, 2H), 7.68 (q, 2H), 7.82 (t, 1H), 8.10 (dd, 1H), 8.30 (d, 1H), 8.39 (dd, 1H), 8.94 (d, 1H), 9.59 (s, 1H) | Intermediate 1 and ethyl 2-bromo-1,3-benzothiazole-7-carboxylate (U.S. Pat. No. 5,770,758) |
| 5 | Methyl 6'-{[(ethylamino)carbonyl]amino}-2,3'-bipyridine-5-carboxylate | MS (ES): 301 (M + H$^+$) for $C_{15}H_{16}N_4O_3$; NMR: 1.10 (t, 3H), 3.14-3.22 (m, 2H), 3.92 (s, 3H), 7.52 (d, 1H), 7.75 (dd, 1H), 7.98 | Intermediate 1 and methyl 6-bromonicotinate |

| Ex | Compound | Data | SM |
|---|---|---|---|
| | (structure: ethyl-NH-C(O)-NH-pyridine-pyridine-C(O)-O-methyl) | (brs, 1H), 8.28 (s, 1H), 8.39 (dd, 1H), 8.83 (d, 1H), 8.93 (s, 1H), 9.42 (s, 1H) | |
| 6 | Methyl 3-(6-{[(ethylamino)carbonyl]amino}pyridin-3-yl)benzoate | MS (ES): 300 (M + H$^+$) for $C_{16}H_{17}N_3O_3$; NMR: 1.09 (t, 3H), 3.15-3.24 (m, 2H), 3.88 (s, 3H), 7.49 (d, 1H), 7.61 (t, 1H), 7.92-8.03 (m, 3H), 8.05 (dd, 1H), 8.16 (s, 1H), 8.53 (d, 1H), 9.32 (s, 1H) | Intermediate 1 and methyl 3-bromobenzoate |
| 7 | Methyl 4-(6-{[(ethylamino)carbonyl]amino}pyridin-3-yl)benzoate | MS (ES): 300 (M + H$^+$) for $C_{16}H_{17}N_3O_3$; NMR: 1.09 (t, 3H), 3.15-3.21 (m, 2H), 3.86 (s, 3H), 7.50 (d, 1H), 7.83 (d, 2H), 7.96 (t, 1H), 8.01 (m, 2H), 8.09 (dd, 1H), 8.59 (d, 1H), 9.34 (s, 1H) | Intermediate 1 and methyl 4-bromobenzoate |
| 8 | Isopropyl 2-(6-{[(ethylamino)carbonyl]amino}pyridin-3-yl)-4-[(methylamino)carbonyl]-1,3-thiazole-5-carboxylate | MS (ESP): 392 (M + H$^+$) for $C_{17}H_{21}N_5O_4S$; NMR: 1.08 (t, 3H), 1.27 (d, 6H), 2.76 (d, 3H), 3.14-3.22 (m, 2H), 5.04-5.11 (m, 1H), 7.62 (d, 1H), 7.73 (t, 1H), 8.26 (dd, 1H), 8.54-8.56 (m, 1H), 8.82 (d, 1H), 9.58 (s, 1H) | Intermediate 1 and Intermediate 10 |
| 9 | Ethyl 4-[(cyclopropylamino)carbonyl]-2-(6-{[(ethylamino)carbonyl]amino}pyridin-3-yl)-1,3-thiazole-5-carboxylate | MS (ESP): 404 (M + H$^+$) for $C_{18}H_{21}N_5O_4S$; NMR: 0.50-0.52 (m, 2H), 0.69-0.71 (m, 2H), 1.08 (t, 3H), 1.27 (t, 3H), 2.78-2.82 (m, 1H), 3.18-3.22 (m, 2H), 4.27 (q, 2H), 7.62 (d, 1H), 7.74 (t, 1H), 8.27 (dd, 1H), 8.65 (d, 1H), 8.82 (s, 1H), 9.58 (s, 1H) | Intermediate 1 and Intermediate 4 |
| 10 | Ethyl 4-[(butylamino)carbonyl]-2-(6-{[(ethylamino)carbonyl]amino}pyridin-3-yl)-1,3-thiazole-5-carboxylate | MS (ESP): 420 (M + H$^+$) for $C_{19}H_{25}N_5O_4S$; NMR: 0.90 (t, 3H), 1.09 (t, 3H), 1.26 (t, 3H), 1.29-1.39 (m, 2H), 1.48-1.53 (m, 2H), 3.16-3.22 (m, 4H), 4.27 (q, 2H), 7.62 (d, 1H), 7.74 (s, 1H), 8.27 (dd, 1H), 8.59 (t, 1H), 8.83 (s, 1H), 9.58 (s, 1H) | Intermediate 1 and Intermediate 5 |

-continued

| Ex | Compound | Data | SM |
|---|---|---|---|
| | 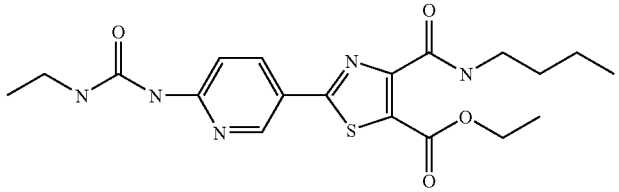 | | |
| 11 | Methyl 4-acetyl-2-(6-{[(ethylamino)carbonyl]amino}pyridin-3-yl)-1,3-thiazole-5-carboxylate | MS (ESP): 349 (M + H$^+$) for C$_{15}$H$_{16}$N$_4$O$_4$S | Intermediate 1 and Intermediate 15 |
| | 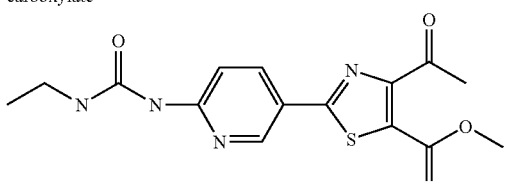 | | |
| 12 | Methyl 6-(6-{[(ethylamino)carbonyl]amino}pyridin-3-yl)imidazo[1,2-a]pyridine-2-carboxylate | MS (ESP): 340 (M + H$^+$) for C$_{17}$H$_{17}$N$_5$O$_3$; NMR: 1.09 (t, 3H), 3.16-3.22 (m, 2H), 3.84 (s, 3H), 7.53 (d, 1H), 7.71 (s, 2H), 7.90 (s, 1H), 8.03 (dd, 1H), 8.50 (s, 1H), 8.54 (s, 1H), 8.91 (s, 1H), 9.33 (s, 1H) | Intermediate 1 and methyl 6-bromoimidazo[1,2-a]pyridine-2-carboxylate |
| | 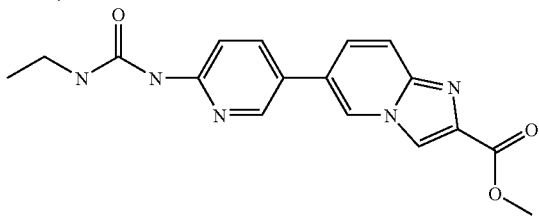 | | |
| 13 | Methyl 3-(2-{[(ethylamino)carbonyl]amino}pyrimidin-5-yl)benzoate | MS (ES): 301 (M + H$^+$) for C$_{15}$H$_{16}$N$_4$O$_3$; NMR: 1.12 (t, 3H), 3.22-3.30 (m, 2H), 3.88 (s, 3H), 7.65 (t, 1H), 7.97-8.02 (m, 2H), 8.23 (s, 1H), 8.94 (s, 2H), 8.98 (t, 1H), 9.92 (s, 1H) | Intermediate 2 and methyl 3-bromobenzoate |
| | 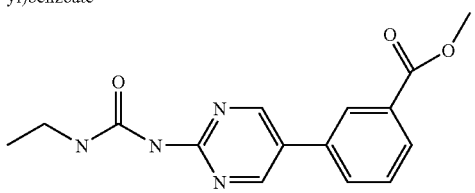 | | |
| 14 | Methyl 2-(2-{[(ethylamino)carbonyl]amino}pyrimidin-5-yl)-1,3-thiazole-5-carboxylate | MS (ESP): 308 (M + H$^+$) for C$_{12}$H$_{13}$N$_5$O$_3$S; NMR: 1.12 (t, 3H), 3.24-3.29 (m, 2H), 3.87 (s, 3H), 8.55 (s, 1H), 8.89 (t, 1H), 9.14 (s, 2H), 10.27 (s, 1H) | Intermediate 2 and methyl 2-bromo-1,3-thiazole-5-carboxylate |
| | 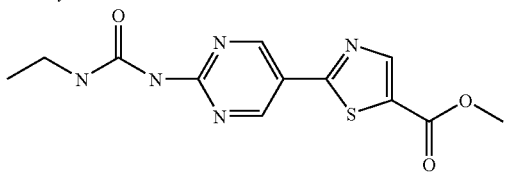 | | |
| 15 | Ethyl 3-(6-{[(ethylamino)carbonyl]amino}pyridin-2-yl)benzoate | MS (ESP): 314 (M + H$^+$) for C$_{17}$H$_{19}$N$_3$O$_3$; NMR: 1.13 (t, 3H), 1.34 (t, 3H), 3.16-3.23 (m, 2H), 4.35 (q, 2H), 7.39 (d, 1H), 7.54 (d, | Intermediate 3 and [3-(ethoxycarbonyl)phenyl]boronic acid |

-continued

| Ex | Compound | Data | SM |
|---|---|---|---|
| 16 | Ethyl 4-(6-{[(ethylamino)carbonyl]amino}pyridin-2-yl)benzoate | 1H), 7.65 (t, 1H), 7.79 (t, 1H), 8.01 (d, 1H), 8.16 (brs, 1H), 8.22 (d, 1H), 8.53 (s, 1H), 9.35 (s, 1H) | |
| | | MS (ESP): 314 (M + H⁺) for $C_{17}H_{19}N_3O_3$; NMR: 1.12 (t, 3H), 1.34 (t, 3H), 3.18-3.24 (m, 2H), 4.33 (q, 2H), 7.42 (d, 1H), 7.56 (d, 1H), 7.80 (t, 1H), 8.05-8.12 (m, 5H), 9.34 (s, 1H) | Intermediate 3 and [4-(ethoxycarbonyl)-phenyl]boronic acid |

Example 17

2-(6-{[(Ethylamino)carbonyl]amino}pyridin-3-yl)-1,3-thiazole-5-carboxylic acid

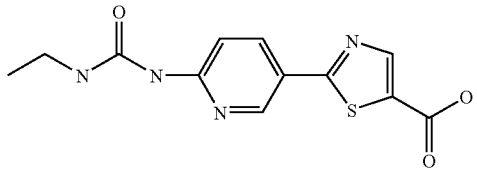

Methyl-2-(6-{[(ethylamino)carbonyl]amino}pyridin-3-yl)-1,3-thiazole-5-carboxylate (Example 1, 0.185 g, 0.60 mmol) was taken in MeOH (6 mL) and 2N LiOH (1 mL) was added to it. The resulting mixture was stirred at 45° C. for two hours. The solvent was removed and the aqueous was diluted with water and acidified with 1N HCl. The precipitated product was collected by filtration and washed with water and dried (0.17 g). MS (ESP): 293 (M+H⁺) for $C_{12}H_{12}N_4O_3S$; NMR: 1.09 (t, 3H), 3.16-3.22 (m, 2H), 7.60 (d, 1H), 7.81 (t, 1H), 8.26 (dd, 1H), 8.38 (s, 1H), 8.81 (s, 1H), 9.54 (s, 1H), 13.54 (brs, 1H).

Examples 18-33

The following compounds were made by an analogous method to Example 17.

| Ex | Compound | Data | SM |
|---|---|---|---|
| 18 | 2-(6-{[(Ethylamino)carbonyl]amino}pyridin-3-yl)-1,3-thiazole-4-carboxylic acid | MS (ESP): 293 (M + H⁺) for $C_{12}H_{12}N_4O_3S$; NMR: 1.09 (t, 3H), 3.14-3.23 (m, 2H), 7.59 (d, 1H), 7.80 (t, 1H), 8.21 (dd, 1H), 8.46 (s, 1H), 8.77 (s, 1H), 9.51 (s, 1H), 13.13 (brs, 1H) | Example 2 |
| 19 | 6'-{[(Ethylamino)carbonyl]amino}-3,3'-bipyridine-5-carboxylic acid | MS (ES): 287 (M + H⁺) for $C_{14}H_{14}N_4O_3$; NMR: 1.09 (t, 3H), 3.15-3.23 (m, 2H), 7.53 (d, 1H), 7.95 (t, | Example 3 |

| Ex | Compound | Data | SM |
|---|---|---|---|
| | 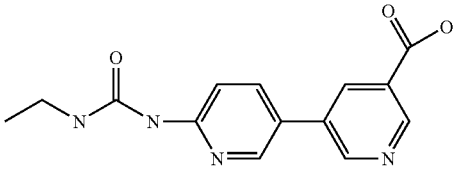 | 1H), 8.14 (dd, 1H), 8.45 (t, 1H), 8.63 (s, 1H), 9.02 (s, 1H), 9.11 (s, 1H), 9.35 (s, 1H), 13.51 (brs, 1H) | |
| 20 | 2-(6-{[(Ethylamino)carbonyl]amino}-pyridin-3-yl)-1,3-benzothiazole-7-carboxylic acid 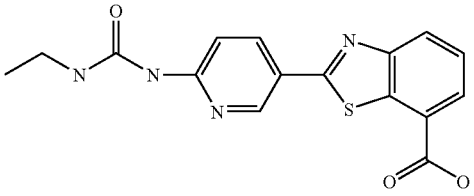 | MS (ES): 343 (M + H$^+$) for C$_{16}$H$_{14}$N$_4$O$_3$S; NMR: 1.09 (t, 3H), 3.18-3.23 (m, 2H), 7.48 (t, 1H), 7.58 (d, 1H), 7.87-7.91 (m, 2H), 7.80 (d, 1H), 8.31 (dd, 1H), 8.86 (d, 1H), 9.52 (s, 1H) | Example 4 |
| 21 | 6'-{[(Ethylamino)carbonyl]amino}-2,3'-bipyridine-5-carboxylic acid 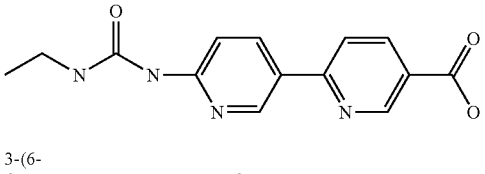 | MS (ES): 287 (M + H$^+$) for C$_{14}$H$_{14}$N$_4$O$_3$; NMR: 1.10 (t, 3H), 3.15-3.24 (m, 2H), 7.52 (t, 1H), 7.73 (d, 1H), 7.99 (brs, 1H), 8.27 (s, 1H), 8.39 (dd, 1H), 8.81 (d, 1H), 8.93 (d, 1H), 9.41 (s, 1H) | Example 5 |
| 22 | 3-(6-{[(Ethylamino)carbonyl]amino}-pyridin-3-yl)benzoic acid 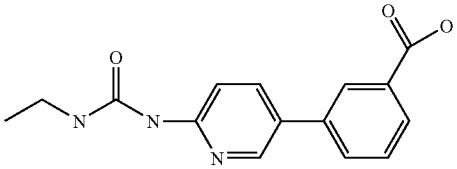 | MS (ES): 286 (M + H$^+$) for C$_{15}$H$_{15}$N$_3$O$_3$; NMR: 1.09 (t, 3H), 3.16-3.22 (m, 2H), 7.48-7.56 (m, 2H), 7.84-7.91 (m, 2H), 8.02-8.05 (m, 2H), 8.15 (s, 1H), 8.53 (s, 1H), 9.33 (s, 1H) | Example 6 |
| 23 | 4-(6-{[(Ethylamino)carbonyl]amino}-pyridin-3-yl)benzoic acid 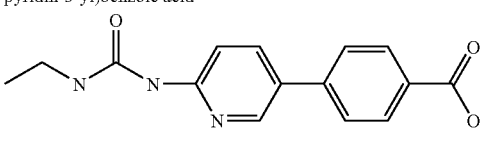 | MS (ES): 286 (M + H$^+$) for C$_{15}$H$_{15}$N$_3$O$_3$; NMR: 1.09 (t, 3H), 3.15-3.21 (m, 2H), 3.86 (s, 3H), 7.50 (d, 1H), 7.80 (d, 2H), 7.98 (t, 1H), 7.99 (d 2H), 8.07 (dd, 1H), 8.59 (d, 1H), 9.33 (s, 1H), 12.98 (brs, 1H) | Example 7 |
| 24 | 2-(6-{[(Ethylamino)carbonyl]amino}-pyridin-3-yl)-4-[(methylamino)carbonyl]-1,3-thiazole-5-carboxylic acid 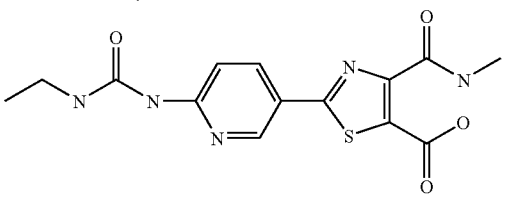 | MS (ESP): 350 (M + H$^+$) for C$_{14}$H$_{15}$N$_5$O$_4$S; NMR: 1.08 (t, 3H), 2.92 (d, 3H), 3.13-3.21 (m, 2H), 7.64 (d, 1H), 7.70 (t, 1H), 8.36 (dd, 1H), 8.98 (d, 1H), 9.61 (s, 1H), 9.78 (s, 1H) | Example 8 |
| 25 | 4-[(Cyclopropylamino)carbonyl]-2-(6-{[(ethylamino)carbonyl]amino}-pyridin-3-yl)-1,3-thiazole-5- | MS (ESP): 376 (M + H$^+$) for C$_{16}$H$_{17}$N$_5$O$_4$S; NMR: 0.60-0.79 (m, 4H), 1.09 (t, 3H), 2.90-2.92 (m, 1H), 3.14-3.20 (m, 2H), 7.59 (d, 1H), 7.78 | Example 9 |

| Ex | Compound | Data | SM |
|---|---|---|---|
| | carboxylic acid 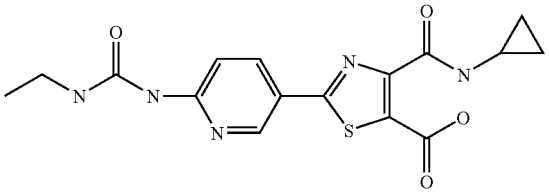 | (s, 1H), 8.31 (d, 1H), 8.91 (s, 1H), 9.56 (s, 1H) | |
| 26 | 4-[(Butylamino)carbonyl]-2-(6-{[(ethylamino)carbonyl]amino}-pyridin-3-yl)-1,3-thiazole-5-carboxylic acid 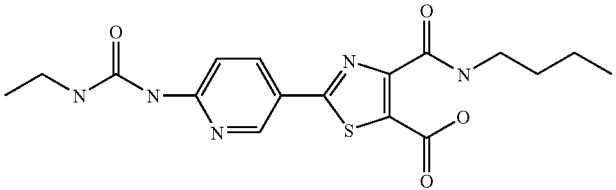 | MS (ESP): 392 (M + H$^+$) for C$_{17}$H$_{21}$N$_5$O$_4$S; NMR: 0.91 (t, 3H), 1.09 (t, 3H), 1.30-1.38 (m, 2H), 1.55-1.62 (m, 2H), 3.16-3.23 (m, 2H), 3.36-3.42 (m, 2H), 7.64 (d, 1H), 7.73 (brs, 1H), 8.38 (dd, 1H), 9.01 (d, 1H), 9.61 (s, 1H), 9.82 (brs, 1H) | Example 10 |
| 27 | 4-Acetyl-2-(6-{[(ethylamino)carbonyl]amino}-pyridin-3-yl)-1,3-thiazole-5-carboxylic acid 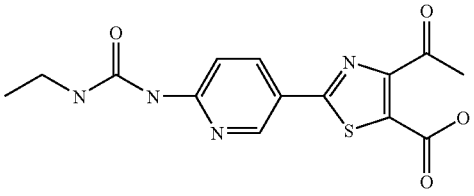 | MS (ESP): 335 (M + H$^+$) for C$_{14}$H$_{14}$N$_4$O$_4$S; NMR: 1.09 (t, 3H), 2.61 (s, 3H), 3.15-3.23 (m, 2H), 7.62 (d, 1H), 7.76 (brs, 1H), 8.25 (dd, 1H), 8.82 (d, 1H), 9.58 (s, 1H) | Example 11 |
| 28 | 6-(6-{[(Ethylamino)carbonyl]amino}-pyridin-3-yl)imidazo[1,2-a]pyridine-2-carboxylic acid 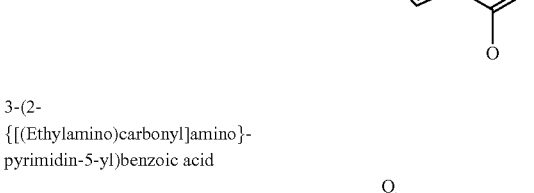 | MS (ESP): 326 (M + H$^+$) for C$_{16}$H$_{15}$N$_5$O$_3$; NMR: 1.09 (t, 3H), 3.16-3.22 (m, 2H), 7.53 (d, 1H), 7.69 (s, 2H), 7.90 (brs, 1H), 8.123 (d, 1H), 8.42 (s, 1H), 8.53 (s, 1H), 8.91 (s, 1H), 9.33 (s, 1H) | Example 12 |
| 29 | 3-(2-{[(Ethylamino)carbonyl]amino}-pyrimidin-5-yl)benzoic acid 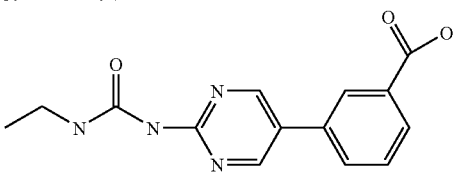 | MS (ES): 287 (M + H$^+$) for C$_{14}$H$_{14}$N$_4$O$_3$; NMR: 1.12 (t, 3H), 3.20-3.28 (m, 2H), 7.62 (t, 1H), 7.97 (d, 2H), 8.21 (s, 1H), 8.94 (s, 2H), 8.99 (t, 1H), 9.92 (s, 1H), 13.14 9 s, 1H) | Example 13 |
| 30 | 2-(2-{[(Ethylamino)carbonyl]amino}-pyrimidin-5-yl)-1,3-thiazole-5- | MS (ESP): 294 (M + H$^+$) for C$_{11}$H$_{11}$N$_5$O$_3$S; NMR: 1.12 (t, 3H), 3.24-3.29 (m, 2H), 8.43 (s, 1H), 8.90 | Example 14 |

-continued

| Ex | Compound | Data | SM |
|---|---|---|---|
| | carboxylic acid 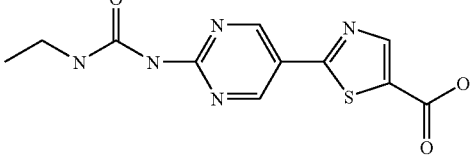 | (s, 1H), 9.13 (s, 2H), 10.24 (s, 1H), 13.70 (s, 1H) | |
| 31 | 3-(6-{[(Ethylamino)carbonyl]amino}-pyridin-2-yl)benzoic acid 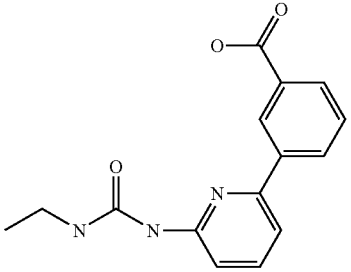 | MS (ESP): 286 (M + H$^+$) for C$_{15}$H$_{15}$N$_3$O$_3$; NMR: 1.12 (t, 3H), 3.16-3.22 (m, 2H), 7.39 (d, 1H), 7.54 (d, 1H), 7.62 (t, 1H), 7.78 (t, 1H), 7.99 (d, 1H), 8.11 (brs, 1H), 8.19 (d, 1H), 8.56 (s, 1H), 9.33 (s, 1H), 13.01 (brs, 1H) | Example 15 |
| 32 | 4-(6-{[(Ethylamino)carbonyl]amino}-pyridin-2-yl)benzoic acid 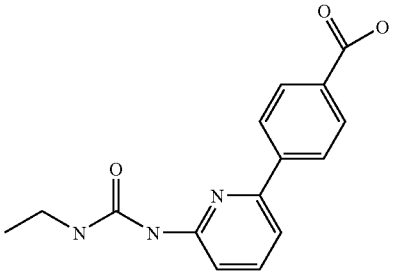 | MS (ESP): 286 (M + H$^+$) for C$_{15}$H$_{15}$N$_3$O$_3$; NMR: 1.12 (t, 3H), 3.18-3.24 (m, 2H), 7.41 (d, 1H), 7.56 (d, 1H), 7.80 (t, 1H), 8.03-8.09 (m, 5H), 9.33 (s, 1H), 13.08 (brs, 1H) | Example 16 |
| 33 | 4-(2-{[(Ethylamino)carbonyl]amino}-1,3-thiazol-4-yl)benzoic acid 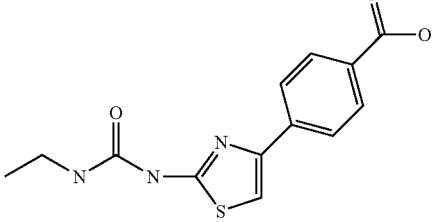 | MS (ESP): 292 (M + H$^+$) for C$_{13}$H$_{13}$N$_3$O$_3$S; NMR: 1.06 (t, 3H), 3.12-3.18 (m, 2H), 6.48 (s, 1H), 7.63 (s, 1H), 7.96 (s, 4H), 10.65 (s, 1H), 12.90 (s, 1H) | Example 41 |

Examples 34-36

The following Examples were made by the procedure of Intermediate 18.

| Ex | Compound | Data | SM |
|---|---|---|---|
| 34 | 2-(6-{[(Ethylamino)carbonyl]-amino}pyridin-3-yl)-N-methoxy-1,3-thiazole-5-carboxamide | MS (ESP): 322 (M + H$^+$) for C$_{13}$H$_{15}$N$_5$O$_3$S; NMR: 1.09 (t, 3H), 3.16-3.22 (m, 2H), 3.72 (s, 3H), 7.58 (d, 1H), 7.82 (brs, 1H), 8.23 (dd, 1H), 8.30 (brs, 1H), 8.79 (s, 1H), 9.53 (s, 1H), 12.01 (s, 1H) | Example 17 and N-methoxy amine hydrochloride |
| 35 | N$^4$-Cyclopropyl-2-(6-{[(ethylamino)carbonyl]-amino}pyridin-3-yl)-N$^5$-methoxy-1,3-thiazole-4,5-dicarboxamide | MS (ESP): 405 (M + H$^+$) for C$_{17}$H$_{20}$N$_6$O$_4$S; NMR: 0.74-0.79 (m, 4 H), 1.08 (t, 3H), 2.91-2.93 (m, 1H), 3.14-3.24 (m, 2H), 3.76 (s, 3H), 7.60 (d, 1H), 7.76 (brs, 1H), 8.37 (dd, 1H), 9.00 (s, 1H), 9.14 (s, 1H), 9.57 (s, 1H), 13.83 (s, 1H) | Example 25 and N-methoxy amine hydrochloride |
| 36 | N$^4$-Butyl-2-(6-{[(ethylamino)carbonyl]-amino}pyridin-3-yl)-N$^5$-methoxy-1,3-thiazole-4,5-dicarboxamide | MS (ESP): 421 (M + H$^+$) for C$_{18}$H$_{24}$N$_6$O$_4$S; NMR: 0.91 (t, 3H), 1.09 (t, 3H), 1.30-1.37 (m, 2H), 1.52-1.59 (m, 2H), 3.16-3.23 (m, 2H), 3.28-3.41 (m, 2H), 3.75 (s, 3H), 7.62 (d, 1H), 7.76 (t, 1H), 8.36 (dd, 1H), 8.99 (d, 1H), 8.34 (t, 1H), 9.58 (s, 1H), 13.97 (s, 1H) | Example 26 and N-methoxy amine hydrochloride |

Example 37

2-(6-{[(Ethylamino)carbonyl]amino}pyridin-3-yl)-1,3-thiazole-5-carboxamide

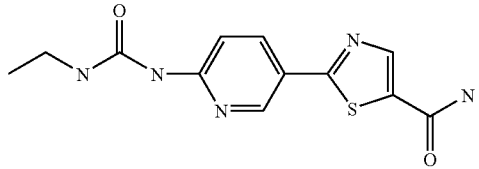

2-(6-{[(Ethylamino)carbonyl]amino}pyridin-3-yl)-N-(1-methyl-1-phenylethyl)-1,3-thiazole-5-carboxamide (Intermediate 18, 53 mg, 0.129 mmol) was dissolved in TFA (1 mL) and the solution was stirred overnight. TFA was removed under reduced pressure and the crude was partitioned between aqueous sodium bicarbonate and EtOAc. The layers separated and the organic layer was washed with water and brine. During the work up process the product precipitated which was collected by filtration. Washed with water and EtOAc and dried (0.020 g). MS (ESP): 292 (M+H$^+$) for C$_{12}$H$_{13}$N$_5$O$_2$S; NMR: 1.09 (t, 3H), 3.16-3.22 (m, 2H), 7.56 (d, 1H), 7.65 (brs, 1H), 7.83 (brs, 1H), 8.15-8.23 (m, 2H), 8.40 (s, 1H), 8.77 (s, 1H), 9.51 (s, 1H).

Examples 38-40

The following compounds were made by an analogous method to Example 37.

| Ex | Compound | Data | SM |
|---|---|---|---|
| 38 | $N^4$-Cyclopropyl-2-(6-{[(ethylamino)carbonyl]amino}pyridin-3-yl)-1,3-thiazole-4,5-dicarboxamide | MS (ESP): 375 (M + H$^+$) for $C_{16}H_{18}N_6O_3S$; NMR: 0.73-0.79 (m, 4H), 1.09 (t, 3H), 2.89-2.93 (m, 1H), 3.15-3.24 (m, 2H), 7.59 (d, 1H), 7.80 (t, 1H), 8.07 (s, 1H), 8.36 (dd, 1H), 8.98 (d, 1H), 9.06 (s, 1H), 9.55 (s, 1H), 10.53 (s, 1H) | Intermediate 19 |
| 39 | $N^4$-Butyl-2-(6-{[(ethylamino)carbonyl]amino}pyridin-3-yl)-1,3-thiazole-4,5-dicarboxamide | MS (ESP): 391 (M + H$^+$) for $C_{17}H_{22}N_6O_3S$; NMR: 0.91 (t, 3H), 1.09 (t, 3H), 1.30-1.37 (m, 2H), 1.52-1.58 (m, 2H), 3.16-3.23 (m, 2H), 3.28-3.41 (m, 2H), 7.60 (d, 1H), 7.79 (t, 1H), 8.05 (brs, 1H), 8.35 (dd, 1H), 8.97 (s, 1H), 9.22 (brs, 1H), 9.56 (brs, 1H), 10.63 (s, 1H) | Intermediate 20 |
| 40 | 2-(6-{[(Ethylamino)carbonyl]amino}pyridin-3-yl)-1,3-benzothiazole-7-carboxamide | MS (ES): 342 (M + H$^+$) for $C_{16}H_{15}N_5O_2S$; NMR: 1.10 (t, 3H), 3.16-3.23 (m, 2H), 7.60-7.66 (m, 2H), 7.82 (brs, 2H), 8.08 (d, 1H), 8.17 (d, 1H), 8.38 (dd, 1H), 8.41 (s, 1H), 8.92 (d, 1H), 9.56 (s, 1H) | Intermediate 21 |

Example 41

Methyl 4-(2-{[(ethylamino)carbonyl]amino}-1,3-thiazol-4-yl)benzoate

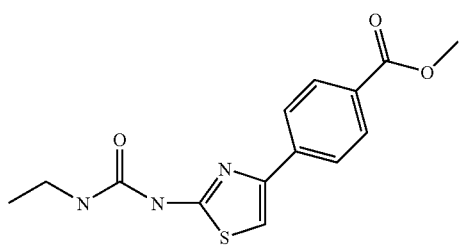

To a solution of methyl 4-(2-amino-1,3-thiazol-4-yl)benzoate (Intermediate 11; 150 mg, 0.64 mmol) in NMP (3 mL), ethyl isocyanate (90 μl, 1.14 mmol) was added. The solution was heated at 110° C. for one hour in a microwave. The crude was partitioned between water and EtOAc. The organic layer was washed with NaHCO$_3$ solution, water and brine. It was dried over magnesium sulfate and concentrated. The residue was purified by flash chromatography (2% MeOH in DCM) to give the desired product (79 mg). MS (ESP): 306 (M+H$^+$) for $C_{14}H_{15}N_3O_3S$; NMR: 1.06 (t, 3H), 3.12-3.16 (m, 2H), 3.85 (s, 3H), 6.48 (s, 1H), 7.66 (s, 1H), 7.98 (s, 4H), 10.65 (s, 1H).

Example 42

Ethyl 6-(6-(3-ethylureido)pyridin-3-yl)-1-(2-methoxyethyl)-4-oxo-1,4-dihydroquinoline-3-carboxylate

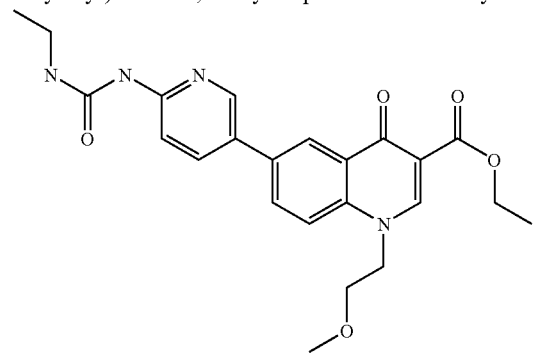

A mixture of N-ethyl-N'-(5-(4,4,5,5-tetramethyl-1,3,2-dioxaborolan-2-yl)pyridin-2-yl)urea (Intermediate 1, 80 mg, 0.27 mmol), ethyl 6-iodo-1-(2-methoxyethyl)-4-oxo-1,4-dihydroquinoline-3-carboxylate (WO2006010733, 100 mg, 0.25 mmol), cesium carbonate (90 mg, 0.27 mmol), and Tetrakisphenylphosphine palladium (28.9 mg, 0.02 mmol) in dioxane (4 mL) and water (1 mL) was degassed with nitrogen for 30 minutes. The reaction mixture was then heated in a microwave for 1 h at 110° C. The reaction mixture was cooled to room temperature and filtered, then placed on high vacuum to remove residual solvent (59 mg). MS (ESP): 439 (M+H$^+$) for $C_{23}H_{26}N_4O_5$; NMR: 9.34 (s, 1H), 8.61 (m, 2H), 8.45 (m, 1H), 8.10 (m, 1H), 8.09 (m, 2H), 7.54 (m, 1H), 4.62 (m, 2H), 4.25 (m, 2H), 3.71 (m, 2H), 3.57 (s, 3H), 3.21 (m, 2H), 1.30 (t, J=7 Hz, 3H), 1.11 (t, J=8 Hz, 3H).

Examples 43-45

The following Examples were synthesized according to the procedure described for Example 42 using the starting materials as stated below.

| Ex | Compound | Data | SM |
|----|----------|------|-----|
| 43 | Ethyl 1-butyl-6-(6-(3-ethylureido)pyridin-3-yl)-4-oxo-1,4-dihydroquinoline-3-carboxylate 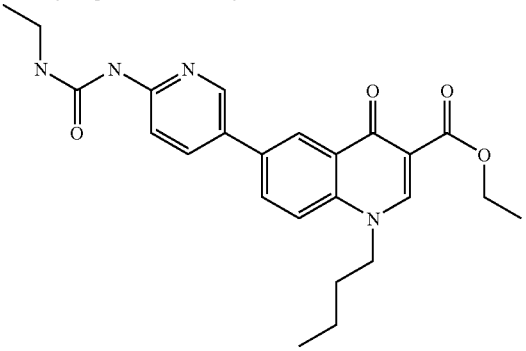 | MS (ES): 437 (M + H$^+$) for $C_{24}H_{28}N_4O_4$; NMR: 0.92 (t, J = 5 Hz, 3H), 1.11 (t, J = 7 Hz, 3H), 1.30-1.45 (m, 5H), 1.76 (m, 2H), 3.21 (m, 2H), 4.23 (m, 2H), 4.42 (m, 2H), 7.52 (m, 1H), 7.90 (m, 1H), 8.04 (m, 1H), 8.11 (m, 2H), 8.44 (m, 1H), 8.60 (s, 1H), 8.69 (s, 1H), 9.34 (s, 1H). | Intermediate 1 and Intermediate 22 |
| 44 | Ethyl 6-(6-(3-ethylureido)pyridin-3-yl)-1-(2-morpholinoethyl)-4-oxo-1,4-dihydroquinoline-3-carboxylate 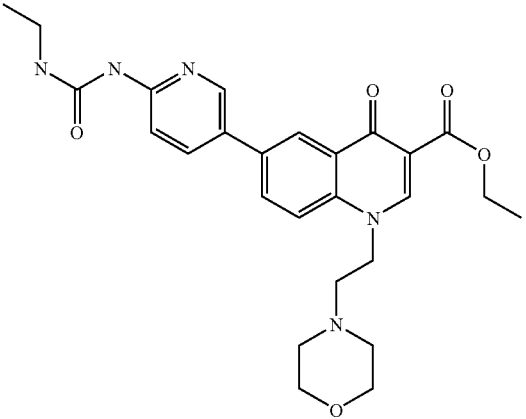 | MS (ES): 494 (M + H$^+$) for $C_{26}H_{31}N_5O_5$; NMR: 1.11 (t, J = 7 Hz, 3H), 1.30 (t, J = 7 Hz, 3H), 2.47 (m, 4H), 2.66 (m, 2H), 3.24 (m, 2H), 3.52 (m, 4H), 4.23 (m, 2H), 4.50 (m, 2H), 7.40 (s, 1H), 7.54 (m, 1H), 7.95 (m, 1H), 8.12 (m, 2H), 8.45 (m, 1H), 8.60 (m, 2H), 9.34 (s, 1H). | Intermediate 1 and Intermediate 24 |
| 45 | Ethyl 1-(2,2-difluoroethyl)-6-(6-(3-ethylureido)pyridin-3-yl)-4-oxo-1,4-dihydroquinoline-3-carboxylate 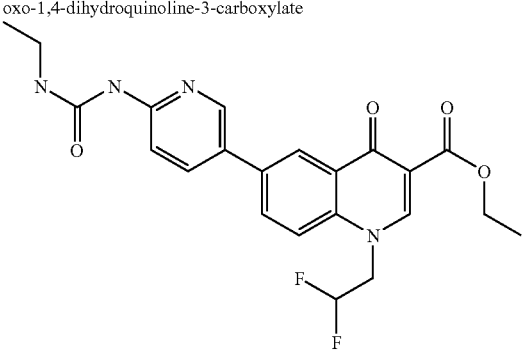 | MS (ES): 445 (M + H$^+$) for C22H22F2N4O4; NMR: 1.11 (t, J = 8 Hz, 3H), 1.30 (t, J = 8 Hz, 3H), 3.21 (m, 2H), 4.27 (m, 2H), 5.03 (m, 2H), 6.54 (t, J = 20 Hz, 1H), 7.54 (m, 1H), 8.02 (m, 2H), 8.14 (m, 1H), 8.45 (m,, 1H), 8.70 (s, 1H), 9.35 (s, 1H). | Intermediate 1 and Intermediate 25 |

Example 46

6-(6-(3-Ethylureido)pyridin-3-yl)-1-(2-methoxyethyl)-4-oxo-1,4-dihydroquinoline-3-carboxylic acid

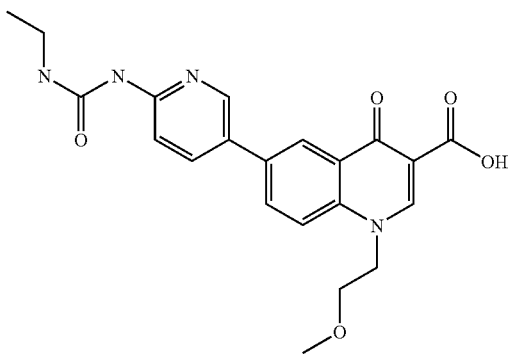

A suspension of ethyl 6-(6-(3-ethylureido)pyridin-3-yl)-1-(2-methoxyethyl)-4-oxo-1,4-dihydroquinoline-3-carboxylate (Example 42, 59 mg, 0.13 mmol) and sodium hydroxide (0.202 mL, 0.40 mmol) in tetrahydrofuran (1 mL) was heated to 60° C. After 2 h, the reaction was not yet complete. Ethanol (2 mL) was added and the reaction was heated for another 1 h, then cooled to room temperature and concentrated under reduced pressure. The resulting solid was dissolved in water and acidified to pH 4 with 10% HCl. The solid that formed was collected by filtration and placed under high vacuum to remove residual water. MS (ESP): 411 (M+H$^+$) for $C_{21}H_{22}N_4O_5$; NMR: 1.11 (t, J=6 Hz, 3H), 3.20 (m, 2H), 3.23 (s, 3H), 3.74 (m, 2H), 4.83 (m, 2H), 7.50 (m, 1H), 8.01 (br s, 1H), 8.21 (m, 1H), 8.31 (m, 1H), 8.58 (m, 1H), 8.69 (m, 1H), 8.94 (s, 1H), 9.38 (s, 1H), 15.20 (s, 1H).

Examples 47-49

The following compounds were synthesized according to the procedure described in Example 46 using the indicated starting material.

| Ex | Compound | Data | SM |
|----|----------|------|-----|
| 47 | 1-Butyl-6-(6-(3-ethylureido)pyridin-3-yl)-4-oxo-1,4-dihydroquinoline-3-carboxylic acid | MS (ES): 409 (M + H$^+$) for $C_{22}H_{24}N_4O_4$; NMR: 0.83 (m, 3H), 1.11 (m, 3H), 1.27 (m, 2H), 1.41 (m, 2H), 3.20 (m, 2H), 3.65 (m, 2H), 7.52 (m, 2H), 8.05 (m, 3H), 8.57 (m, 1H), 9.33 (s, 1H), 13.43 (s, 1H). | Example 43 |
| 48 | 6-(6-(3-ethylureido)pyridin-3-yl)-1-(2-morpholinoethyl)-4-oxo-1,4-dihydroquinoline-3-carboxylic acid | MS (ES): 466 (M + H$^+$) for $C_{24}H_{27}N_5O_5$; NMR: 1.11 (t, J = 7 Hz, 3H), 3.21 (m, 4H), 3.67 (m, 2H), 3.79 (m, 2H), 4.02 (m, 2H), 5.05 (m, 2H), 7.56 (m, 1H), 8.04 (m, 1H), 8.20 (m, 1H), 8.32 (m,, 2H), 8.59 (s, 1H), 8.69 (s, 1H), 9.15 (s, 1H), 9.43 (s, 1H). | Example 44 |

| Ex | Compound | Data | SM |
|---|---|---|---|
| 49 | 1-(2,2-difluoroethyl)-6-(6-(3-ethylureido)pyridin-3-yl)-4-oxo-1,4-dihydroquinoline-3-carboxylic acid 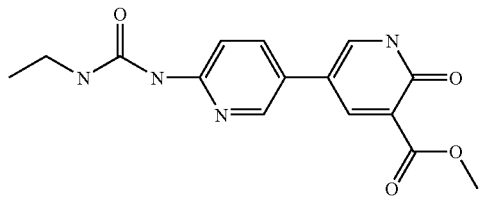 | MS (ES): 417 (M + H+) for $C_{20}H_{18}F_2N_4O_4$; NMR: 1.11 (t, J = 7 Hz, 3H), 3.21 (m, 2H), 4.07 (m, 2H), 6.16 (m, J = 20 Hz, 1H), 7.56 (m, 2H), 8.10 (m, 2H), 8.17 (m, 1H), 8.58 (m, 1H), 9.34 (s, 1H). | Example 45 |

Example 50

Methyl 5-(6-(3-ethylureido)pyridin-3-yl)-2-oxo-1,2-dihydropyridine-3-carboxylate

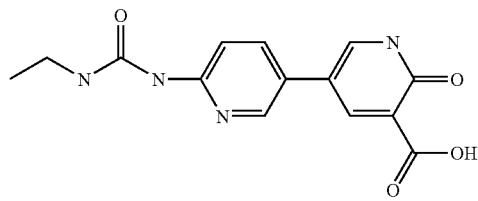

A solution of N-ethyl-N'-(5-(4,4,5,5-tetramethyl-1,3,2-dioxaborolan-2-yl)pyridin-2-yl)urea (Intermediate 1, 200 mg, 0.69 mmol), methyl 5-iodo-2-oxo-1,2-dihydro-3-pyridinecarboxylate (174 mg, 0.62 mmol), Tetrakispalladium (72.2 mg, 0.06 mmol), and cesium carbonate (224 mg, 0.69 mmol) in dioxane (4 mL) and water (1.000 mL) was heated to 100° C. in microwave for 1 h. The reaction mixture was filtered through Celite and washed with methanol. The resulting solution was concentrated under reduced pressure to give a yellow solid. The solid was triturated with acetone, then collected by filtration and added to hot acetone/water. The solution was cooled to room temperature, and the solid that formed was collected by filtration and placed under high vacuum to remove residual solvent (58 mg). MS (ESP): 317 (M+H+) for $C_{15}H_{16}N_4O_4$.

Example 51

5-(6-(3-ELthylureido)pyridin-3-yl)-2-oxo-1,2-dihydropyridine-3-carboxylic acid

To a solution of methyl 5-(6-(3-ethylureido)pyridin-3-yl)-2-oxo-1,2-dihydropyridine-3-carboxylate (Example 50, 58 mg, 0.18 mmol) in methanol (1 mL) was added sodium hydroxide (0.275 mL, 0.55 mmol). The reaction mixture was stirred at room temperature, then concentrated under reduced pressure, diluted with water, and acidifed to pH 4 with 10% HCl. The resulting suspension was cooled to 0° C. and the solid that formed was collected, then placed on a lyophilizer to remove residual solvent. MS (ES): 303 (M+H+) for $C_{14}H_{14}N_4O_4$.

Example 52

Ethyl 4-Dimethylcarbamoyl-2-[6-(3-ethyl-ureido)-pyridin-3-yl]-thiazole-5-carboxylate

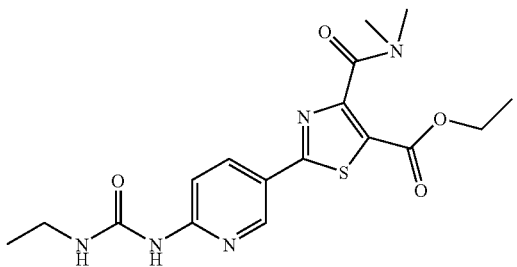

In a 10 mL of microwave vial, 2-chloro-4-dimethylcarbamoyl-thiazole-5-carboxylic acid ethyl ester (Intermediate 26, 0.1 g, 0.37 mmol), N-ethyl-N'-[5-(4,4,5,5-tetramethyl-[1,3,2]dioxaborolan-2-yl)-pyridin-2-yl]-urea (Intermediate1, 0.11 g, 0.37 mmol), cesium carbonate (0.12 g, 0.37 mmol), Tetrakis (triphenyl phosphino) palladium (0) (0.044 g, 0.037 mmol) in 4 mL of 4:1 dioxane:$H_2O$ was degassed for 30 min, then heated to 100° C. for 30 min. The reaction mixture was diluted with ethyl acetate (25 mL), then washed with water (10 mL). The organic layer was dried and concentrated to yield crude residue, which was purified by column chromatography over silica gel to afford 0.049 g (36.5%) of the title compound as a pale yellow solid. MS (APCI): 357 (M+H$^+$) for $C_{17}H_{21}N_5O_4S$; NMR: δ 1.25 (t, 3H), δ 1.38 (t, 3H), δ 2.91 (s, 3H), δ 3.18 (s, 3H), δ 3.42 (q, 2H), δ 4.36 (q, 2H), δ 6.92 (d, 1H), δ 8.14 (d, 1H), δ 8.78 (d, 1H).

Example 53

4-[(Dimethylamino)carbonyl]-2-(6-{[(ethylamino)carbonyl]amino}pyridin-3-yl)-1,3-thiazole-5-carboxylic acid

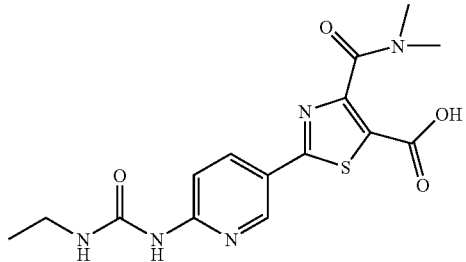

To a stirred solution of ethyl 4-dimethylcarbamoyl-2-[6-(3-ethyl-ureido)-pyridin-3-yl]-thiazole-5-carboxylate (Example 52, 0.7 g, 1.78 mmol) in methanol (15 mL) was added 2 N lithium hydroxide (8 mL). The mixture was heated to 50° C. overnight. After completion of the reaction, the reaction mixture was concentrated to dryness. Water was added and the pH was adjusted with 2 N hydrochloric acid to pH 2. The precipitated solid was filtered and dried under vacuum to afford 0.2 g (35.48%) of the title compound as a pale brown solid. MS (APCI): 364 (M+H$^+$) for $C_{16}H_{18}N_4O_4S$; NMR: δ 1.1 (t, 3H), δ 2.8 (s, 3H), δ 3.07 (s, 3H), δ 7.62 (d, 1H), δ 7.75 (br s, 1H), δ 8.25 (d, 1H), δ 8.82 (s, 1H), δ 9.55 (br s, 1H).

Example 54

N$^5$-Ethyl-2-(6-{[(ethylamino)carbonyl]amino}pyridin-3-yl)-N$^4$,N$^4$-dimethyl-1,3-thiazole-4,5-dicarboxamide

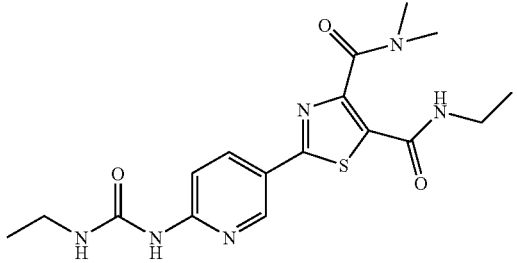

To a stirred solution of 4-[(dimethylamino)carbonyl]-2-(6-{[(ethylamino)carbonyl]amino}pyridin-3-yl)-1,3-thiazole-5-carboxylic acid (Example 53, 0.12 g, 3.3 mmol) in dry dimethylformamide (2 mL), HOBT (0.101 g, 6.6 mmol), N-methylmorpholine (0.108 mL, 9.9 mmol), EDC hydrochloride (0.126 g, 6.6 mmol), ethylamine (2 M in tetrahydrofuran, 0.13 mL, 3.3 mmol) were added at 0° C. and stirred overnight at room temperature. After completion of the reaction, reaction mixture was diluted with ethyl acetate (20 mL) and was washed with water (1×20 mL), 2 N hydrochloric acid (1×20 mL), and sodium bicarbonate solution (1×20 mL). The organic layer was dried, concentrated under reduced pressure and the residue was triturated with acetonitrile (1 mL). The obtained solid was filtered and dried to afford 0.018 g (20%) of the title compound as white solid. MS (APCI): 391 (M+H$^+$) for $C_{18}H_{23}N_5O_3S$; NMR: δ 1.06 (t, 3H), 2.86 (s, 3H), 2.99 (s, 3H), 3.17 (q, 4H), 7.60 (d, 1H), 7.76 (br s, 1H), 8.22 (dd, 1H), 8.72 (br t, 1H), 8.78 (s, 1H), 9.52 (br s, 1H).

Example 55-58

The following compounds were synthesized according to the procedure described for Example 54 using the indicated starting materials.

| Ex | Compound | Data | SM |
|---|---|---|---|
| 55 | 2-[6-(3-Ethyl-ureido)-pyridin-3-yl]-thiazole-4,5-dicarboxylic acid 4-dimethylamide 5-propylamide | MS (ES): 405 (M + H$^+$) for $C_{18}H_{24}N_6O_3S$; NMR: 0.89 (t, 3H), 1.1 (t, 3H), 1.49 (qq, 2H), 2.9 (s, 3H), 3.04 (s, 3H), 3.2 (q, 4H), 7.62 (d, 1H), 7.76 (bs, 1H), 8.22 (dd, 1H), 8.74 (br s, 1H), 8.79 (d, 1H), 9.52 (br s, 1H). | Example 53 and propylamine |
| 56 | 2-[6-(3-Ethyl-ureido)-pyridin-3-yl]-thiazole-4,5-dicarboxylic acid 4-dimethylamide 5-isopropylamide | MS (ES): 405 (M + H$^+$) for $C_{18}H_{24}N_6O_3S$; NMR: 1.10 (t, 3H), 1.14 (d, 6H), 2.95 n(s, 3H), 3.05 (s, 3H), 3.2 (q, 2H), 3.97 (m, 1H), 7.62 (d, 1H), 7.75 (br s, 1H), 8.22 (dd, 1H), 8.67 (d, 1H), 8.78 (d, 1H), 9.52 (br s, 1H). | Example 53 and isopropylamine |

-continued

| Ex | Compound | Data | SM |
|---|---|---|---|
| 57 | 2-[6-(3-Ethyl-ureido)-pyridin-3-yl]-thiazole-4,5-dicarboxylic acid bis-dimethylamide | MS (ES): 391 (M + H$^+$) for C$_{17}$H$_{22}$N$_6$O$_3$S; NMR: 1.27 (t, 3H), 3.09 (s, 3H), 3.119 (s, 3H), 3.17 (s, 3H), 3.21 (s, 3H), 3.43 (q, 2H), 6.92 (d, 1H), 8.21 (dd, 1H), 8.46 (br t, 1H), 8.73 (s, 1H), 9.15 (br s, 1H) | Example 53 and dimethyl-amine |
| 58 | 2-[6-(3-Ethyl-ureido)-pyridin-3-yl]-thiazole-4,5-dicarboxylic acid 5-yclopentylamide 4-dimethylamide | MS (ES): 431 (M + H$^+$) for C$_{20}$H$_{26}$N$_6$O$_3$S; NMR: 1.24 (t, 3H), 1.59 (m, 6H), 1.98 (q, 2H), 3.09 (s, 3H), 3.15 (s, 3H), 3.42 (q, 2H), 4.25 (m, 1H), 6.85 (d, 1H), 8.08 (dd, 1H), 8.43 (br t, 1H), 8.72 (s, 1H), 9.03 (dd, 1H), 9.12 (br s, 1H). | Example 53 and cyclopentyl-amine |

Example 59

Ethyl 4-ethylcarbamoyl-2-[6-(3-ethyl-ureido)-pyridin-3-yl]-thiazole-5-carboxylate

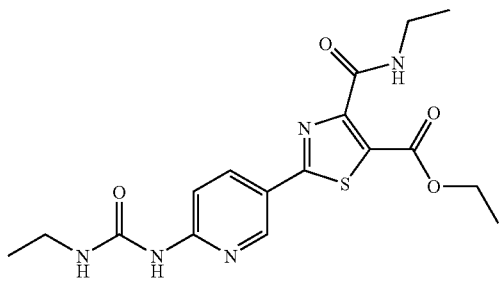

To a stirred solution of 2-chloro-5-(ethoxy carbonyl)-1,3-thiazole-4-carboxylic acid (Intermediate 7, 1.0 g, 4.2 mM) in dry dichloromethane (20 mL) was added oxalyl chloride (0.729 mL, 8.4 mM) and 2 drops of dry dimethylformamide. The reaction mixture was refluxed to 45° C. for 1½ h, then cooled to room temperature and evaporated to dryness under reduced pressure. The resulting residue was dissolved in dry dichloromethane (20 mL) and cooled to 0° C. To the above reaction mixture, 2,6-lutidine (0.44 mL, 3.7 mM) was added followed by addition of ethylamine (2M solution in tetrahydrofuran, 3.5 mL, 3.7 mM). The reaction mixture was concentrated to dryness and the residue was dissolved in ethyl acetate (2×50 mL). The organic layer was washed with 1 N hydrochloric acid (1×50 mL), dried over anhydrous sodium sulfate, and concentrated under vacuum to afford ethyl 2-chloro-4-ethylcarbamoyl-thiazole-5-carboxylate (1.05 g (83%)) as a thick syrup, which was taken to next step as such.

In a 10 mL microwave vial, ethyl 2-chloro-4-ethylcarbamoyl-thiazole-5-carboxylate (0.49 g, 1.86 mM), N-ethyl-N'-[5-(4,4,5,5-tetramethyl-[1,3,2]dioxaborolan-2-yl)-pyridin-2-yl]-urea (Intermediate 1, 0.544 g, 1.86 mM), cesium carbonate (0.607 g, 1.86 mM), Tetrakis(triphenylphosphino) palladium (0) (0.209 g, 0.18 mM) in 15 mL of 4:1 dioxane: H$_2$O was degassed for 30 min and heated to 100° C. for 30 min. The reaction mixture was cooled to room temperature and diluted with ethyl acetate (25 mL). The organic layer was washed with water (10 mL), dried over sodium sulfate, and concentrated under reduced pressure to yield crude residue, which was purified by column chromatography over silica gel to afford 0.210 g (13.5%) of the title compound as solid. MS (APCI): 391 (M+H$^+$) for C$_{17}$H$_{21}$N$_5$O$_4$S; NMR: 1.29 (t, 9H), 3.44 (q, 2H), 3.53 (q, 2H), 4.42 (q, 2H), 6.92 (d, 1H), δ 7.85 (br s, 1H), δ 8.18 (dd, 1H), δ 8.53 (br s, 1H), δ 9.085 (br s, 1H), δ 9.085 (br s, 1H).

Example 60

4-Ethylcarbamoyl-2-[6-(3-ethyl-ureido)-pyridin-3-yl]-thiazole-5-carboxylic acid

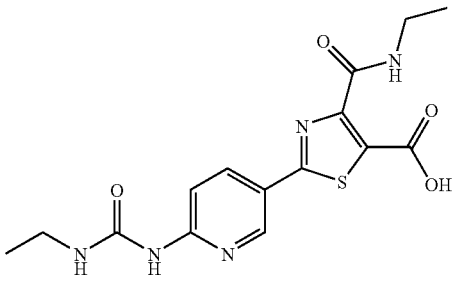

To a stirred solution of ethyl 4-ethylcarbamoyl-2-[6-(3-ethyl-ureido)-pyridin-3-yl]-thiazole-5-carboxylate (Example 59, 0.210 mg, 0.538 mM) in methanol (4 mL) was added 2 N lithium hydroxide (2 mL). The reaction mixture was heated to 50° C. overnight, then cooled to room temperature, and concentrated to dryness. Water was added and the pH was adjusted with 2N hydrochloric acid to pH 2. The precipitated solid was filtered and dried under vacuum to afford 0.13 g (66.6%) of the title compound as a solid. NMR: 1.11 (t, 3H), 1.23 (t, 3H), 3.19 (q, 4H), 7.71 (d, 1H), 7.81 (br s, 1H), 8.41 (d, 1H), 9.01 (s, 1H), 9.66 (s, 1H), 9.83 (br s, 1H).

Example 61

2-[6-(3-Ethyl-ureido)-pyridin-3-yl]-thiazole-4,5-dicarboxylic acid 5-dimethylamide 4-ethylamide

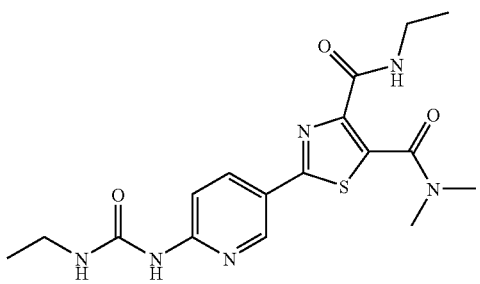

To a stirred solution of 4-ethylcarbamoyl-2-[6-(3-ethyl-ureido)-pyridin-3-yl]-thiazole-5-carboxylic acid (Example 60, 0.12 g, 0.358 mM) in dry dimethylformamide (2 mL), HOBT (0.109 g, 0.716 mM), N-methylmorpholine (0.118 mL, 1.074 mM), EDC hydrochloric acid (0.137 g, 0.716 mM), N,N-dimethylamine (2 M in tetrahydrofuran, 0.358 mM) were added at 0° C. and stirred overnight at room temperature. The reaction mixture was diluted with ethyl acetate (20 mL), washed with water (1×20 mL), 2 N hydrochloric acid (1×20 mL), and sodium bicarbonate solution (1×20 mL). The organic layer was dried over sodium sulfate, concentrated under reduced pressure, and the resulting residue was triturated with acetonitrile (1 mL). The solid obtained was collected by filtration and dried in vacuum oven to afford 0.014 g (11.6%) of the title compound as solid. MS (APCI): 389 (M+H$^+$) for $C_{17}H_{22}N_6O_3S$; NMR: 1.27 (3, 6H), 2.99 (s, 3H), 3.18 (s, 3H), 3.45 (m, 4H), 6.87 (d, 1H), 7.33 (br s, 1H), 8.08 (d, 1H), 8.11 (br s, 1H), 8.74 (s, 1H), 9.08 (br s, 1H).

Example 62

Ethyl 2-[6-(3-ethyl-ureido)-pyridin-3-yl]-4-propyl-carbamoyl-thiazole-5-carboxylate

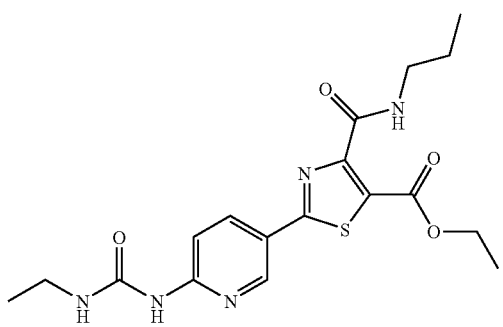

In a 10 mL of microwave vial, ethyl 2-chloro-4-propylcarbamoyl-thiazole-5-carboxylate (Intermediate 27, 1.4 g, 5.4 mM), N-ethyl-N'-[5-(4,4,5,5-tetramethyl-1,3,2]dioxaborolan-2-yl)-pyridin-2-yl]-urea (Intermedite 1, 1.57 g, 5.4 mM), cesium carbonate (1.75 g, 5.4 mM), Tetrakis (triphenylphosphino) palladium (0) (0.62 g, 0.54 mM) in 15 mL of 4:1 dioxane:H$_2$O was degassed for 30 min and heated to 100° C. for 30 min. The reaction mixture was diluted with ethyl acetate (25 mL), then washed with water (10 mL). The organic layer was dried and concentrated to yield a crude residue which was purified by column chromatography over silica gel to afford 0.33 g (16.12%) of the title compound as solid. MS (APCI): 404 (M+H$^-$) for $C_{18}H_{23}N_5O_4S$; NMR: 1.01 (t, 3H), 1.26 (t, 3H), 1.42 (t, 3H), 1.68 (q, 2H), 3.45 (q, 4H), 4.42 (q, 2H), 6.78 (d, 1H), 7.4 (br s, 1H), 7.91 (d, 1H), 8.10 (dd, 1H), 8.8 (s, 1H), 9.09 (br s, 1H).

Example 63

2-[6-(3-Ethyl-ureido)-pyridin-3-yl]-4-propylcarbamoyl-thiazole-5-carboxylic acid

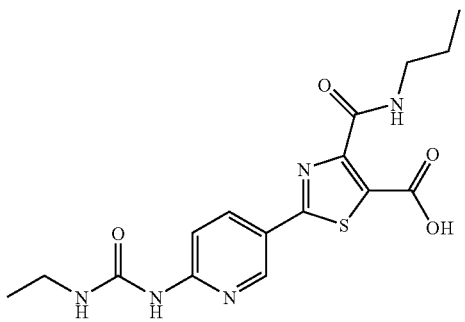

To a stirred solution of ethyl 2-[6-(3-ethyl-ureido)-pyridin-3-yl]-4-propylcarbamoyl-thiazole-5-carboxylate (Example 62, 0.33 g, 0.8 mM) in methanol (15 mL) was added 2 N lithium hydroxide (4 mL). The mixture was heated to 50° C. overnight, then concentrated to dryness. 2N hydrochloric acid was added to the concentrate, and the precipitated solid was filtered and dried under vacuum to afford 0.259 g (72%) of the title compound as solid. NMR: 0.92 (t, 3H), 1.10 (t, 3H), 1.63 (m, 2H), 3.20 (q, 2H), 3.36 (q, 2H), 7.67 (d, 1H), 7.68 (br s, 1H), 8.39 (dd, 1H), 9.02 (s, 1H), 9.62 (br s, 1H), 9.78 (br s, 1H).

Example 64

2-[6-(3-ethyl-ureido)-pyridin-3-yl]-thiazole-4,5-dicarboxylic acid 5-dimethylamide 4-propylamide

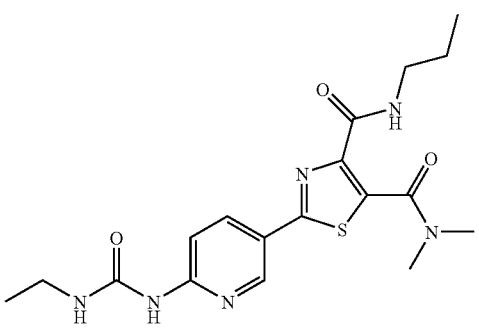

To a stirred solution of 2-[6-(3-ethyl-ureido)-pyridin-3-yl]-4-propylcarbamoyl-thiazole-5-carboxylic acid (Example 63, 0.12 g, 0.31 mM) in dry dimethylformamide (2 mL), HOBT (0.097 g, 0.63 mM), N-methylmorpholine (0.104 mL, 0.95 mM), EDC hydrochloric acid (0.12 g, 0.63 mM), and N,N-dimethylamine (2 M in tetrahydrofuran) (0.159 g, 0.31 mM) were added at 0° C. and stirred overnight at room temperature. The reaction mixture was diluted with ethyl acetate (20 mL), then washed with water (1×20 mL), 2 N hydrochloric acid (1×20 mL), and sodium bicarbonate solution (1×20 mL). The organic layer was dried over sodium sulfate, concentrated under reduced pressure. The residue was triturated with acetonitrile (1 mL) to obtained a solid which was collected by filtration, then dried to afford 0.013 g (15%) of the title compound as solid. MS (APCI): 405 (M+H⁻) for C₁₈H₂₄N₆O₃S; NMR: 0.88 (t, 3H), 1.10 (t, 3H), 1.54 (q, 2H), 2.83 (s, 3H), 2.99 (s, 3H), 3.22 (m, 4H), 7.63 (d, 1H), 7.70 (br s, 1H), 8.29 (dd, 1H), 8.59 (tt, 1H), 8.88 (d, 1H), 9.51 (bs, 1H).

Example 65

Ethyl 2-[6-(3-ethyl-ureido)-pyridin-3-yl]-4-isopropylcarbamoyl-thiazole-5-carboxylate

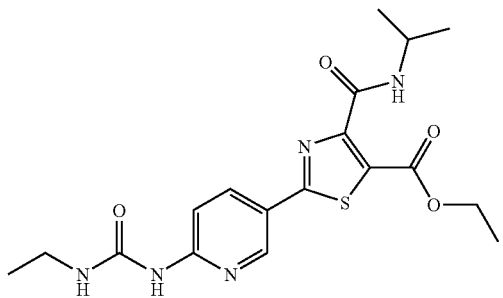

In a 10 mL of microwave vial, ethyl 2-chloro-4-isopropylcarbamoyl-thiazole-5-carboxylate (Intermediate 28, 1.1 g, 3.97 mmol), N-ethyl-N'-[5-(4,4,5,5-tetramethyl-[1,3,2]dioxaborolan-2-yl)-pyridin-2-yl]-urea (Intermediate 1, 1.15 g, 3.97 mmol), cesium carbonate (1.29 g, 3.97 mmol), Tetrakis (triphenylphosphino) palladium (0) (0.458 g, 0.397 mmol) in 15 mL of 4:1 dioxane:H₂O was degassed for 30 min, then heated to 100° C. for 30 min. The reaction mixture was diluted with ethyl acetate (25 mL), then washed with water (10 mL). The organic layer was dried, then concentrated under reduced pressure to yield crude a residue which was purified by column chromatography over silica gel to afford 0.195 g (17.72%) of the title compound as solid. MS (APCI): 406 (M+H⁻) for C₁₈H₂₃N₅O₄S; NMR: 1.13 (t, 3H), δ 1.16 (d, 6H), 1.28 (t, 3H), δ 3.2 (q, 2H), 4.04 (m, 1H), 4.29 (q, 2H), 7.63 (d, 1H), 7.70 (br s, 1H), 8.27 (dd, 1H), δ 8.45 (d, 1H), 8.83 (d, 1H), 9.56 (s, 1H).

Example 66

2-[6-(3-Ethyl-ureido)-pyridin-3-yl]-4-isopropylcarbamoyl-thiazole-5-carboxylic acid

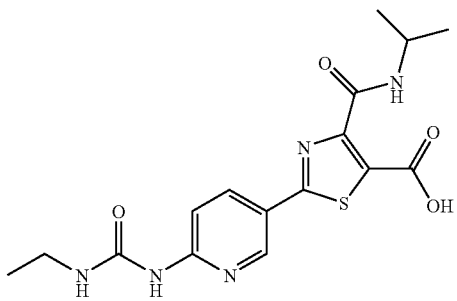

To a stirred solution of ethyl 2-[6-(3-ethyl-ureido)-pyridin-3-yl]-4-isopropylcarbamoyl-thiazole-5-carboxylate (Example 65, 0.195 g, 0.48 mmol) in methanol (7 mL) was added 2 N lithium hydroxide (2 mL). The mixture was heated to 50° C. overnight, then concentrated to dryness water was added and the pH was adjusted to pH 2 with 2N hydrochloric acid. The precipitated solid was filtered and dried under vacuum to afford 0.15 g (76.2%) of the title compound as a solid. NMR: 1.11 (t, 3H), 1.28 (d, 6H), 3.22 (q, 2H), 4.20 (m, 1H), 7.62 (d, 1H), 7.7 (r bs, 1H), δ 8.42 (dd, 1H), 8.57 (d, 1H), δ 9.03 (s, 1H).

Example 67

2-[6-(3-Ethyl-ureido)-pyridin-3-yl]-thiazole-4,5-dicarboxylic acid 5-dimethylamide 4-ethylamide

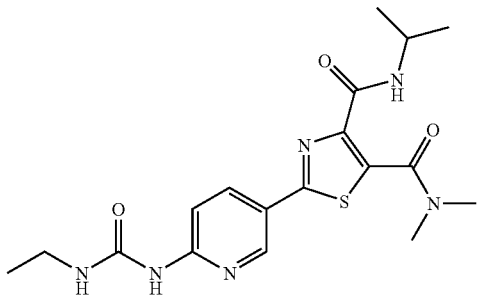

To a stirred solution of 2-[6-(3-ethyl-ureido)-pyridin-3-yl]-4-isopropylcarbamoyl-thiazole-5-carboxylic acid (Example 66, 0.15 g, 0.39 mM) in dry dimethylformamide (2 mL), HOBT (0.121 g, 0.79 mmol), N-methylmorpholine (0.131 mL, 0.79 mmol), EDC hydrochloride (0.152 g, 0.79 mM), and N,N-dimethylamine (2 M in tetrahydrofuran) (0.198 mL, 0.39 mmol) were added at 0° C. and stirred over night at room temperature. After completion of the reaction, the reaction mixture was diluted with ethyl acetate (20 mL), then washed with water (1×20 mL), 2 N hydrochloric acid (1×20 mL), and sodium bicarbonate solution (1×20 mL). The organic layer was dried, concentrated and the residue was titrated with acetonitrile (1 mL) to afford 0.073 g (45.3%) of the title compound as solid. MS (APCI): 405 (M+H⁻) for C₁₈H₂₄N₆O₃S; NMR: 1.1 (t, 3H), 1.20 (d, 6H), 2.84 (s, 3H), 2.99 (s, 3H), 3.19 (q, 2H), 4.08 (m, 1H), 7.62 (d, 1H), 7.76 (br s, 1H), 8.25 (dd, 1H), 8.91 (d, 1H), 9.519 (br s, 1H).

Example 68

Ethyl 6'-{[(ethylamino)carbonyl]amino}-5''-fluoro-3,3':4',3''-terpyridine-5-carboxylate

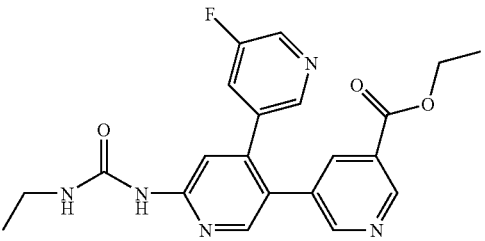

N-(5'-bromo-5-fluoro-3,4'-bipyridin-2'-yl)-N'-ethylurea (Intermediate 30, 0.34 g, 1.00 mmol), ethyl 5-(4,4,5,5-tetramethyl-1,3,2-dioxaborolan-2-yl)nicotinate (Oakwood Products, Inc., Cat. #021607) (0.306 g, 1.10 mmol), tetrakis triphenyl phosphine palladium (0.058 g, 0.05 mmol), and cesium carbonate (0.359 g, 1.10 mmol) were added to a microwave vial and degassed with nitrogen. A solution of 1,4-dioxane: water (4:1, 10 mL) was added to the solution and the reaction mixture was heated to 100° C. for 30 minutes. The reaction mixture was partitioned between water and ethyl acetate, and the organic layer was washed with saturated sodium bicarbonate solution, water, and brine, then dried over magnesium sulfate. The solvent was removed and the residue was purified by silica gel chromatography, eluting with (0-100% EtOAc/hexanes) to give the title compound as a white solid (190 mg). MS (ESP): 410 (MH⁺) for $C_{21}H_{20}FN_5O_3$;

NMR: 1.24 (t, 3H) 1.37 (t, 3H) 3.34-3.51 (m, 2H) 4.38 (q, 2H) 7.08 (s, 1H) 7.16-7.23 (m, 1H) 8.06 (t, 1H) 8.20 (s, 1H) 8.26 (s, 1H) 8.43 (dd, 2H) 9.11 (d, 1H) 9.16 (s, 1H) 9.96 (s, 1H).

Example 69

6'-{[(Ethylamino)carbonyl]amino}-5"-fluoro-3,3':4',3"-terpyridine-5-carboxylic acid

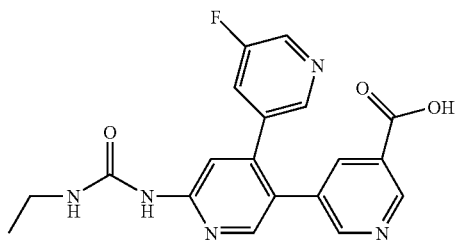

Ethyl 6'-{[(ethylamino)carbonyl]amino}-5"-fluoro-3,3':4',3"-terpyridine-5-carboxylate (Example 68, 0.19 g, 0.46 mmol) was added to a 25 mL round-bottomed flask with THF (3 mL) to give a white suspension. Lithium hydroxide (1.160 mL, 1.16 mmol) was added to the mixture, and the solution was stirred at 45° C. for 2 h. The solvent was removed under reduced pressure, and the resulting residue was diluted with water and adjusted to pH~4 by 2N HCl. The precipitate that formed was collected by filtration, washed with water, and dried to give the title compound as a white solid (154 mg). MS (ESP): 382 (MH⁺) for $C_{19}H_{16}FN_5O_3$; NMR: 1.08 (t, 3H), 3.13-3.24 (m, 2H), 7.63 (s, 1H) 7.64-7.68 (m, 1H) 7.69-7.77 (m, 1H), 7.93 (t, 1H), 8.19 (t, 1H), 8.36 (s, 1H), 8.45 (d, 1H), 8.55 (d, 1H), 8.90 (d, 1H), 9.45 (s, 1H).

Example 70

6'-{[(ethylamino)carbonyl]amino}-5"-fluoro-N-methyl-3,3':4',3"-terpyridine-5-carboxamide

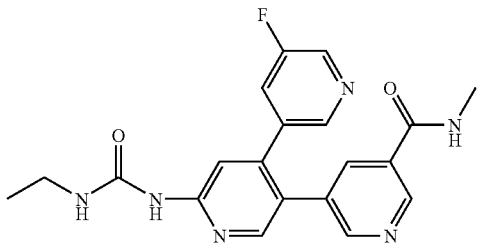

In a 25 mL round-bottomed flask was 6'-{[(ethylamino)carbonyl]amino}-5"-fluoro-3,3':4',3"-terpyridine-5-carboxylic acid (Example 69, 0.1 g, 0.26 mmol), HATU (0.130 g, 0.34 mmol), and DIEA (0.137 mL, 0.79 mmol) in DMF (2 mL) to give a orange solution. Methylamine (0.262 mL, 0.52 mmol) was added after 15 min. The reaction mixture was stirred at room temperature for 3 h, then partitioned between water and ethyl acetate and layers separated. The organic layer was washed with saturated sodium bicarbonate solution, water, brine and dried over magnesium sulfate. The solvent was removed and the resulting residue was washed with acetonitrile to give the title compound as a white solid (20 mg). MS (ESP): 395 (MH⁺) for $C_{20}H_{19}FN_6O_2$; NMR: 1.09 (t, 3H), 2.77 (d, 3H), 3.13-3.25 (m, 2H), 7.60-7.72 (m, 3H), 8.01 (t, 1H), 8.19 (t, 1H), 8.34 (d, 1H), 8.37 (s, 1H), 8.56 (d, 1H), 8.62 (d, 1H), 8.84 (d, 1H), 9.45 (s, 1H).

Examples 71-89

The following compounds were made by an analogous method to Example 1 from the starting materials listed.

| Ex | Compound | Structure | Data | SM |
|---|---|---|---|---|
| 71 | Methyl 2-(6-{[(ethylamino)carbonyl]amino}pyridin-3-yl)-4-[1-(2-methoxyethyl)-1H-imidazol-2-yl]-1,3-thiazole-5-carboxylate | 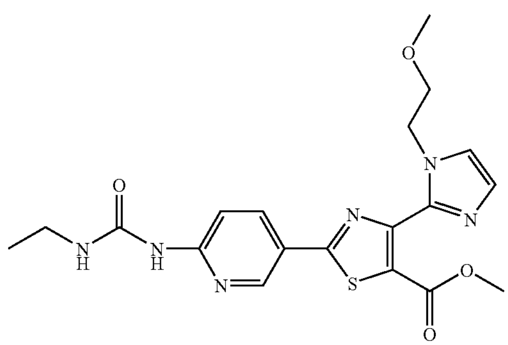 | MS (ESP): 431 (M + 1) for $C_{18}H_{22}N_6O_4$ NMR: 1.09 (t, 3H); 3.15 (s, 3H), 3.16-3.22 (m, 2H); 3.55 (t, 2H), 3.75 (s, 3H); 4.14 (t, 2H); 7.02 (s, 1H); 7.36 (s, 1H); 7.63 (d, 1H); 7.79 (t, 1H); 8.29 (dd, 1H); 8.87 (d, 1H); 9.60 (s, 1H). | Intermediate 1 and Intermediate 54 |
| 72 | Methyl 2-(6-{[(ethylamino)carbonyl]amino}pyridin-3-yl)-4-(1-methyl-1H-1,2,4-triazol-5-yl)-1,3-thiazole-5-carboxylate | 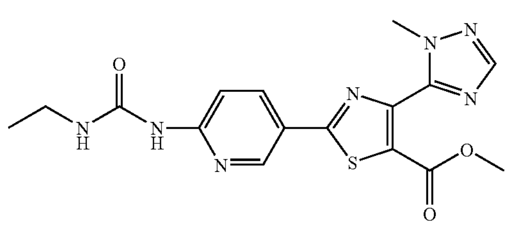 | MS (ES) MH⁺: 388 for $C_{16}H_{17}N_7O_3S$; NMR: 1.09 (t, 3H); 3.16-3.22 (m, 2H); 3.78 (s, 3H); 3.81 (s, 3H); 7.64 (d, 1H); 7.75 (t, 1H); 8.10 (s, 1H); 8.31 (dd, 1H); 8.89 (d, 1H); 9.60 (s, 1H). | Intermediate 1 and Intermediate 58 |

| Ex | Compound | Structure | Data | SM |
|----|----------|-----------|------|-----|
| 73 | Ethyl 2-(6-{[(ethylamino)carbonyl]amino}pyridin-3-yl)-4-{[(2-methoxyethyl)amino]carbonyl}-1,3-thiazole-5-carboxylate | 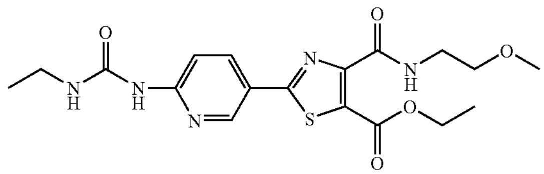 | MS (ES) MH+: 422 for $C_{18}H_{23}N_5O_5S$; | Intermediate 1 and ethyl 2-chloro-4-{[(2-methoxyethyl)amino]carbonyl}-1,3-thiazole-5-carboxylate (WO2006087543) |
| 74 | Ethyl 2-(6-{[(ethylamino)carbonyl]amino}pyridin-3-yl)-4-({[(1S)-2-methoxy-1-methylethyl]amino}carbonyl)-1,3-thiazole-5-carboxylate | 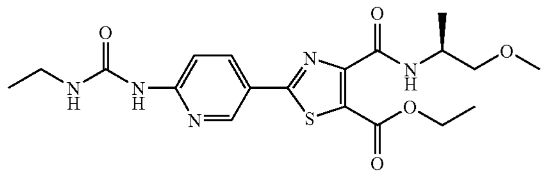 | MS (ES) MH+: 436 for $C_{19}H_{25}N_5O_5S$; NMR: 1.09 (t, 3H); 1.23 (d, 3H) 3.15-3.22 (m, 2H); 3.28 (s, 3H); 3.37-3.45 (m, 3H); 3.50-3.56 (m, 1H); 4.28-4.36 (m, 1H); 7.64 (d, 1H); 7.76 (t, 1H); 8.39 (dd, 1H); 9.03 (d, 1H); 9.38 (d, 1H); 9.62 (s, 1H). | Intermediate 1 and ethyl 2-chloro-4-({[(1S)-2-methoxy-1-methylethyl]amino}-carbonyl)-1,3-thiazole-5-carboxylate (WO2006087543) |
| 75 | Methyl 2-(6-{[(ethylamino)carbonyl]amino}pyridin-3-yl)-4-(1-methyl-1H-imidazol-2-yl)-1,3-thiazole-5-carboxylate | 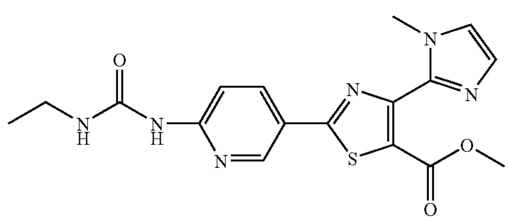 | MS (ES) MH+: 387 for $C_{17}H_{18}N_6O_3S$; $^1$H-NMR (DMSO-$d_6$) δ: 1.09 (t, 3H); 3.15-3.24 (m, 2H); 3.62 (s, 3H); 3.76 (s, 3H), 7.02 (s, 1H); 7.32 (s, 1H); 7.61 (d, 1H); 7.78 (t, 1H); 8.28 (dd, 1H); 8.86 (d, 1H); 9.59 (s, 1H). | Intermediate 1 and Intermediate 61 |
| 76 | Ethyl 4-[(tert-butylamino)carbonyl]-2-(6-{[(ethylamino)carbonyl]amino}pyridin-3-yl)-1,3-thiazole-5-carboxylate | 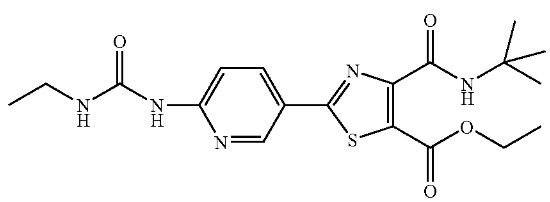 | MS (ES) MH+: 420 for $C_{19}H_{25}N_5O_4S$; NMR: 1.09 (t, 3H); 1.28 (t, 3H); 1.36 (s, 9H); 3.14-3.22 (m, 2H); 4.29 (q, 2H); 7.62 (d, 1H); 7.75 (t, 1H); 8.21 (s, 1H); 8.27 (dd, 1H); 8.82 (d, 1H) 9.58 (s, 1H). | Intermediate 1 and Intermediate 63 |
| 77 | Ethyl 6'-{[(ethylamino)carbonyl]amino}-4'-phenyl-3,3'-bipyridine-5-carboxylate | 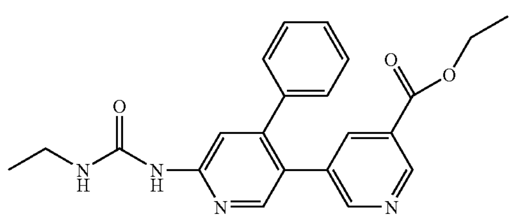 | MS (ESP): 391 (M + 1) for $C_{22}H_{22}N_4O_3$; NMR: 1.09 (t, 3H); 1.27 (t, 3H); 3.18-3.22 (m, 2H); 4.27 (q, 2H); 7.12-7.15 (m, 2H); 7.32-7.34 (m, 3H); 7.54 (s, 1H); 7.85 (brs, 1H); 7.95 (s, 1H); 8.33 (s, 1H); 8.50 (d, 1H); 8.91 (d, 1H); 9.41 (s, 1H) | Intermediate 35 and ethyl 5-(4,4,5,5-tetramethyl-1,3,2-dioxaborolan-2-yl)nicotinate |
| 78 | Ethyl 3-(6-{[(ethylamino)carbonyl]amino}-4-phenylpyridin-3-yl)benzoate | 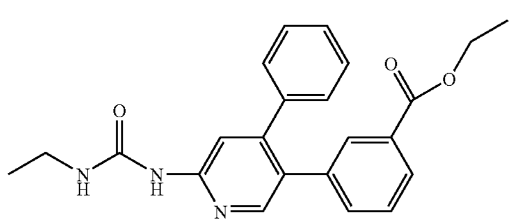 | MS (ESP): 390 (M + 1) for $C_{23}H_{23}N_3O_3$ | Intermediate 35 and [3-(ethoxycarbonyl)phenyl]boronic acid |

-continued

| Ex | Compound | Structure | Data | SM |
|---|---|---|---|---|
| 79 | Methyl 2-(6-{[(ethylamino)carbonyl]amino}-4-phenylpyridin-3-yl)-1,3-thiazole-5-carboxylate | 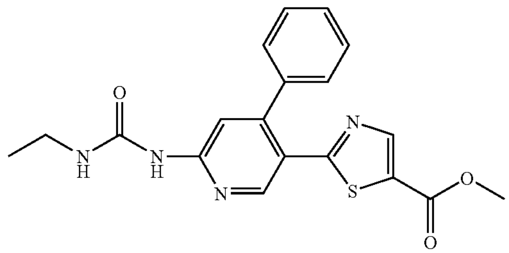 | MS (ESP): 383 (M + 1) for $C_{19}H_{18}N_4O_3S$ | Intermediate 52 and methyl 2-bromo-1,3-thiazole-5-carboxylate |
| 80 | Ethyl 4-[(butylamino)carbonyl]-2-(6-{[(ethylamino)carbonyl]amino}-4-phenylpyridin-3-yl)-1,3-thiazole-5-carboxylate | 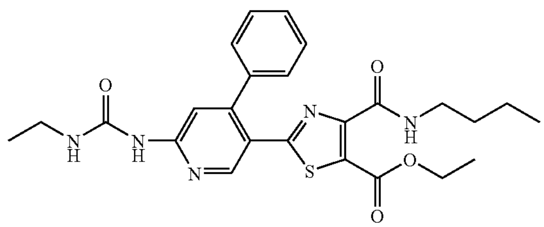 | MS (ESP): 496 (M + 1) for $C_{25}H_{29}N_5O_4S$; NMR: 0.90 (t, 3H); 1.09 (t, 3H); 1.28 (t, 3H); 1.30-1.34 (m, 2H); 1.44-1.52 (m, 2H); 3.18-3.22 (m, 4H); 4.17 (q, 2H); 7.30-7.38 (m, 2H); 7.53-7.56 (m, 4H); 7.72 (s, 1H); 8.51 (br s, 1H); 8.93 (s, 1H); 9.63 (s, 1H). | Intermediate 52 and Intermediate 5 |
| 81 | Ethyl 6'-{[(ethylamino)carbonyl]amino}-4'-(4-ethyl-1,3-thiazol-2-yl)-3,3'-bipyridine-5-carboxylate | 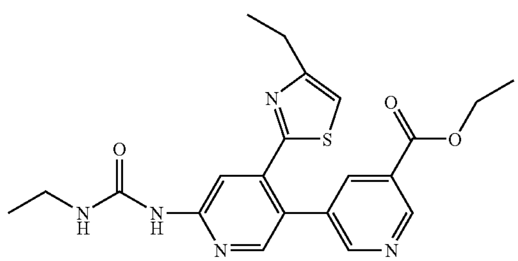 | MS (ES) MH+: 425 for $C_{22}H_{23}N_5O_3S$; NMR: 1.05 (t, 3H); 1.11 (t, 3H); 1.31 (t, 3H); 2.62 (q, 2H); 3.18-3.24 (m, 2H); 4.34 (q, 2H); 7.41 (s, 1H); 7.70 (brs, 1H); 8.13 (d, 2H); 8.30 (s, 1H); 8.70 (s, 1H); 9.07 (s, 1H); 9.48 (s, 1H) | Intermediate 44 and ethyl 5-(4,4,5,5-tetramethyl-1,3,2-dioxaborolan-2-yl)nicotinate |
| 82 | Ethyl 3-[6-{[(ethylamino)carbonyl]amino}-4-(4-ethyl-1,3-thiazol-2-yl)pyridin-3-yl]benzoate | 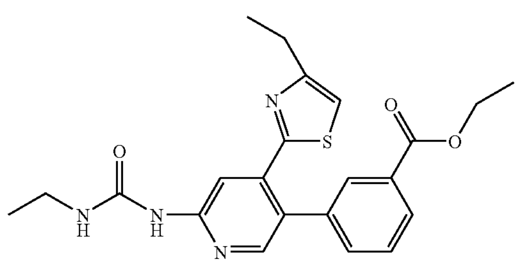 | MS (ESP): 424 (M + 1) for $C_{22}H_{24}N_4O_3S$ | Intermediate 44 and [3-(ethoxycarbonyl)phenyl]boronic acid |
| 83 | Ethyl 6'-{[(ethylamino)carbonyl]amino}-4'-[4-(trifluoromethyl)-1,3-thiazol-2-yl]-3,3'-bipyridine-5-carboxylate | 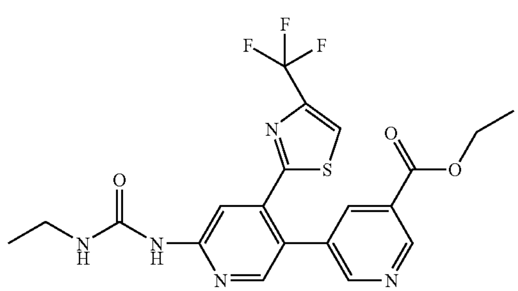 | MS (ES) MH+: 466 for $C_{20}H_{18}F_3N_5O_3S$; NMR: 1.11 (t, 3H); 1.31 (t, 3H); 3.18-3.24 (m, 2H); 4.34 (q, 2H); 7.57 (brs, 1H); 8.16-8.18 (m, 1H); 8.21 (s, 1H); 8.39 (s, 1H); 8.58 (s, 1H); 8.75 (d, 1H); 9.10 (s, 1H); 9.52 (s, 1H) | Intermediate 38 and ethyl 5-(4,4,5,5-tetramethyl-1,3,2-dioxaborolan-2-yl)nicotinate |

| Ex | Compound | Structure | Data | SM |
|----|----------|-----------|------|-----|
| 84 | Methyl 2-{6-{[(ethylamino)carbonyl]amino}-4-[4-(trifluoromethyl)-1,3-thiazol-2-yl]pyridin-3-yl}-1,3-thiazole-5-carboxylate | 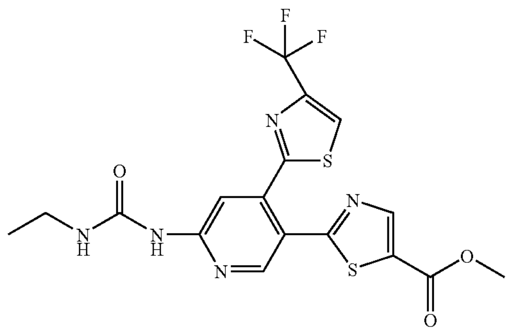 | MS (ES) MH+: 458 for $C_{17}H_{14}F_3N_5O_3S_2$ | Intermediate 51 and methyl 2-bromo-1,3-thiazole-5-carboxylate |
| 85 | Ethyl 6'-{[(ethylamino)carbonyl]amino}-3,3':4',3''-terpyridine-5-carboxylate | 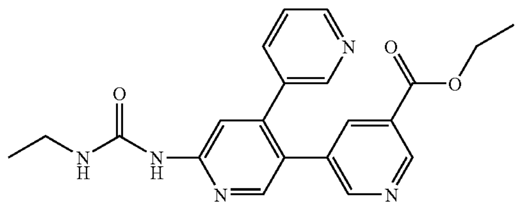 | MS (ESP): 392 (M + 1) for $C_{21}H_{21}N_5O_3$<br>$^1$H-NMR (DMSO-d$_6$) δ: 1.09 (t, 3H); 1.27 (t, 3H); 3.14-3.24 (m, 2H); 4.28 (q, 2H); 7.35-7.39 (m, 1H), 7.60 (s, 2H); 7.80 (s, 1H); 7.97 (s, 1H); 8.35 (s, 1H) 8.37 (s, 1H); 8.52 (d, 2H); 8.94 (s, 1H) 9.45 (s, 1H) | Intermediate 34 and ethyl 5-(4,4,5,5-tetramethyl-1,3,2-dioxaborolan-2-yl)nicotinate |
| 86 | Ethyl 6'-{[(ethylamino)carbonyl]amino}-6''-fluoro-3,3':4',3''-terpyridine-5-carboxylate | 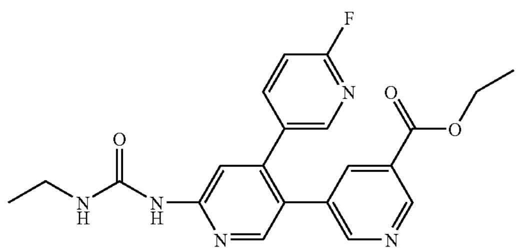 | MS (ESP): 410 (M + 1) for $C_{21}H_{20}FN_5O_3$<br>$^1$H-NMR (DMSO-d$_6$) δ: 1.11 (t, 3H); 1.29 (t, 3H); 3.15-3.24 (m, 2H); 4.31 (q, 2H), 7.19 (dd, 1H), 7.63 (s, 1H); 7.77-7.83 (m, 2H); 7.99 (s, 1H); 8.08 (d, 1H); 8.39 (s, 1H); 8.57 (d, 1H); 8.96 (s, 1H); 9.46 (s, 1H) | Intermediate 31 and ethyl 5-(4,4,5,5-tetramethyl-1,3,2-dioxaborolan-2-yl)nicotinate |
| 87 | Ethyl 6'-{[(isopropylamino)carbonyl]amino}-4'-[4-(trifluoromethyl)-1,3-thiazol-2-yl]-3,3'-bipyridine-5-carboxylate | 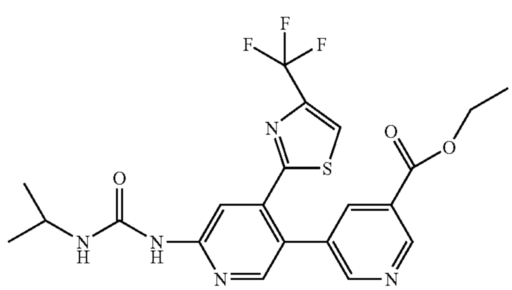 | MS (ES) MH+: 480 for $C_{21}H_{20}F_3N_5O_3S$; | Intermediate 36 and ethyl 5-(4,4,5,5-tetramethyl-1,3,2-dioxaborolan-2-yl)nicotinate |
| 88 | Ethyl 6'-{[(sec-butylamino)carbonyl]amino}-4'-[4-(trifluoromethyl)-1,3-thiazol-2-yl]-3,3'-bipyridine-5-carboxylate | 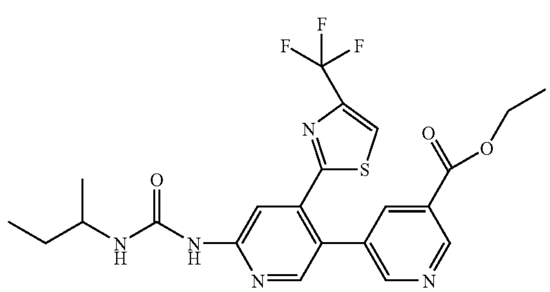 | MS (ES) MH+: 494 for $C_{22}H_{22}F_3N_5O_3S$ | Intermediate 47 and ethyl 5-(4,4,5,5-tetramethyl-1,3,2-dioxaborolan-2-yl)nicotinate |

Examples 89-106

The following compounds were made by an analogous method to Example 17 from the indicated starting materials.

| Ex | Compound | Structure | Data | SM |
|---|---|---|---|---|
| 89 | 2-(6-{[(ethylamino)-carbonyl]amino}pyridin-3-yl)-4-[1-(2-methoxyethyl)-1H-imidazol-2-yl]-1,3-thiazole-5-carboxylic acid | 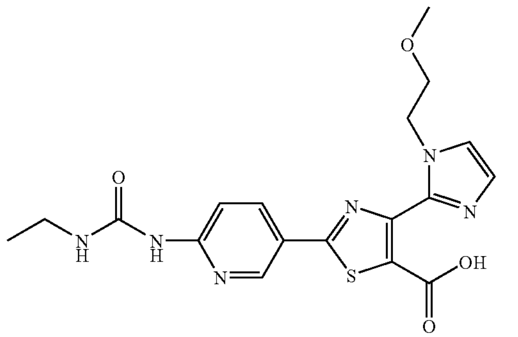 | MS (ESP): 417 (M + 1) for $C_{18}H_{20}N_6O_4S$; NMR: 1.09 (t, 3H); 3.15-3.23 (m, 2H); 3.23 (s, 3H); 3.80 (t, 2H); 4.93 (t, 2H); 7.48 (s, 1H); 7.63 (t, 2H); 7.83 (brs, 1H); 8.29 (dd, 1H); 8.86 (s, 1H); 9.58 (s, 1H); | Example 71 and 2N LiOH |
| 90 | 2-(6-{[(Ethylamino)-carbonyl]amino}pyridin-3-yl)-4-(1-methyl-1H-1,2,4-triazol-5-yl)-1,3-thiazole-5-carboxylic acid | 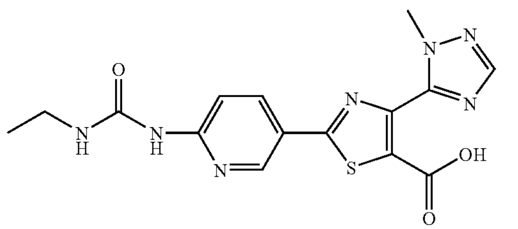 | MS (ES) MH$^-$: 372 for $C_{15}H_{15}N_7O_3S$; NMR: 1.09 (t, 3H); 3.15-3.24 (m, 2H); 4.05 (s, 3H); 7.56 (d, 1H); 7.79 (t, 1H); 8.26 (s, 1H); 8.32 (dd, 1H); 8.89 (d, 1H); 9.59 (s, 1H) | Example 72 and 2N LiOH |
| 91 | 2-(6-{[(Ethylamino)-carbonyl]amino}pyridin-3-yl)-4-{[(2-methoxyethyl)-amino]carbonyl}-1,3-thiazole-5-carboxylic acid | 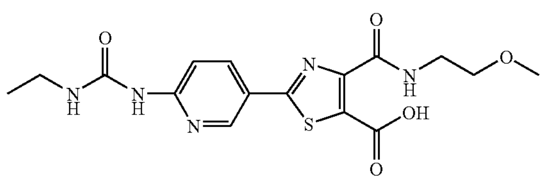 | MS (ES) MH$^+$: 394 for $C_{16}H_{19}N_5O_5S$; NMR: 1.08 (t, 3H); 3.14-3.23 (m, 2H); 3.27 (s, 3H); 3.53-3.56 (m, 4H); 7.63 (d, 1H); 7.71 (t, 1H); 8.37 (dd, 1H); 9.00 (d, 1H); 9.60 (s, 1H); 9.78 (brs, 1H) | Example 73 and 2N LiOH |
| 92 | 2-(6-{[(ethylamino)-carbonyl]amino}pyridin-3-yl)-4-({[(1S)-2-methoxy-1-methylethyl]-amino}carbonyl)-1,3-thiazole-5-carboxylic acid | 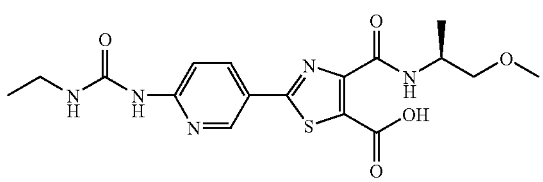 | MS (ES) MH$^+$: 408 for $C_{17}H_{21}N_5O_5S$; NMR: 1.09 (t, 3H); 1.22 (d, 3H); 3.14-3.22 (m, 2H); 3.27 (s, 3H); 3.37-3.45 (m, 3H); 3.50-3.56 (m, 1H); 4.29-4.36 (m, 1H); 7.64 (d, 1H); 7.76 (t, 1H); 8.39 (dd, 1H); 9.03 (d, 1H); 9.38 (d, 1H); 9.62 (s, 1H). | Example 74 and 2N LiOH |
| 93 | 2-(6-{[(Ethylamino)-carbonyl]amino}pyridin-3-yl)-4-(1-methyl-1H-imidazol-2-yl)-1,3-thiazole-5-carboxylic acid | 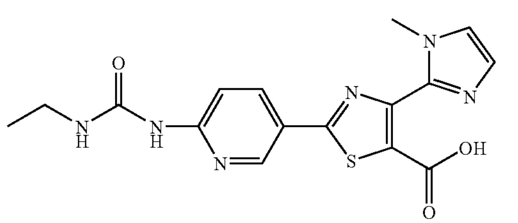 | MS (ES) MH$^+$: 373 for $C_{16}H_{16}N_6O_3S$; NMR: 1.09 (t, 3H); 3.14-3.24 (m, 2H); 4.22 (s, 3H); 7.51 (s, 1H); 7.62 (d, 1H); 7.67 (s, 1H); 7.86 (t, 1H); 8.33 (dd, 1H); 8.90 (d, 1H); 9.58 (s, 1H). | Example 75 and 2N LiOH |
| 94 | 4-[(tert-Butylamino)carbonyl]-2-(6-{[(ethylamino)-carbonyl]amino}pyridin-3-yl)-1,3-thiazole-5-carboxylic acid | 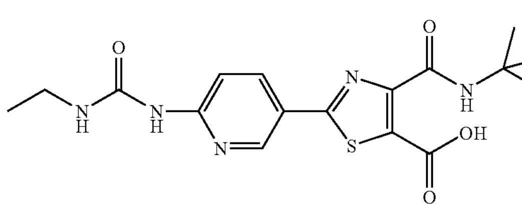 | MS (ES) MH$^+$: 392 for $C_{17}H_{21}N_5O_4S$; NMR: 1.09 (t, 3H); 1.45 (s, 9H); 3.14-3.22 (m, 2H); 7.62 (d, 1H); 7.78 (t, 1H); 8.38 (dd, 1H); 8.66 (s, 1H); 8.99 (d, 1H) 9.60 (s, 1H). | Example 76 and 2N LiOH |

| Ex | Compound | Structure | Data | SM |
|---|---|---|---|---|
| 95 | 6'-{[(Ethylamino)-carbonyl]amino}-4'-phenyl-3,3'-bipyridine-5-carboxylic acid | 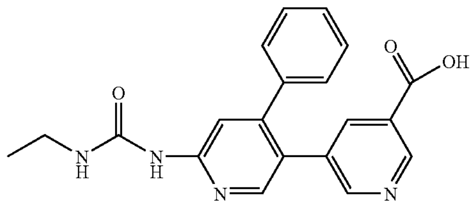 | MS (ESP): 363 (M + 1) for C₂₀H₁₈N₄O₃; NMR: 1.09 (t, 3H); 3.14-3.22 (m, 2H); 7.11-7.15 (m, 2H); 7.32-7.34 (m, 3H); 7.53 (s, 1H); 7.90 (br s, 1H); 7.92 (s, 1H); 8.30 (s, 1H); 8.44 (d, 1H); 8.87 (s, 1H); 9.40 (s, 1H) | Example 77 and 2N LiOH |
| 96 | 3-(6-{[(Ethylamino)-carbonyl]amino}-4-phenylpyridin-3-yl)benzoic acid | 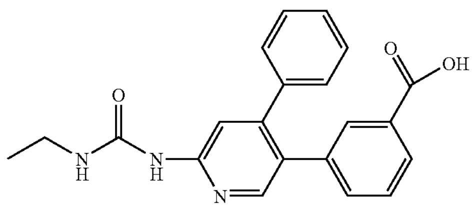 | MS (ESP): 362 (M + 1) for C₂₁H₁₉N₃O₃S; NMR: 1.09 (t, 3H); 3.14-3.22 (m, 2H); 7.09-7.13 (m, 2H); 7.28-7.38 (m, 5H); 7.49 (s, 1H); 7.66 (s, 1H); 7.78 (sd, 1H); 7.95 (br s, 1H); 8.2 (s, 1H); 9.35 (s, 1H). | Example 78 and 2N LiOH |
| 97 | 2-(6-{[(Ethylamino)-carbonyl]amino}-4-phenylpyridin-3-yl)-1,3-thiazole-5-carboxylic acid | 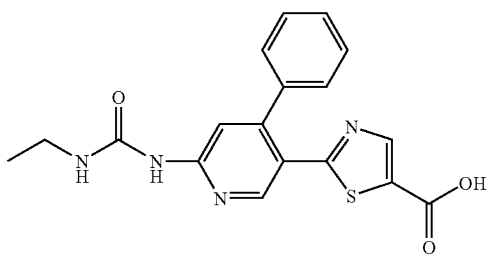 | MS (ESP): 367 (M + 1) for C₁₈H₁₆N₄O₃S; NMR: 1.08 (t, 3H); 3.14-3.20 (m, 2H); 7.28-7.31 (m, 2H); 7.45-7.52 (m, 4H); 7.69 (s, 1H); 8.27 (s, 1H); 8.85 (s, 1H); 9.55 (s, 1H); 13.46 (s, 1H). | Example 79 and 2N LiOH |
| 98 | 4-[(Butylamino)-carbonyl]-2-(6-{[(ethylamino)-carbonyl]amino}-4-phenylpyridin-3-yl)-1,3-thiazole-5-carboxylic acid | 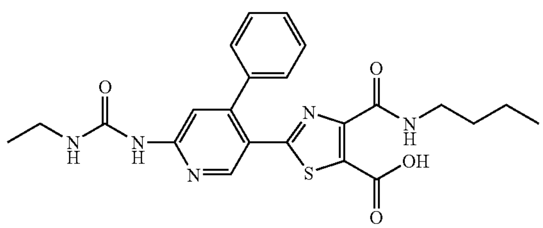 | MS (ESP): 496 (M + 1) for C₂₅H₂₉N₅O₄S; NMR: 0.90 (t, 3H); 1.08 (t, 3H); 1.31-1.35 (m, 2H); 1.54-1.58 (m, 2H); 3.16-3.23 (m, 4H); 7.32-7.37 (m, 2H); 7.47 (s, 1H); 7.55-7.62 (m, 3H); 7.72 (s, 1H); 9.30 (brs, 1H); 9.64 (s, 1H); 9.76 (s, 1H). | Example 80 and 2N LiOH |
| 99 | 6'-{[(Ethylamino)-carbonyl]amino}-4'-(4-ethyl-1,3-thiazol-2-yl)-3,3'-bipyridine-5-carboxylic acid | 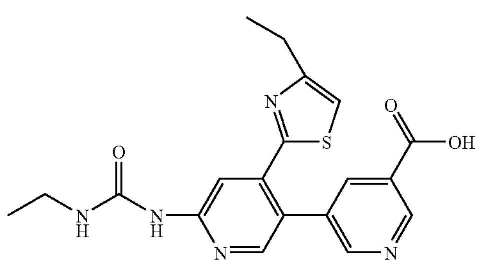 | MS (ES) MH⁺: 397 for C₁₉H₁₉N₅O₃S; NMR: 1.05 (t, 3H); 1.11 (t, 3H); 2.62 (q, 2H); 3.18-3.24 (m, 2H); 7.40 (s, 1H); 7.67 (br s, 1H); 8.11 (d, 2H); 8.30 (s, 1H); 8.68 (s, 1H); 9.05 (s, 1H); 9.45 (s, 1H); 13.46 (s, 1H). | Example 81 and 2N LiOH |
| 100 | 3-[6-{[(Ethylamino)-carbonyl]amino}-4-(4-ethyl-1,3-thiazol-2-yl)pyridin-3-yl]benzoic acid | 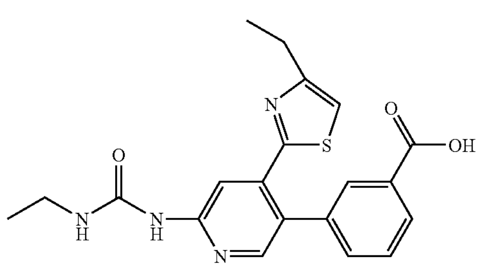 | MS (ESP): 397 (M + 1) for C₂₀H₂₀N₄O₃S; NMR: 1.11 (t, 3H); 1.31 (t, 3H); 2.54 (q, 2H); 3.18-3.24 (m, 2H); 7.34 (s, 1H); 7.46-7.52 (m, 2H); 7.78 (s, 2H); 7.94 (d, 1H); 8.13 (s, 2H); 8.20 (s, 1H); 9.39 (s, 1H) | Example 82 and 2N LiOH |

-continued

| Ex | Compound | Structure | Data | SM |
|---|---|---|---|---|
| 101 | 6'-{[(Ethylamino)-carbonyl]amino}-4'-[4-(trifluoromethyl)-1,3-thiazol-2-yl]-3,3'-bipyridine-5-carboxylic acid | 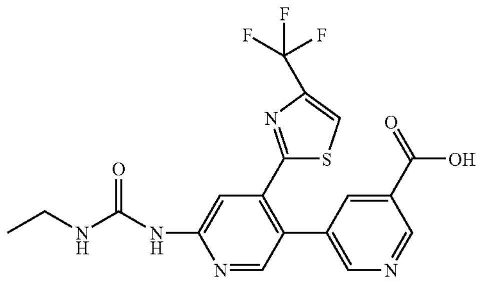 | MS (ES) MH+: 437 for $C_{18}H_{14}F_3N_5O_3S$; NMR: 1.11 (t, 3H); 3.18-3.24 (m, 2H); 7.57 (brs, 1H); 8.15-8.18 (m, 1H); 8.22 (s, 1H); 8.37 (s, 1H); 8.57 (s, 1H); 8.72 (s, 1H); 9.08 (s, 1H); 9.51 (s, 1H); 13.53 (s, 1H) | Example 83 and 2N LiOH |
| 102 | 2-{6-{[(Ethylamino)-carbonyl]amino}-4-[4-(trifluoromethyl)-1,3-thiazol-2-yl]pyridin-3-yl}-1,3-thiazole-5-carboxylic acid | 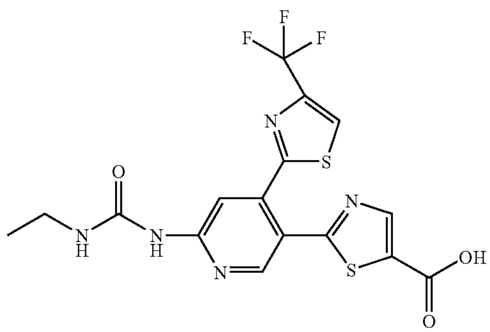 | MS (ES) MH+: 444 for $C_{16}H_{12}F_3N_5O_3S_2$; NMR: 1.09 (t, 3H); 3.16-3.24 (m, 2H); 7.50 (s, 1H); 8.09 (s, 1H); 8.25 (s, 1H); 8.68 (d, 2H); 9.67 (s, 1H) | Example 84 and 2N LiOH |
| 103 | 6'-{[(Ethylamino)-carbonyl]amino}-3,3':4',3''-terpyridine-5-carboxylic acid | 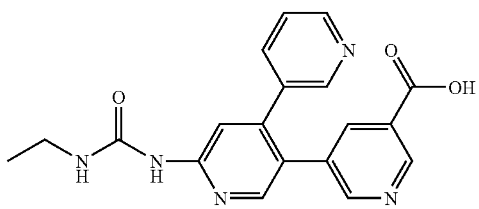 | MS (ESP): 364 (M + 1) for $C_{19}H_{17}N_5O_3$; NMR: 1.09 (t, 3H); 3.14-3.24 (m, 2H); 7.35-7.39 (m, 1H), 7.57 (d, 1H); 7.66 (s, 1H); 7.94-7.95 (m, 2H); 8.31-8.33 (m, 3H); 8.51 (d, 1H); 8.88 (d, 1H); 9.54 (s, 1H) | Example 85 and 2N LiOH |
| 104 | 6'-{[(Ethylamino)-carbonyl]amino}-3,3':4',3''-terpyridine-5-carboxylic acid | 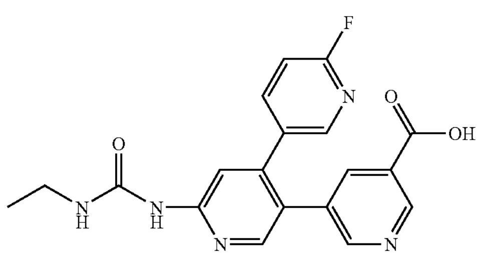 | MS (ESP): 382 (M + 1) for $C_{19}H_{16}FN_5O_3$; NMR: 1.11 (t, 3H); 1.29 (t, 3H); 3.15-3.24 (m, 2H), 4.31 (q, 2H), 7.19 (dd, 1H), 7.63 (s, 1H); 7.77-7.83 (m, 2H); 7.99 (s, 1H), 8.08 (d, 1H); 8.39 (s, 1H); 8.57 (d, 1H); 8.96 (s, 1H); 9.46 (s, 1H) | Example 86 and 2N LiOH |
| 105 | 6'-{[(Isopropylamino)-arbonyl]amino}-4'-[4-(trifluoromethyl)-1,3-thiazol-2-yl]-3,3'-bipyridine-5-carboxylic acid | 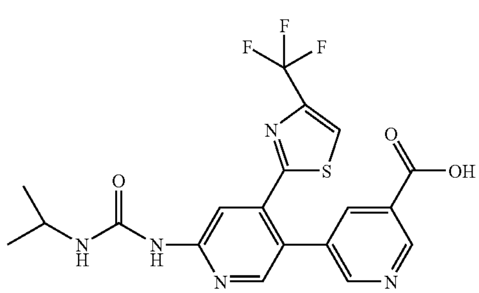 | MS (ES) MH+: 452 for $C_{19}H_{16}F_3N_5O_3S$; NMR: 1.14 (d, 6H); 3.79-3.81 (m, 1H) 7.53 (s, 1H); 8.04 (s, 1H); 8.28 (s, 2H); 8.40 (s, 1H); 8.51 (s, 1H); 8.99 (d, 1H); 9.39 (s, 1H) | Example 87 and 2N LiOH |

| Ex | Compound | Structure | Data | SM |
|---|---|---|---|---|
| 106 | 6'-{[(Sec-butylamino)carbonyl]amino}-4'-[4-(trifluoromethyl)-1,3-thiazol-2-yl]-3,3'-bipyridine-5-carboxylic acid | 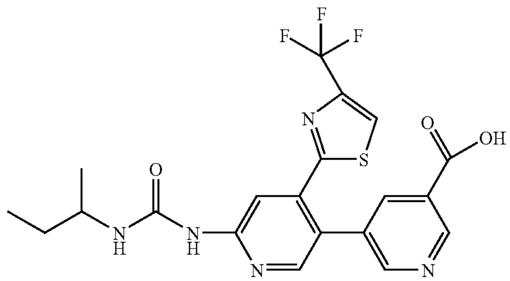 | MS (ES) MH+: 466 for $C_{20}H_{18}F_3N_5O_3S$; NMR: 0.89 (t, 3H); 1.11 (d, 3H); 1.40-1.49 (m, 2H); 3.58-3.81 (m, 1H) 7.43 (d, 1H); 8.00-8.17 (m, 1H); 8.23 (s, 1H); 8.35 (s, 1H); 8.55 (s, 1H); 8.67 (s, 1H); 9.06 (d, 1H); 9.37 (s, 1H) | Example 88 and 2N LiOH |

Example 107

6'-{[(Ethylamino)carbonyl]amino}-4'-(4-ethyl-1,3-thiazol-2-yl)-N-methyl-3,3'-bipyridine-5-carboxamide

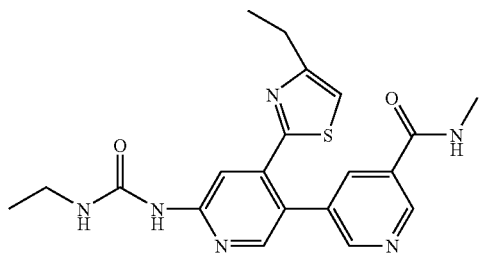

Triethylamine (30.6 mg, 0.30 mmol) and methanamine (0.075 mL, 0.15 mmol), (2M soln in methanol) were added to a solution of 4'-(4-ethylthiazol-2-yl)-6'-(3-ethylureido)-3,3'-bipyridine-5-carboxylic acid (Example 99, 60 mg, 0.15 mmol) in DMF (1.5 mL). The solution was stirred for 10 minutes and then 2-(3H-[1,2,3]triazolo[4,5-b]pyridin-3-yl)-1,1,3,3-tetramethylisouronium hexafluorophosphate(V) (57.4 mg, 0.15 mmol) was added. The resulting light yellow solution was stirred at room temperature for one hour. A small aliquat was withdrawn and analyzed by LCMS. Since the reaction was not complete, one more equivalent of methylamine solution and HATU were added. The analysis and addition of methylamine and HATU was repeated 3-4 times, however, the reaction did not go to completion. It was then diluted with water and extracted with ethylacetate 2-3 times. The extract was washed with water (3 times), brine and dried over magnesium sulfate, then concentrated to give the title compound as an off-white solid, which was triturated with acetonitrile and lyophilized to remove excess solvent (15 mg). MS (ES) MH+: 411 for $C_{20}H_{22}N_6O_2S$; NMR: 1.08 (t, 3H); 1.11 (t, 3H); 2.64 (q, 2H); 2.79 (d, 3H); 3.17-3.22 (m, 2H); 7.40 (s, 1H); 7.66 (s, 1H); 8.12 (d, 1H); 8.16 (s, 1H); 8.28 (s, 1H); 8.55 (s, 1H); 8.68 (s, 1H); 8.99 (d, 1H); 9.02 (s, 1H); 9.44 (s, 1H).

Example 108-130

The following compounds were made by an analogous method to Example 107 from the starting material indicated.

| Ex | Compound | Structure | Data | SM |
|---|---|---|---|---|
| 108 | N4-Butyl-2-(6-{[(ethylamino)-carbonyl]amino}pyridin-3-yl)-N5-methyl-1,3-thiazole-4,5-dicarboxamide | 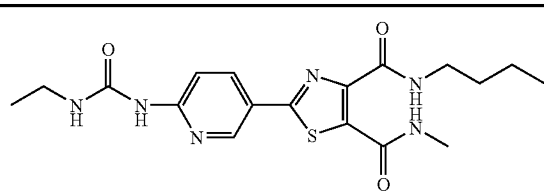 | MS (ESP): 405 (M + 1) for $C_{18}H_{24}N_6O_3S$; NMR: 0.91 (s, 3H); 1.09 (s, 3H); 1.29-1.36 (m, 2H); 1.53-1.57 (m, 2H); 2.84 (d, 3H); 7.58 (d, 1H), 7.77 (br s, 1H); 8.35 (d, 1H); 8.99 (s, 1H); 9.25 (br s, 1H); 9.55 (s, 1H); 11.26 (s, 1H). | Example 26 and methyl amine (2M solution in THF) |
| 109 | N4-Butyl-2-(6-{[(ethylamino)-carbonyl]amino}pyridin-3-yl)-N5,N5-dimethyl-1,3-thiazole-4,5-dicarboxamide | 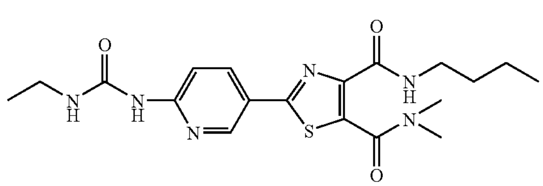 | MS (ES) MH+: 419 for $C_{19}H_{26}N_6O_3S$; NMR: 0.89 (s, 3H); 1.09 (s, 3H); 1.27-1.36 (m, 2H); 1.46-1.54 (m, 2H); 2.82 (s, 3H); 2.98 (s, 3H); 3.16-3.25 (m, 4H); 7.62 (d, 1H), 7.74 (br s, 1H); 8.28 (dd, 1H); 8.61 (t, 1H); 8.88 (d, 1H); 9.54 (s, 1H). | Example 26 and dimethylamine (2M solution in THF) |

-continued

| Ex | Compound | Structure | Data | SM |
|---|---|---|---|---|
| 110 | N⁴-(tert-Butyl)-2-(6-{[(ethylamino)-carbonyl]amino}pyridin-3-yl)-N⁵,N⁵-dimethyl-1,3-thiazole-4,5-dicarboxamide | 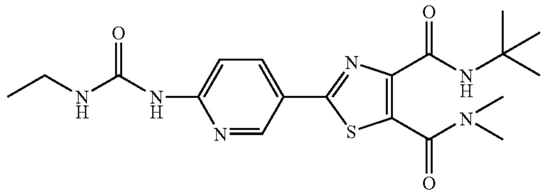 | MS (ES) MH⁺: 419 for $C_{19}H_{26}N_6O_3S$; NMR: 1.09 (s, 3H); 1.39 (s, 9H); 2.83 (s, 3H); 2.99 (s, 3H); 3.16-3.22 (m, 2H); 7.58 (d, 1H), 7.71 (s, 1H); 7.85 (br s, 1H); 8.29 (dd, 1H); 8.87 (d, 1H); 9.56 (s, 1H). | Example 94 and dimethylamine (2M solution in THF) |
| 111 | N⁴-(tert-Butyl)-2-(6-{[(ethylamino)-carbonyl]amino}pyridin-3-yl)-1,3-thiazole-4,5-dicarboxamide | 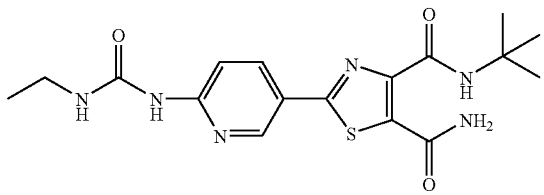 | MS (ES) MH⁺: 391 for $C_{17}H_{22}N_6O_3S$; NMR: 1.09 (s, 3H); 1.43 (s, 9H); 3.16-3.22 (m, 2H); 7.58 (d, 1H), 7.85 (br s, 1H); 8.07 (d, 1H), 8.29 (s, 1H), 8.33 (dd, 1H); 8.92 (d, 1H); 9.56 (s, 1H); 10.44 (d, 1H). | Example 94, cumyl amine followed by TFA |
| 112 | 2-(6-{[(Ethylamino)-carbonyl]amino}pyridin-3-yl)-N,N-dimethyl-4-(1-methyl-1H-imidazol-2-yl)-1,3-thiazole-5-carboxamide | 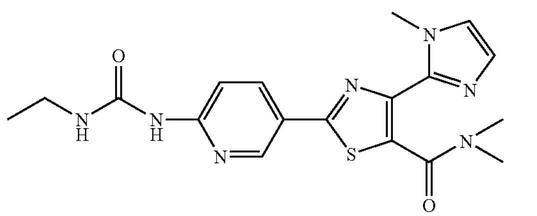 | MS (ES) MH⁺: 400 for $C_{18}H_{21}N_7O_2S$; NMR: 1.09 (t, 3H); 2.69 (s, 3H); 2.94 (s, 3H); 3.17-3.22 (m, 2H); 3.98 (s, 3H); 7.00 (s, 1H); 7.30 (s, 1H); 7.59 (d, 1H); 7.86 (t, 1H); 8.27 (dd, 1H); 9.53 (s, 1H). | Example 93 and dimethyl amine (2M solution in THF) |
| 113 | 2-(6-{[(Ethylamino)-carbonyl]amino}pyridin-3-yl)-N,N-dimethyl-4-(1-methyl-1H-1,2,4-triazol-5-yl)-1,3-thiazole-5-carboxamide | 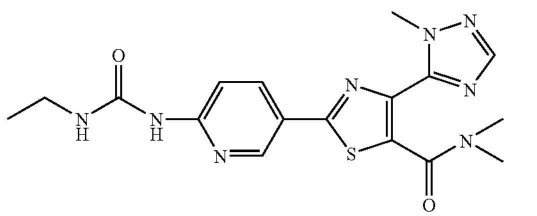 | MS (ES) MH⁻: 401 for $C_{17}H_{20}N_8O_2S$; NMR: 1.09 (t, 3H); 2.77 (s, 3H); 2.99 (s, 3H); 3.17-3.22 (m, 2H); 4.24 (s, 3H); 7.64 (d, 1H); 7.84 (t, 1H); 8.04 (s, 1H); 8.30 (dd, 1H); 8.88 (d, 1H); 9.56 (s, 1H) | Example 90 and dimethyl amine (2M solution in THF) |
| 114 | 6'-{[(Ethylamino)-carbonyl]amino}-4'-phenyl-3,3'-bipyridine-5-carboxamide | 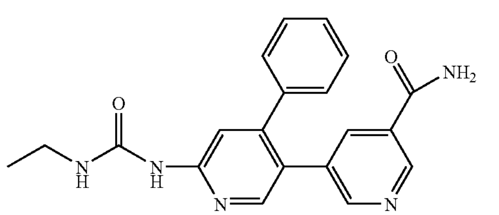 | MS (ESP): 362 (M + 1) for $C_{20}H_{19}N_5O_2$ ¹H-NMR (DMSO-d₆) δ: 1.11 (t, 3H); 3.18-3.22 (m, 2H); 7.13-7.16 (m, 3H); 7.32-7.35 (m, 3H); 7.55 (s, 1H); 7.60 (s, 1H); 7.88 (brs, 1H); 8.05 (s, 1H); 8.15 (s, 1H); 8.30 (d, 1H); 8.32 (d, 1H); 8.85 (s, 1H); 9.42 (s, 1H) | Example 95 and cumylamine followed by TFA |
| 115 | 2-(6-{[(Ethylamino)-carbonyl]amino}pyridin-3-yl)-N⁴-methyl-1,3-thiazole-4,5-dicarboxamide | 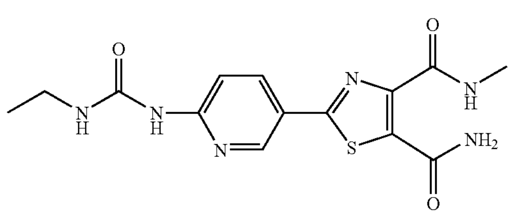 | MS (ESP): 349 (M + 1) for $C_{14}H_{16}N_6O_3S$; NMR: 1.09 (t, 3H); 2.85 (d, 3H); 3.16-3.22 (m, 2H); 7.61 (d, 1H); 7.75 (s, 1H); 8.05 (s, 1H); 8.34 (dd, 1H); 8.96 (s, 1H); 9.19 (d, 1H); 9.56 (s, 1H); 10.64 (s, 1H). | Example 24 and cumylamine followed by TFA |

-continued

| Ex | Compound | Structure | Data | SM |
|---|---|---|---|---|
| 116 | 2-(6-{[(Ethylamino)-carbonyl]amino}pyridin-3-yl)-$N^4$-(2-methoxyethyl)-1,3-thiazole-4,5-dicarboxamide | 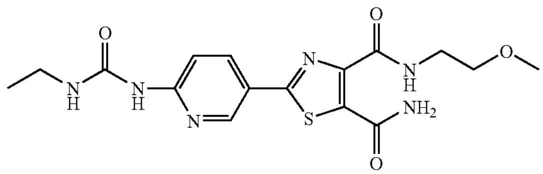 | MS (ES) MH$^+$: 393 for $C_{16}H_{20}N_6O_4S$; NMR: 1.09 (t, 3H); 3.16-3.23 (m, 2H); 3.27 (s, 3H); 3.50 (s, 4H); 7.69 (d, 1H); 7.77 (s, 1H); 8.07 (s, 1H); 8.34 (dd, 1H); 8.97 (d, 1H); 9.20 (s, 1H); 9.56 (s, 1H); 10.56 (s, 1H) | Example 91 and cumylamine followed by TFA |
| 117 | 2-(6-{[(Ethylamino)-carbonyl]amino}pyridin-3-yl)-$N^4$-[(1S)-2-methoxy-1-methylethyl]-1,3-thiazole-4,5-dicarboxamide | 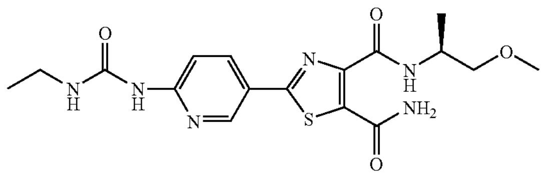 | MS (ES) MH$^+$: 407 for $C_{17}H_{22}N_6O_4S$; NMR: 1.09 (t, 3H); 1.19 (d, 3H) 3.15-3.22 (m, 2H); 3.28 (s, 3H); 3.37-3.45 (m, 1H); 3.49-3.54 (m, 1H); 4.21-4.31 (m, 1H); 7.60 (d, 1H); 7.83 (t, 1H); 8.07 (d, 1H); 8.36 (dd, 1H); 8.85 (d, 1H); 9.00 (d, 1H); 9.57 (s, 1H); 10.55 (d, 1H). | Example 92 and cumylamine followed by TFA |
| 118 | 2-(6-{[(Ethylamino)-carbonyl]amino}pyridin-3-yl)-$N^4$-[(1S)-2-methoxy-1-methylethyl]-$N^5,N^5$-dimethyl-1,3-thiazole-4,5-dicarboxamide | 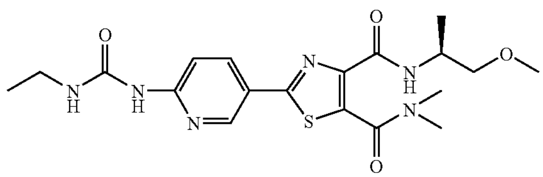 | MS (ES) MH$^+$: 435 for $C_{19}H_{26}N_6O_4S$; NMR: 1.09 (t, 3H); 1.15 (d, 3H); 2.83 (s, 3H); 2.98 (s, 3H); 3.18-3.22 (m, 2H); 3.26 (s, 3H); 3.30-3.34 (m, 1H); 3.42-3.46 (m, 1H); 4.16-4.19 (m, 1H); 7.61 (d, 1H); 7.78 (s, 1H); 8.28 (t, 2H); 8.90 (s, 1H); 9.56 (s, 1H) | Example 92 and dimethyl amine (2M solution in THF) |
| 119 | 6'-{[(Ethylamino)carbonyl]amino}-4'-(4-ethyl-1,3-thiazol-2-yl)-3,3'-bipyridine-5-carboxamide | 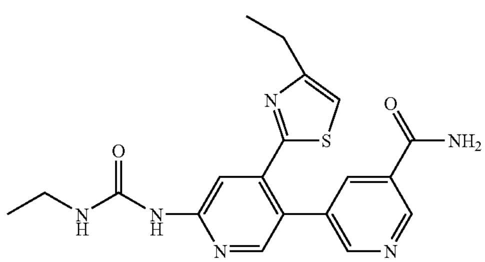 | MS (ES) MH$^+$: 397 for $C_{19}H_{20}N_6O_2S$; NMR: 1.08 (t, 3H); 1.11 (t, 3H); 2.64 (q, 2H); 3.17-3.22 (m, 2H); 7.40 (s, 1H); 7.64 (s, 1H); 7.65 (brs, 1H); 8.15 (s, 2H); 8.29 (s, 1H); 8.55 (s, 1H); 9.02 (s, 1H); 9.44 (s, 1H) | Example 99 and cumylamine followed by TFA |
| 120 | 6'-{[(Ethylamino)carbonyl]amino}-4'-(4-ethyl-1,3-thiazol-2-yl)-N-methyl-3,3'-bipyridine-5-carboxamide | 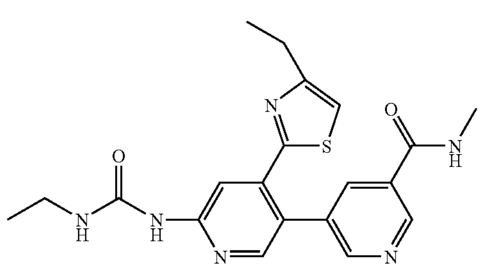 | MS (ES) MH$^+$: 411 for $C_{20}H_{22}N_6O_2S$; NMR: 1.08 (t, 3H); 1.11 (t, 3H); 2.64 (q, 2H); 2.79 (d, 3H); 3.17-3.22 (m, 2H); 7.40 (s, 1H); 7.66 (s, 1H); 8.12 (d, 1H); 8.16 (s, 1H); 8.28 (s, 1H); 8.55 (s, 1H); 8.68 (s, 1H); 8.99 (d, 1H); 9.02 (s, 1H); 9.44 (s, 1H) | Example 99 and 2M N-methylamine solution in THF |

-continued

| Ex | Compound | Structure | Data | SM |
|---|---|---|---|---|
| 121 | 6'-{[(Ethylamino)-carbonyl]amino}-4'-[4-(trifluoromethyl)-1,3-thiazol-2-yl]-3,3'-bipyridine-5-carboxamide | 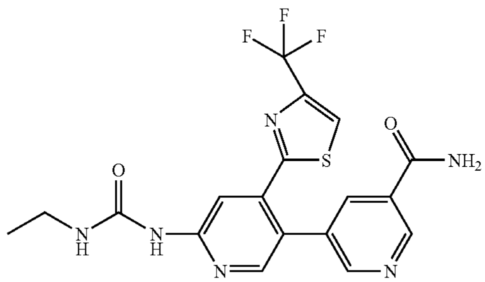 | MS (ES) MH$^+$: 437 for C$_{18}$H$_{15}$F$_3$N$_6$O$_2$S; NMR: 1.09 (t, 3H); 3.18-3.24 (m, 2H); 7.45 (brs, 1H); 7.65 (s, 1H); 8.16 (s, 1H); 8.18 (s, 1H); 8.24 (s, 1H); 8.35 (s, 1H); 8.55 (d, 1H); 8.60 (d, 1H); 9.05 (s, 1H); 9.49 (s, 1H) | Example 101 and cumylamine followed by TFA |
| 122 | 6'-{[(Ethylamino)-carbonyl]amino}-N-methyl-4'-[4-(trifluoromethyl)-1,3-thiazol-2-yl]-3,3'-bipyridine-5-carboxamide | 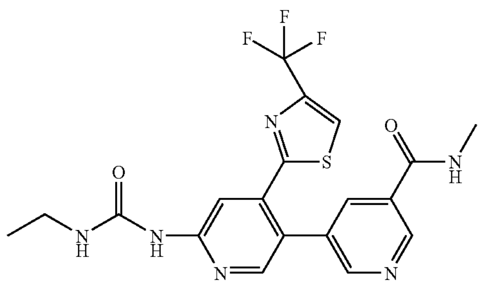 | MS (ES) MH$^+$: 451 for C$_{19}$H$_{17}$F$_3$N$_6$O$_2$S; NMR: 1.09 (t, 3H); 2.78 (d, 3H); 3.16-3.22 (m, 2H); 7.50 (br s, 1H); 8.15 (d, 1H); 8.24 (s, 1H); 8.34 (s, 1H); 8.55 (s, 1H); 8.59 (d, 1H); 8.65 (d, 1H); 9.01 (s, 1H); 9.48 (s, 1H) | Example 101 and methyl amine (2M solution in THF) |
| 123 | N-(tert-Butyl)-6'-{[(ethylamino)-carbonyl]amino}-4'-[4-(trifluoromethyl)-1,3-thiazol-2-yl]-3,3'-bipyridine-5-carboxamide | 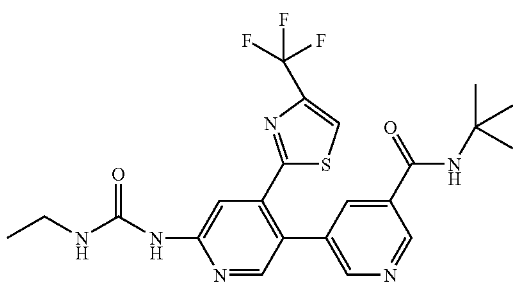 | MS (ES) MH$^+$: 492 for C$_{22}$H$_{23}$F$_3$N$_6$O$_2$S; NMR: 1.09 (t, 3H); 1.37 (s, 9H); 3.12-3.22 (m, 2H); 7.55 (brs, 1H); 7.99 (s, 1H); 8.17 (t, 1H); 8.23 (s, 1H); 8.36 (s, 1H); 8.52-8.58 (m, 2H); 8.97 (d, 1H); 9.48 (s, 1H) | Example 101 and tert-butyl amine |
| 124 | 6'-{[(Ethylamino)-carbonyl]amino}-N-[(1S)-2-methoxy-1-methylethyl]-4'-[4-(trifluoromethyl)-1,3-thiazol-2-yl]-3,3'-bipyridine-5-carboxamide | 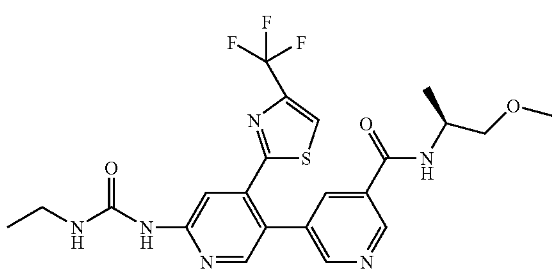 | MS (ES) MH$^+$: 509 for C$_{22}$H$_{23}$F$_3$N$_6$O$_3$S; NMR: 1.09 (t, 3H); 1.11 (d, 3H); 3.15-3.21 (m, 2H); 3.24 (s, 3H); 3.25-3.30 (m, 1H);; 3.34-3.41 (m, 1H); 4.14-4.27 (m, 1H); 7.59 (brs, 1H); 8.15-8.20 (m, 1H); 8.23 (s, 1H); 8.36 (s, 1H); 8.43-8.45 (m, 1H); 8.55 (s, 1H); 9.01 (d, 1H); 9.48 (s, 1H) | Example 101 and [(1S)-2-methoxy-1-methylethyl]-amine |
| 125 | N-Cyclopentyl-6'-{[(ethylamino)-carbonyl]amino}-4'-[4-(trifluoromethyl)-1,3-thiazol-2-yl]-3,3'-bipyridine-5-carboxamide | 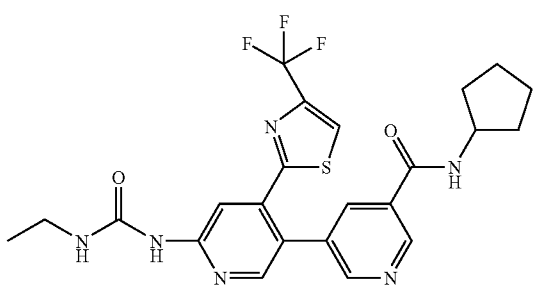 | MS (ES) MH$^+$: 505 for C$_{23}$H$_{23}$F$_3$N$_6$O$_3$S; NMR: 1.09 (t, 3H); 1.39-1.61 (m, 4H); 1.60-1.77 (m, 2H); 1.79-1.95 (m, 2H); 3.16-3.26 (m, 2H); 4.18-4.26 (m, 1H); 7.54 (t, 1H); 8.14-8.21 (m, 1H); 8.24 (s, 1H); 8.36 (s, 1H); 8.47 (d, 1H); 8.56 (dd, 1H); 9.01 (d, 1H); 9.49 (s, 1H) | Example 101 and cyclopentane-amine |

-continued

| Ex | Compound | Structure | Data | SM |
|---|---|---|---|---|
| 126 | N-Cyclopropyl-6'-{[(ethylamino)-carbonyl]amino}-4'-[4-(trifluoromethyl)-1,3-thiazol-2-yl]-3,3'-bipyridine-5-carboxamide | 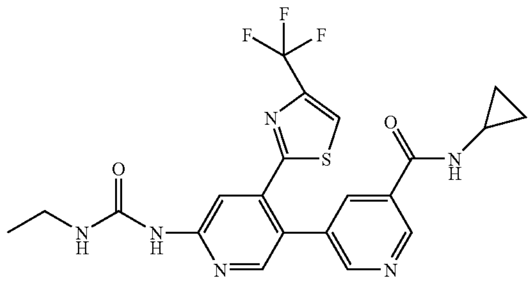 | MS (ES) MH+: 477 for $C_{21}H_{19}F_3N_6O_2S$; NMR: 0.49-0.61 (m, 2H); 0.64-0.82 (m, 2H); 1.09 (t, 3H); 2.77-2.97 (m, 1H); 3.17-3.24 (m, 2H); 7.53 (t, 1H); 8.14 (m, 1H); 8.23 (s, 1H); 8.34 (s, 1H); 8.54-8.59 (m, 2H); 8.64 (d, 1H); 8.99 (d, 1H); 9.48 (s, 1H) | Example 101 and cyclopropylamine |
| 127 | 2-{6-{[(Ethylamino)-carbonyl]amino}-4-[4-(trifluoromethyl)-1,3-thiazol-2-yl]pyridin-3-yl}-N-methyl-1,3-thiazole-5-carboxamide | 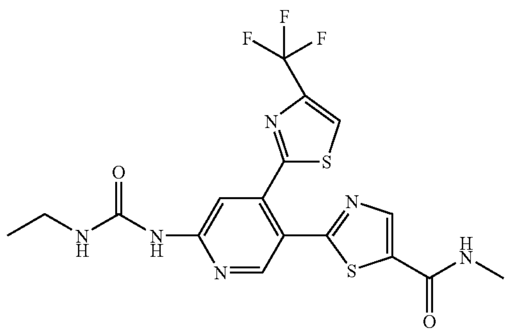 | MS (ES) MH+: 457 for $C_{17}H_{15}F_3N_6O_2S_2$; NMR: 1.09 (t, 3H); 2.76 (d, 3H); 3.17-3.24 (m, 2H); 7.48 (t, 1H); 8.08 (s, 1H); 8.32 (s, 1H); 8.65 (s, 1H); 8.68 (s, 1H); 8.70 (s, 1H); 9.64 (s, 1H) | Example 102 and methyl amine (2M solution in THF) |
| 128 | 6'-{[(Ethylamino)-carbonyl]amino}-6''-fluoro-3,3':4',3''-terpyridine-5-carboxamide | 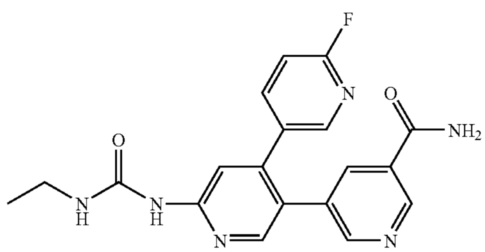 | MS (ESP): 381 (M + 1) for $C_{19}H_{17}FN_6O_2$; $^1$H-NMR (DMSO-$d_6$) δ: 1.09 (t, 3H); 3.18-3.22 (m, 2H); 7.12 (dd, 1H); 7.57 (s, 2H); 7.65-7.73 (m, 2H); 7.96-7.99 (m, 2H); 8.07 (s, 1H); 8.30 (s, 1H); 8.32 (d, 1H); 8.83 (d, 1H); 9.39 (s, 1H) | Example 104 and cumylamine followed by TFA |
| 129 | 6'-{[(Isopropyl-amino)carbonyl]-amino}-N-methyl-4'-[4-(trifluoromethyl)-1,3-thiazol-2-yl]-3,3'-bipyridine-5-carboxamide | 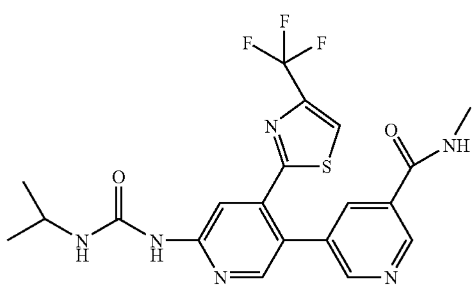 | MS (ES) MH+: 465 for $C_{20}H_{19}F_3N_6O_2S$; NMR: 1.17 (d, 6H); 2.79 (d, 3H); 3.80-3.84 (m, 1H); 7.40 (d, 1H); 8.16 (d, 1H); 8.27 (s, 1H); 8.35 (s, 1H); 8.56 (s, 1H); 8.59 (d, 1H); 8.68 (d, 1H); 9.01 (s, 1H); 9.36 (s, 1H) | Example 105 and methyl amine (2M solution in THF) |
| 130 | 6'-{[(Sec-butylamino)car-bonyl]amino}-N-methyl-4'-[4-(trifluoromethyl)-1,3-thiazol-2-yl]-3,3'-bipyridine-5-carboxamide | 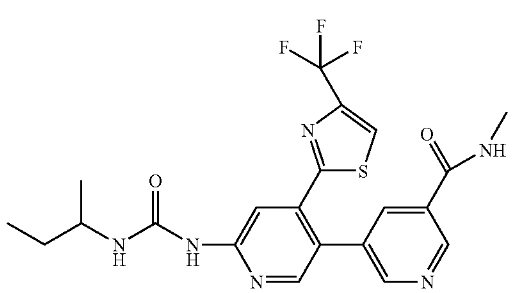 | MS (ES) MH+: 479 for $C_{21}H_{21}F_3N_6O_2S$; NMR: 0.90 (t, 3H); 1.12 (d, 3H); 1.46-1.52 (m, 2H); 2.80 (d, 3H); 3.66-3.73 (m, 2H); 7.42 (d, 1H); 8.16 (d, 1H); 8.28 (s, 1H); 8.36 (s, 1H); 8.56 (d, 1H); 8.68 (d, 1H); 9.03 (s, 1H); 9.39 (s, 1H) | Example 106 and methyl amine (2M solution in THF) |

Example 131

6'-(3-Ethyl-ureido)-[2,3']bipyridinyl-4,5-dicarboxylic acid 5-dimethyl amide 4-isopropylamide

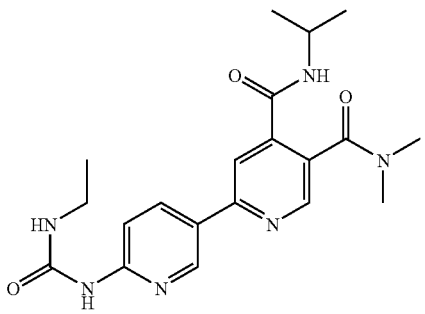

In a 80 mL microwave vessel, N-ethyl-N'-[5-(4,4,5,5-tetramethyl-[1,3,2]dioxaborolan-2-yl)-pyridin-2-yl]-urea (Intermediate 1, 0.6 g, 2.23 moles), 6-chloro-pyridine-3,4-dicarboxylic acid 3-dimethylamide 4-isopropylamide (Intermediate 64, 0.65 g, 2.23 moles), and cesium carbonate (0.724 g, 2.23 mM), Pd(PPh$_3$)$_4$ (0.257 g, 0.223 moles) were taken up in dioxane:water (4:1) (15 mL) and degassed for 30 min. The reaction mixture was heated to 100° C. for 30 min via microwave heat. The reaction mixture was diluted with ethyl acetate (30 mL) and water (30 mL), and the organic and aqueous layers were separated. The aqueous layer was extracted with ethyl acetate (2×25 mL) and the extracts were added to the organic layer, then dried over sodium sulfate, and concentrated under reduced pressure. Purification by column chromatography (silica, 4% methanol in dichloromethane) provided a solid residue. The residue was stirred in ethyl acetate (5 mL) for 20 min, then filtered to obtain 0.098 g (11.04%) of the title compound as white solid. MS (ESP): 398 (MH$^+$) for C$_{20}$H$_{26}$N$_6$O$_3$; NMR: 1.11 (t, 3H), 1.17 (d, 6H), 2.8 (s, 3H), 2.97 (s, 3H), 3.21 (q, 2H), 4.02 (m, 1H), 7.56 (d, 1H), 7.96 (br s, 1H), 8.069 (s, 1H), 8.410 (d, 1H), 8.49 (s, 1H), 8.54 (s, 1H), 8.97 (s, 1H), 9.40 (s, 1H).

Example 131

Ethyl 6'-{[(ethylamino)carbonyl]amino}-4'-(4-phenyl-1,3-thiazol-2-yl)-3,3'-bipyridine-5-carboxylate

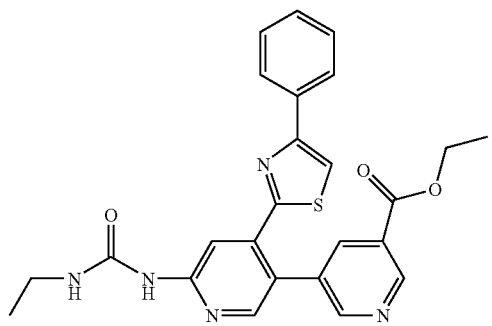

N-[5-bromo-4-(4-phenyl-1,3-thiazol-2-yl)pyridin-2-yl]-N'-ethylurea (Intermediate 69, 0.17 g, 0.42 mmol), ethyl 5-(4,4,5,5-tetramethyl-1,3,2-dioxaborolan-2-yl)nicotinate (0.14 g, 0.51 mmol), tetrakis triphenyl phosphine palladium (0.024 g, 0.02 mmol), and cesium carbonate (0.165 g, 0.51 mmol) were combined in a microwave vial and degassed with nitrogen. 1,4-dioxane:water (4:1, 2.5 mL) was added to the mixture and the reaction mixture was heated to 100° C. for 60 minutes. The reaction mixture was partitioned between water and ethyl acetate and the layers separated. The organic layer was washed with saturated NaHCO$_3$, water, and brine, then dried over magnesium sulfate. The organic layer was concentrated to form a precipitate, and the resulting solids were filtered and then washed with acetonitrile followed by chloroform to yield 200 mg of the title compound as an off-white solid. LC/MS (ES$^+$)[(M+H)$^+$]: 474 for C$_{25}$H$_{23}$N$_5$O$_3$S. $^1$H NMR (300 MHz, CHCl$_3$): 1.28 (t, 3H), 1.39 (t, 3H), 3.44-3.49 (m, 2H), 4.41 (q, 2H), 7.31-7.39 (m, 2H), 7.52 (s, 1H), 7.62 (d, 2H), 8.17 (s, 1H), 8.28 (t, 1H), 8.32 (t, 1H), 8.4 (s, 1H), 8.71 (d, 1H), 8.73 (d, 1H), 9.23 (d, 1H), 9.27 (s, 1H).

Example 132

6'-{[(Ethylamino)carbonyl]amino}-4'-(4-phenyl-1,3-thiazol-2-yl)-3,3'-bipyridine-5-carboxylic acid

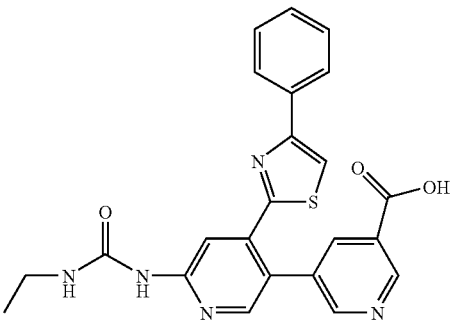

In a 25 mL round-bottomed flask ethyl 6'-{[(ethylamino)carbonyl]amino}-4'-(4-phenyl-1,3-thiazol-2-yl)-3,3'-bipyridine-5-carboxylate (Example 131, 0.20 g, 0.42 mmol) was suspended in THF (3 mL). 1N LiOH (1.20 mL, 1.21 mmol) was added and the solution was stirred at room temperature overnight. The solvent was removed and the resulting residue was diluted with water. The pH was adjusted to 4 (pH paper) with 2N HCl. White solids formed. They were trichurated with acetonitrile for 30 minutes and then filtered, washed with acetonitrile and dried in vacuo to give 58 mg of the title compound. LC/MS (ES$^+$)[(M+H)$^+$]: 446 for C$_{23}$H$_{11}$N$_5$O$_3$S. $^1$H NMR (300 MHz, d$_6$-DMSO): 1.10 (t, 3H), 3.21 (m, 2H), 7.32-7.40 (m, 3H), 7.65 (t, 1H), 7.70 (s, 1H), 7.72 (s, 1H), 8.22 (s, 1H), 8.23-8.26 (m, 2H), 8.31 (s, 1H), 8.73 (d, 1H), 9.08 (d, 1H), 9.45 (s, 1H).

Example 133

6'-{[(ethylamino)carbonyl]amino}-N-methyl-4'-(4-phenyl-1,3-thiazol-2-yl)-3,3'-bipyridine-5-carboxamide

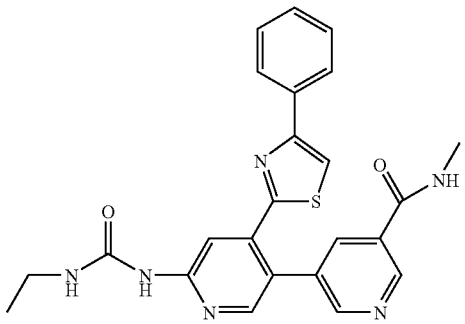

2-(3H-[1,2,3]triazolo[4,5-b]pyridin-3-yl)-1,1,3,3-tetramethylisouronium hexafluorophosphate(V) (73.7 mg, 0.19 mmol), DIEA (78.6 mg, 0.45 mmol) and methylamine (2M soln in THF, 0.15 mL, 0.30 mmol) were added to a solution of 6'-{[(ethylamino)carbonyl]amino}-4'-(4-phenyl-1,3-thiazol-2-yl)-3,3'-bipyridine-5-carboxylic acid (Example 132, 66.4 mg, 0.15 mmol) in DMF (1.5 mL). The resulting light yellow solution was stirred at room temperature for three hours. The reaction mixture was partitioned between water and ethyl acetate and layers separated. The organic layer was washed with saturated $NaHCO_3$, water, brine, then dried over magnesium sulfate. The solvent was removed and the resulting residue was washed with acetonitrile and filtered to yield 33 mg of the title compound.

LC/MS (ES$^+$)[(M+H)]: 459 for $C_{24}H_{22}N_6O_2S$. $^1$H NMR (300 MHz, d$_6$-DMSO): 1.12 (t, 3H), 2.80 (d, 3H), 3.22 (m, 2H), 7.34-7.43 (m, 3H), 7.70 (t, 1H), 7.75 (m, 2H), 8.23 (m, 2H), 8.32 (d, 2H), 8.63 (d, 1H), 8.74 (m, 1H), 9.04 (d, 1H), 9.52 (s, 1H).

Examples 134-141

The following compounds were made by an analogous method to Example 1.

| Ex | Compound | Structure |
|---|---|---|
| 134 | methyl 3-(2-{[(ethylamino)carbonyl]amino}-1,3-thiazol-4-yl)benzoate | 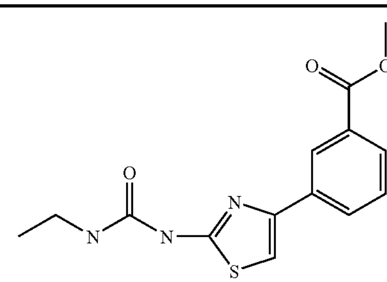 |
| 135 | ethyl 2-(2-{[(ethylamino)carbonyl]amino}pyrimidin-5-yl)-1,3-benzothiazole-7-carboxylate | 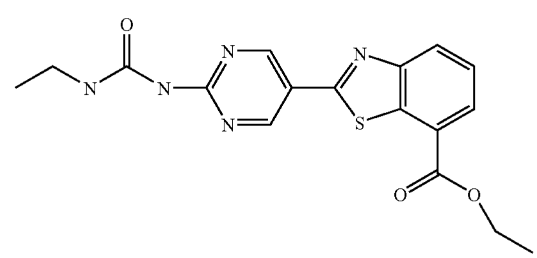 |
| 136 | ethyl 5-(6-{[(ethylamino)carbonyl]amino}pyridin-3-yl)imidazo[1,2-a]pyridine-2-carboxylate | 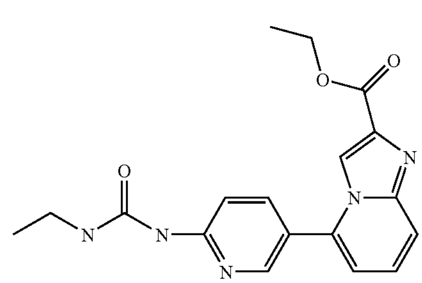 |

-continued

| Ex | Compound | Structure |
|---|---|---|
| 137 | ethyl 3-(2-{[(ethylamino)carbonyl]amino}pyridin-4-yl)benzoate | 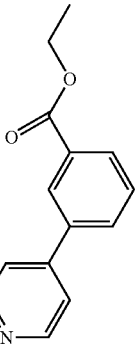 |
| 138 | ethyl 4-(2-{[(ethylamino)carbonyl]amino}pyridin-4-yl)benzoate | 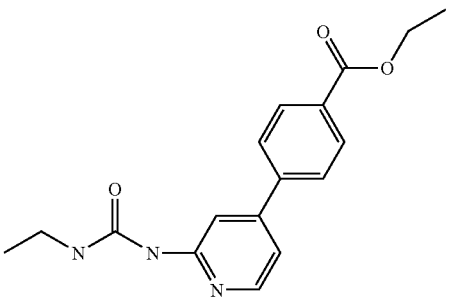 |
| 139 | ethyl 6-(6-{[(ethylamino)carbonyl]amino}pyridin-3-yl)-2-methylimidazo[1,2-a]pyridine-3-carboxylate | 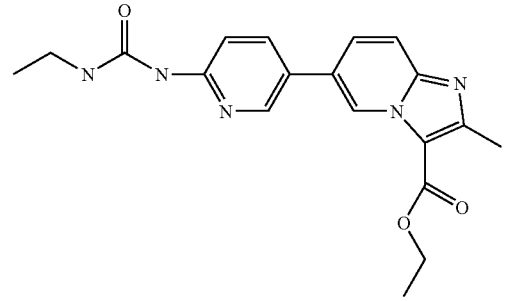 |
| 140 | ethyl 4-[(dimethylamino)carbonyl]-2-(6-{[(ethylamino)carbonyl]amino}pyridin-3-yl)-1,3-thiazole-5-carboxylate | 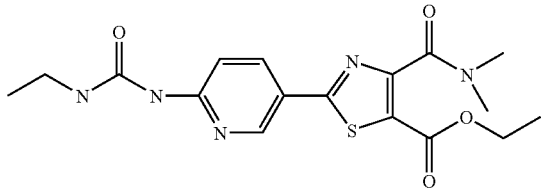 |
| 141 | ethyl 4'-(4-tert-butyl-1,3-thiazol-2-yl)-6'-{[(ethylamino)carbonyl]amino}-3,3'-bipyridine-5-carboxylate | 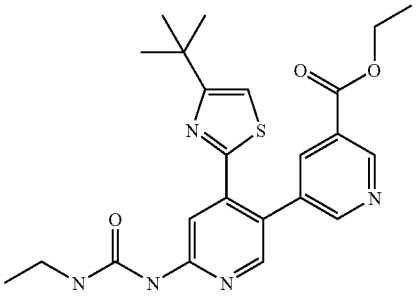 |

Examples 142-150

The following compounds were made by an analogous method to Example 17.

| Ex | Compound | Structure |
|---|---|---|
| 142 | 3-(2-{[(ethylamino)carbonyl]amino}-1,3-thiazol-4-yl)benzoic acid | 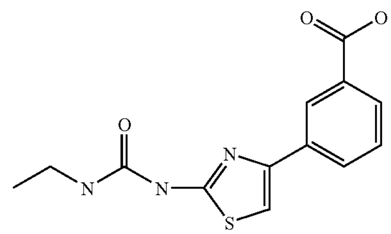 |
| 143 | 3-(2-{[(ethylamino)carbonyl]amino}pyridin-4-yl)benzoic acid | 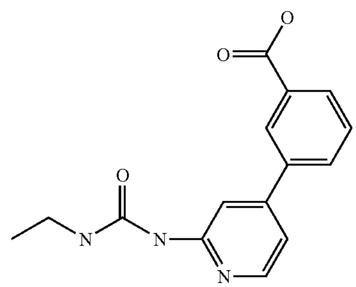 |
| 144 | 4-(2-{[(ethylamino)carbonyl]amino}pyridin-4-yl)benzoic acid | 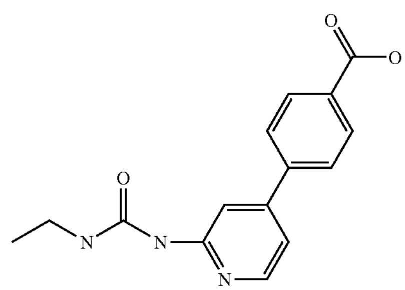 |
| 145 | 4'-(4-tert-butyl-1,3-thiazol-2-yl)-6'-{[(ethylamino)carbonyl]amino}-3,3'-bipyridine-5-carboxylic acid | 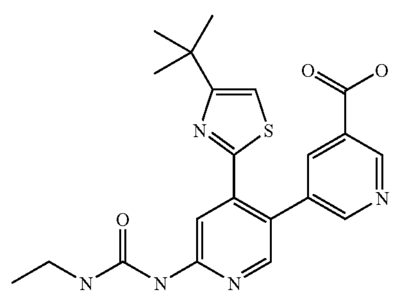 |
| 146 | [3-(6-{[(ethylamino)carbonyl]amino}pyridin-3-yl)phenyl]acetic acid | 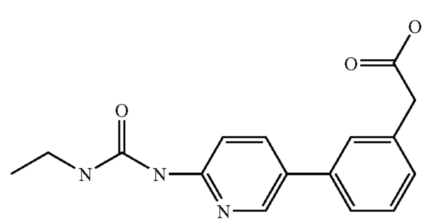 |

-continued

| Ex | Compound | Structure |
|---|---|---|
| 147 | 2-(6-{[(ethylamino)carbonyl]amino}pyridin-3-yl)-4-(1-methyl-1H-1,2,4-triazol-5-yl)-1,3-thiazole-5-carboxylic acid | 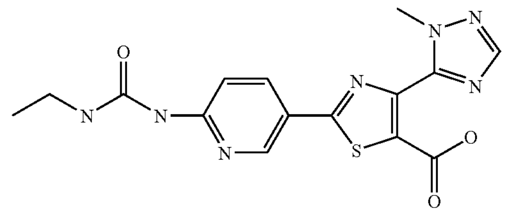 |
| 148 | 6-(6-{[(ethylamino)carbonyl]amino}pyridin-3-yl)-2-methylimidazo[1,2-a]pyridine-3-carboxylic acid | 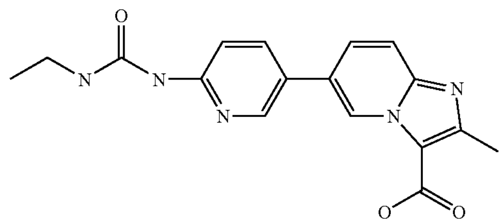 |
| 149 | 4-[(dimethylamino)carbonyl]-2-(6-{[(ethylamino)carbonyl]amino}pyridin-3-yl)-1,3-thiazole-5-carboxylic acid | 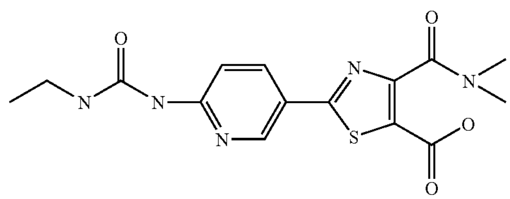 |
| 150 | 4-[(butylamino)carbonyl]-2-[6-{[(ethylamino)carbonyl]amino}-4-(4-ethyl-1,3-thiazol-2-yl)pyridin-3-yl]-1,3-thiazole-5-carboxylic acid | 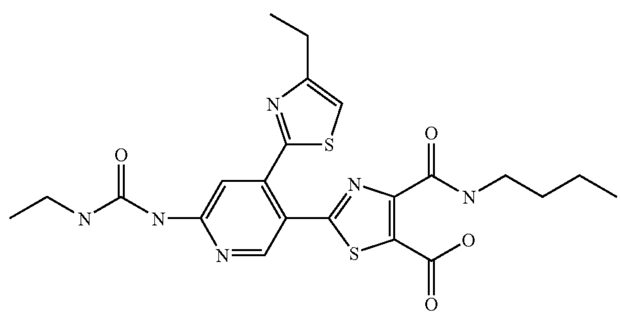 |

Example 151-165

The following compounds were made by an analogous method to Example 37.

| Ex | Compound | Structure |
|---|---|---|
| 151 | 3-(6-{[(ethylamino)carbonyl]amino}pyridin-2-yl)benzamide | 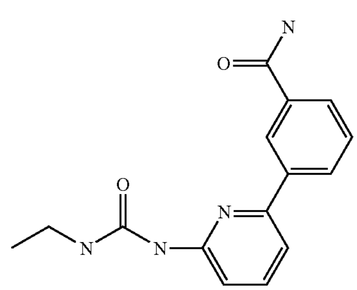 |

-continued

| Ex | Compound | Structure |
|---|---|---|
| 152 | 2-(6-{[(ethylamino)carbonyl]amino}pyridin-3-yl)-1,3-thiazole-4,5-dicarboxamide | 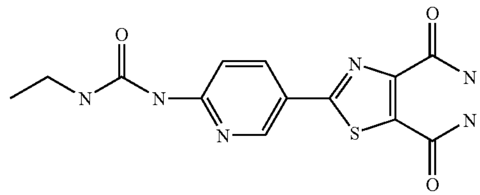 |
| 153 | 4-acetyl-2-(6-{[(ethylamino)carbonyl]amino}pyridin-3-yl)-N,N-dimethyl-1,3-thiazole-5-carboxamide | 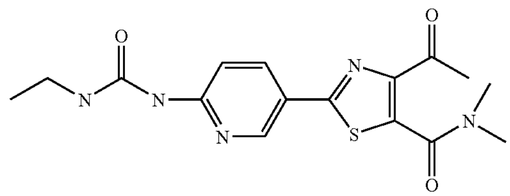 |
| 154 | 4-acetyl-2-(6-{[(ethylamino)carbonyl]amino}pyridin-3-yl)-1,3-thiazole-5-carboxamide | 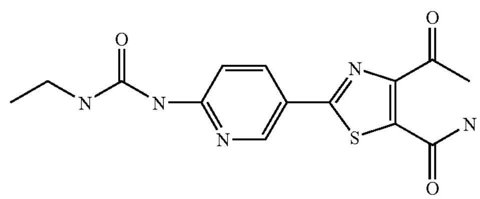 |
| 155 | 6-(6-{[(ethylamino)carbonyl]amino}pyridin-3-yl)-2-methylimidazo[1,2-a]pyridine-3-carboxamide | 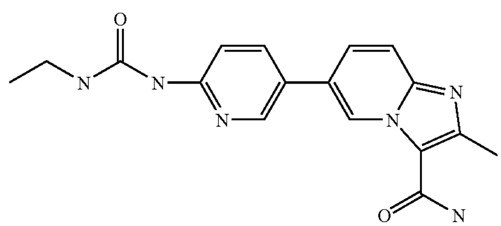 |
| 156 | 3-(6-{[(ethylamino)carbonyl]amino}pyridin-2-yl)-N,N-dimethylbenzamide | 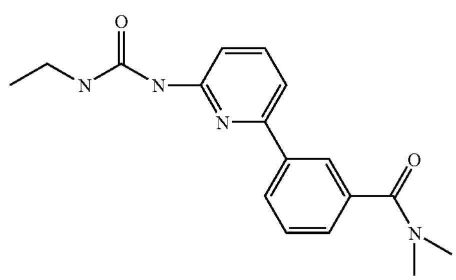 |
| 157 | 2-(6-{[(ethylamino)carbonyl]amino}pyridin-3-yl)-4-(1-methyl-1H-1,2,4-triazol-5-yl)-1,3-thiazole-5-carboxamide | 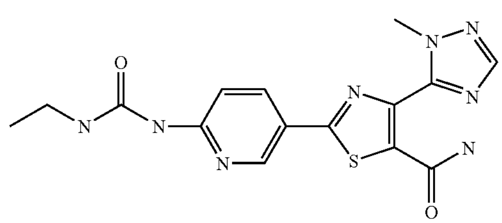 |
| 158 | $N^5$-butyl-2-(6-{[(ethylamino)carbonyl]amino}pyridin-3-yl)-$N^4$,$N^4$-dimethyl-1,3-thiazole-4,5-dicarboxamide | 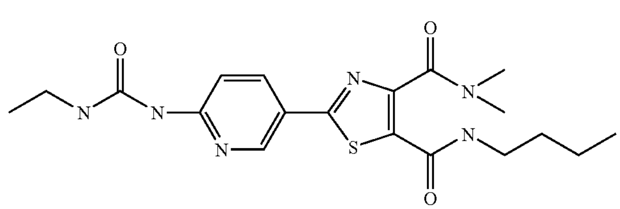 |

| Ex | Compound | Structure |
|---|---|---|
| 159 | $N^5$-(tert-butyl)-2-(6-{[(ethylamino)carbonyl]amino}pyridin-3-yl)-$N^4,N^4$-dimethyl-1,3-thiazole-4,5-dicarboxamide | 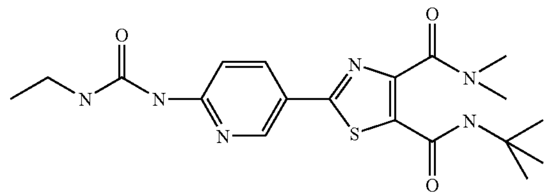 |
| 160 | 3-[6-{[(ethylamino)carbonyl]amino}-4-(4-ethyl-1,3-thiazol-2-yl)pyridin-3-yl]-N,N-dimethylbenzamide | 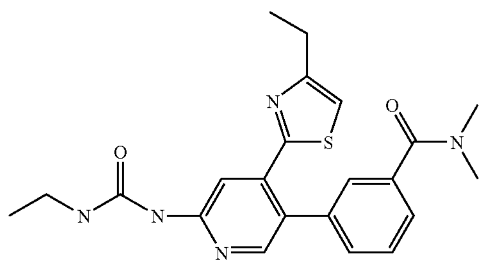 |
| 161 | 6'-{[(ethylamino)carbonyl]amino}-4'-(4-ethyl-1,3-thiazol-2-yl)-N,N-dimethyl-3,3'-bipyridine-5-carboxamide | 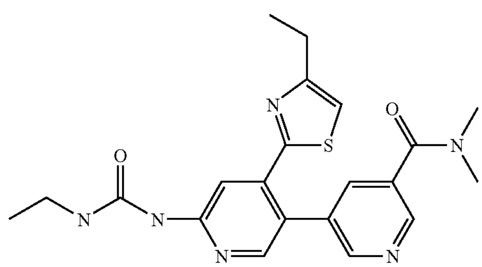 |
| 162 | $N^4$-butyl-2-[6-{[(ethylamino)carbonyl]amino}-4-(4-ethyl-1,3-thiazol-2-yl)pyridin-3-yl]-N~5~,N~5~-dimethyl-1,3-thiazole-4,5-dicarboxamide | 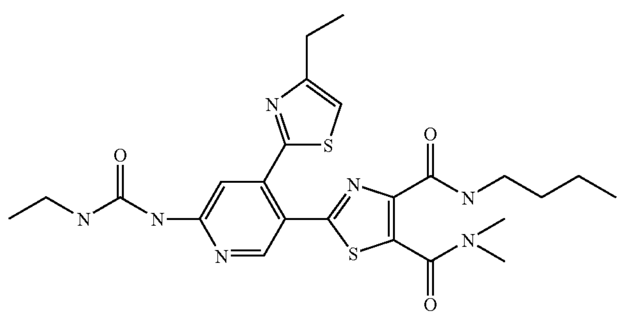 |
| 163 | N-butyl-2-(6-{[(ethylamino)carbonyl]amino}-4-phenylpyridin-3-yl)-1,3-thiazole-4-carboxamide | 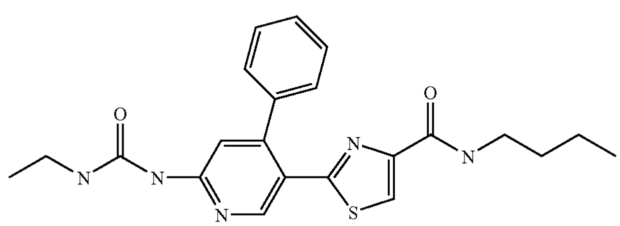 |
| 164 | 4'-(4-tert-butyl-1,3-thiazol-2-yl)-6'-{[(ethylamino)carbonyl]amino}-N-methyl-3,3'-bipyridine-5-carboxamide | 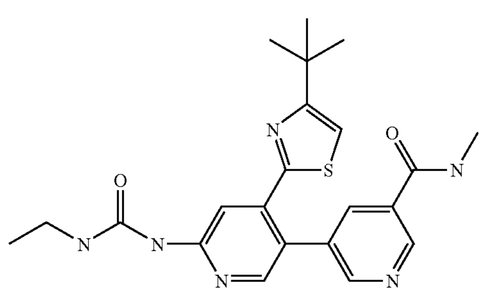 |

| Ex | Compound | Structure |
|---|---|---|
| 165 | 6'-{[(ethylamino)carbonyl]amino}-N⁴-isopropyl-N⁵,N⁵-dimethyl-2,3'-bipyridine-4,5-dicarboxamide | 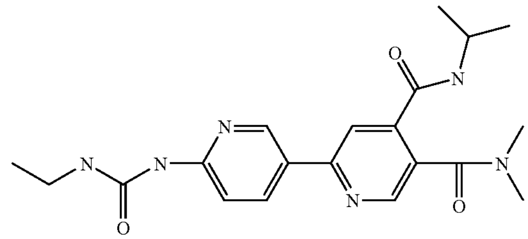 |

Preparation of Starting Materials

Intermediate 1

N-Ethyl-N'-[5-(4,4,5,5-tetramethyl-1,3,2-dioxaborolan-2-yl)pyridin-2-yl]urea

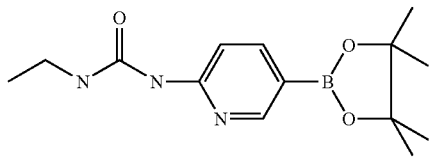

To a solution of 5-(4,4,5,5-tetramethyl-1,3,2-dioxaborolan-2-yl)pyridin-2-amine (1 g, 4.5 mmol) in chloroform (5 mL), ethyl isocyanate (0.33 mL, 4.5 mmol) was added. The resulting mixture was microwaved at 110° C. for one hour and concentrated to give 1 g of product (white solid). MS (ESP): 292 (M+H⁺) for $C_{14}H_{22}BN_3O_3$; NMR (CDCl₃): 1.22 (t, 3H), 1.32 (s, 2H), 3.41 (m, 2H), 6.82 (d, 1H), 7.90 (dd, 1H), 8.52 (s, 1H), 8.62 (s, 1H), 9.40 (s, 1H).

Intermediate 2

N-Ethyl-N'-[5-(4,4,5,5-tetramethyl-1,3,2-dioxaborolan-2-yl)pyrimidin-2-yl]urea

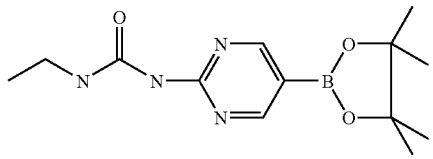

The title compound was synthesized by a method analogous to Intermediate 1 synthesis starting with 5-(4,4,5,5-tetramethyl-1,3,2-dioxaborolan-2-yl)pyrimidin-2-amine and ethyl isocyanate. NMR (CDCl₃): 1.23 (t, 3H), 1.32 (s, 12H), 3.41 (m, 2H), 7.95 (s, 1H), 8.76 (s, 2H), 9.10 (s, 1H).

Intermediate 3

N-(6-Bromopyridin-2-yl)-N'-ethylurea

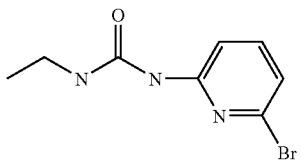

The title compound was synthesized by a method analogous to Intermediate 1 synthesis starting with 6-bromopyridin-2-amine and ethyl isocyanate. The crude residue was purified by flash chromatography (EtOAc/hexanes as eluent). MS (ESP): 245 (M+H⁺) for $C_8H_{10}BrN_3O$; NMR: 1.08 (t, 3H), 3.16 (m, 2H), 7.26 (d, 1H), 7.64 (s, 1H), 7.75 (s, 1H), 8.08 (d, 1H), 9.29 (s, 1H).

Intermediate 4

Ethyl 2-chloro-4-[(cyclopropylamino)carbonyl]-1,3-thiazole-5-carboxylate

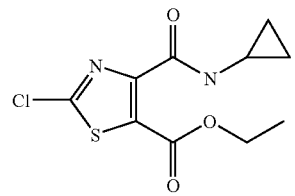

To a 0° C. solution of ethyl 2-chloro-4-(chlorocarbonyl)-1,3-thiazole-5-carboxylate (254 mg, 1 mmol. Intermediate 6) in DCM (1 mL), 2,6-lutidine (116 μL, 1 mmol) was added followed by the addition of cyclopropylamine (69.5 μL, 1 mmol). The solution was warmed to room temperature slowly and then stirred for 1 hour. The solvent was removed and the crude was partitioned between water and EtOAc. The layers separated and the organic layer was washed with 1 N HCl, sat. NaHCO₃ solution, water and brine. It was dried over magnesium sulfate and concentrated to the product (266 mg, off-white solid). MS (ESP): 275 (M+H⁺) for $C_{10}H_{11}N_2O_3S$; NMR (CDCl₃): 0.60-0.65 (m, 2H), 0.82-0.88 (m, 2H), 1.37 (t, 3H), 2.91-2.94 (m, 1H), 4.38 (q, 2H), 7.84 (s, 1H).

Intermediate 5

Ethyl 4-[(butylamino)carbonyl]-2-chloro-1,3-thiazole-5-carboxylate

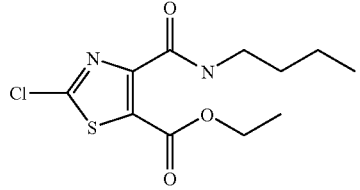

The title compound was synthesized by a method analogous to the synthesis of the Intermediate 4 starting with Intermediate 6 and n-butylamine. MS (ESP): 291 (M+H$^+$) for $C_{11}H_{15}N_2O_3S$; NMR (CDCl$_3$: 0.93 (s, 3H), 1.37 (t, 3H), 1.34-1.43 (m, 2H), 1.54-1.64 (m, 2H), 3.43 (q, 2H), 4.39 (q, 2H), 7.75 (s, 1H).

Intermediate 6

Ethyl 2-chloro-4-(chlorocarbonyl)-1,3-thiazole-5-carboxylate

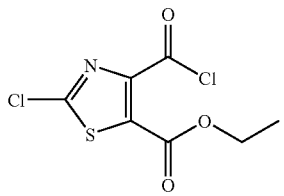

2-Chloro-5-(ethoxycarbonyl)-1,3-thiazole-4-carboxylic acid (Intermediate 7, 1 g, 4.24 mmol) was dissolved in thionyl chloride (5 mL) and refluxed for two hours. It was then concentrated to give the desired product (light brown oil, 1 g). NMR (CDCl$_3$): 1.37 (t, 3H), 4.39 (q, 2H).

Intermediate 7

2-Chloro-5-(ethoxycarbonyl)-1,3-thiazole-4-carboxylic acid

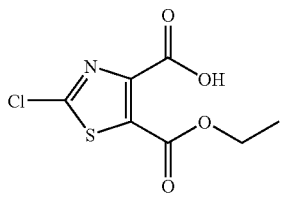

To a solution of ethyl 2-chloro-4-(hydroxymethyl)-1,3-thiazole-5-carboxylate (Intermediate 8, 2.5 g, 11 mmol) in acetone at 0° C. was slowly added a solution of chromium trioxide (2.26 g, 22 mmol) in 20% conc. Sulfuric acid in water (20 mL). After stirring at room temperature for 2 hrs, isopropanol (1 mL) was added to quench unreacted chromium trioxide. The reaction was diluted with water and the acetone was removed. Partitioning with methylene chloride (×3), drying with MgSO4 and concentrating yielded a white solid (2.3 g, 90%). MS (ES): 236 (M+H$^+$) for $C_7H_6ClNO_4S$; NMR: 1.26 (t, 3H), 4.31 (q, 2H), 13.99-14.15 (m, 1H).

Intermediate 8

Ethyl 2-chloro-4-(hydroxymethyl)-1,3-thiazole-5-carboxylate

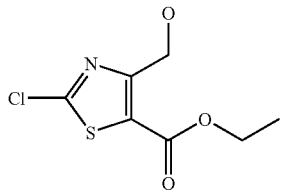

t-Butylnitrite (1.8 ml (14 mmol) was added slowly to a mixture of 2.9 g (9.2 mmol) of ethyl 2-amino-4-(hydroxymethyl)-1,3-thiazole-5-carboxylate (Intermediate 9) and 1.95 g (14 mmol) CuCl$_2$ in CH$_3$CN. After stirring at room temperature for 2 h, solvent was removed and the residue was taken up in EtOAc, which was washed 2 times with 1NHCl and once with brine. Drying (MgSO$_4$) and removal of solvent gave 2.95 g of product as an oil. NMR (CDCl$_3$): 0.1 (s, 6H), 0.9 (s, 9H), 1.35 (t, 3H), 4.3 (q, 2H), 5.0 (s, 2H).

Intermediate 9

Ethyl 2-amino-4-(hydroxymethyl)-1,3-thiazole-5-carboxylate

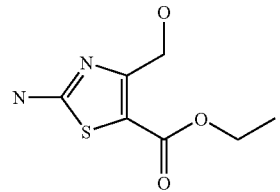

A solution of 5.0 g (37 mmol) of 3-chlorofuran-2,4(3H,5H)-dione and 3.3 g (43 mmol) of thiourea in 50 ml EtOH was heated at reflux for 4 h. Solvent was removed and the residue was dissolved in water with 1N HCl added. The aqueous solution was basified with aqueous Na$_2$CO$_3$. Thick solids that formed were filtered, rinsed with water and dried in vacuo. NMR: 1.2 (t, 3H), 4.2 (q, 2H), 4.6 (s, 2H), 4.9 (br s, 1H), 7.8 (s, 2H).

Intermediate 10

Isopropyl 2-chloro-4-[(methylamino)carbonyl]-1,3-thiazole-5-carboxylate

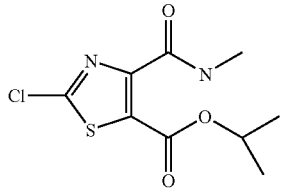

The title compound was synthesized by a method analogous to the synthesis of Intermediate 4. 2-Chloro-5-(isopropoxycarbonyl)-1,3-thiazole-4-carboxylic acid (Intermediate 12) was treated with thionylchloride to provide Isopropyl 2-chloro-4-(chlorocarbonyl)-1,3-thiazole-5-carboxylate, which was further combined with methylamine (2N in THF) to give Intermediate 10. MS (ES): 285 (M+H$^+$) for $C_9H_{11}ClN_2O_3S$; NMR: 1.25 (d, 6H), 2.75 (d, 3H), 5.1 (septet, 1H), 8.6 (m, 1H).

Intermediate 11

Methyl 4-(2-amino-1,3-thiazol-4-yl)benzoate

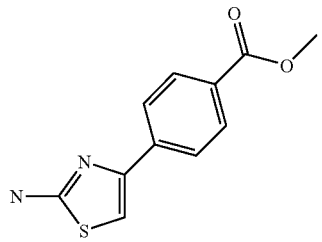

Methyl 4-(bromoacetyl)benzoate (300 mg, 1.17 mmol) and thiourea 110 mg, 1.40 mmol) were taken in MeOH (5 ml) and refluxed for 2 hours. The precipitated product was collected by filtration, washed with MeOH and dried (260 g). MS (ESP): 235 (M+H$^+$) for $C_{11}H_{10}N_2O_2S$; NMR: 3.87 (s, 3H), 7.38 (s, 1H), 7.90 (d, 2H), 8.01 (d, 2H).

Intermediate 12

2-Chloro-5-(isopropoxycarbonyl)-1,3-thiazole-4-carboxylic acid

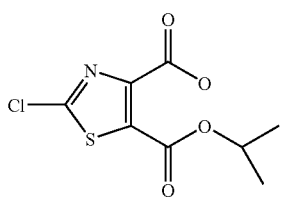

A solution of 3 mL $H_2SO_4$ and 12 mL water were cooled in an ice water bath, and 2.3 g (23 mmol) $CrO_3$ was added portionwise. The solution was added dropwise to a cooled (ice water bath) solution of 2.74 g (11.6 mmol) of isopropyl 2-chloro-4-(hydroxymethyl)-1,3-thiazole-5-carboxylate (Intermediate 13) in acetone (50 mL) The resulting mixture was stirred 4 hours with warming to room temperature. Isopropanol (2 mL) was added and stirring was continued for 15 min. The solution was diluted with water, saturated with NaCl and extracted 3 times with EtOAc. The EtOAc was washed with brine, dried (MgSO$_4$) and concentrated to give 2.86 g of an oil. NMR: 1.3 (d, 6H), 5.1 (m, 1H), 14.1 (s, 1H).

Intermediate 13

Isopropyl 2-chloro-4-(hydroxymethyl)-1,3-thiazole-5-carboxylate

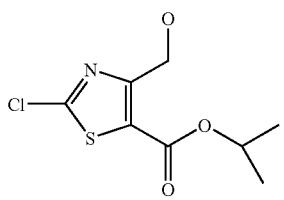

t-Butylnitrite (3.1 mL, 23.5 mmol) was added slowly to a mixture of 3.4 g (16 mmol) of isopropyl 2-amino-4-(hydroxymethyl)-1,3-thiazole-5-carboxylate (Intermediate 14) and 3.2 g (24 mmol) CuCl$_2$ in 50 mL CH$_3$CN at room temperature. After stirring for 2 hours, the reaction was quenched with and aqueous NaHSO$_3$ and diluted with 1N HCl and extracted with EtOAc. The extract was washed with 1N HCl, brine and dried over magnesium sulfate. Then the solvent was removed to give an oil that was purified by flash chromatography (100% DCM with gradient elution to 20% EtOAc in DCM) to give the desired product (2.75 g, oil). NMR:__1.3 (d, 6H), 4.75 (d, 2H), 5.1 (septet, 1H), 5.4 (t, 1H).

Intermediate 14

Isopropyl 2-amino-4-(hydroxymethyl)-1,3-thiazole-5-carboxylate

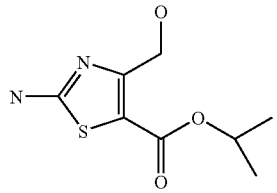

A solution of 5 g (37 mmol) of 3-chlorofuran-2,4(3H,5H)-dione and 3.7 g (49 mmol) thiourea in 30 mL isopropanol was heated at refluxed overnight. Solvent was removed and the residue was dissolved in water. The solution was treated with aqueous Na$_2$CO$_3$ precipitating solids. The solids were filtered, washed with water and dried in vacuum. NMR: 1.2 (d, 6H), 4.55 (d, 2H), 4.9 (t, 1H), 5.0 (m, 1H), 7.7 (s, 2H).

Intermediate 15

Methyl 4-acetyl-2-chloro-1,3-thiazole-5-carboxylate

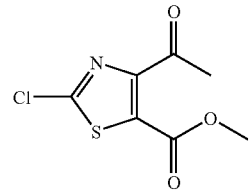

t-Butylnitrite (1.12 mL, 9.45 mmol) was added slowly to a mixture of methyl 4-acetyl-2-amino-1,3-thiazole-5-carboxylate (1.65 g, 6.69 mmol) (Intermediate 16) and CuCl$_2$ (1.28 g, 9.45 mmol) in CH$_3$CN. After stirring at room temperature for 2 h, solvent was removed and the residue was taken up in EtOAc, which was washed 2 times with 1NHCl and once with brine. Drying (MgSO$_4$) and removal of solvent gave 2.95 g of product as an oil (1.21 g). NMR (CDCl$_3$): 2.6 (s, 3H), 3.9 (s, 3H).

Intermediate 16

Methyl 4-acetyl-2-amino-1,3-thiazole-5-carboxylate

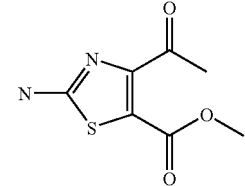

A solution of 4.37 g (19 mmol) methyl 2-chloro-4,4-dimethoxy-3-oxopentanoate (Intermediate 17) and 1.8 g (24 mmol) thiourea in 50 ml EtOH was heated at reflux for 3 h.

Solvent was removed and the residue was dissolved in 1:1 acetone-5N HCl and the solution was heated at reflux for 4 h. Acetone was removed and the aqueous residue was neutralized with 50% NaOH and then basified with aqueous $Na_2CO_3$. Precipitated solids were filtered, washed with water and dried in vacuum. NMR: 2.4 (s, 3H), 3.7 (s, 3H), 8.0 (s, 2H).

Intermediate 17

Methyl 2-chloro-4,4-dimethoxy-3-oxopentanoate

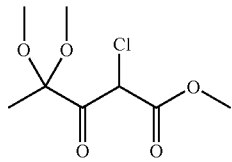

$SO_2Cl_2$ (2.2 ml, 27 mmol) was added slowly to a solution of 5.0 g (26 mmol) of methyl 4,4-dimethoxy-3-oxopentanoate in 30 ml DCM cooled in an ice water bath. The solution was warmed to room temperature and stirred for 1 h. Solvent was removed and the residue was taken up in EtOAc, which was washed with water and brine. Drying ($MgSO_4$) and removal of solvent gave 6.1 g of an oil. NMR ($CDCl_3$): 1.5 (s, 3H), 3.25 (2s, 6H), 4.8 (s, 3H), 5.3 (s, 1H).

Intermediate 18

2-(6-{[(Ethylamino)carbonyl]amino}pyridin-3-yl)-N-(1-methyl-1-phenylethyl)-1,3-thiazole-5-carboxamide

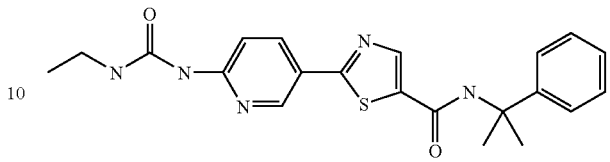

HATU (0.078 mg, 0.225 mmol) was added to a solution of 2-(6-{[(ethylamino)carbonyl]amino}pyridin-3-yl)-1,3-thiazole-5-carboxylic acid (Example 17, 60 mg, 0.205 mmol), $Et_3N$ (84 μL, 0.41 mmol) and cumylamine (28 mg, 0.205 mmol) in 3 mL DMF. After stirring at room temperature for two hours, the mixture was diluted with water and extracted with EtOAc. The product precipitated during the workup and it was collected by filtration, washed with water and EtOAc and dried (20 mg). MS (ESP): 410 (M+H$^+$) for $C_{21}H_{23}N_5O_2S$.

Intermediates 19-21

The following compounds were made by an analogous method to Intermediate 18.

| Int | Compound | Data | SM |
|---|---|---|---|
| 19 | $N^4$-Cyclopropyl-2-(6-{[(ethylamino)carbonyl]amino}pyridin-3-yl)-$N^5$-(1-methyl-1-phenylethyl)-1,3-thiazole-4,5-dicarboxamide | MS (ESP): 493 (M + H$^+$) for $C_{25}H_{28}N_6O_3S$ | Example 25 |
| 20 | $N^4$-Butyl-2-(6-{[(ethylamino)carbonyl]amino}pyridin-3-yl)-$N^5$-(1-methyl-1-phenylethyl)-1,3-thiazole-4,5-dicarboxamide | MS (ESP): 509 (M + H$^+$) for $C_{26}H_{32}N_6O_3S$ | Example 26 |
| 21 | 2-(6-{[(Ethylamino)carbonyl]amino}pyridin-3-yl)-N-(1-methyl-1-phenylethyl)-1,3-benzothiazole-7-carboxamide | MS (ES): 460 (M + H$^+$) for $C_{25}H_{25}N_5O_2S$ | Example 20 |

Intermediate 22

Ethyl 1-butyl-6-iodo-4-oxo-1,4-dihydroquinoline-3-carboxylate

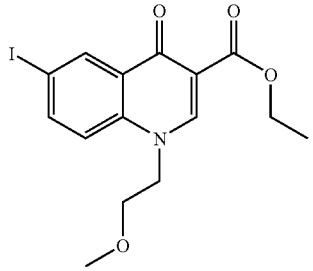

A suspension of (Z)-ethyl 3-(dimethylamino)-2-(2-fluoro-5-iodobenzoyl)acrylate (WO2006/010733, 415 mg, 1.06 mmol) in ethanol (6 mL) at room temperature was treated with N-butylamine (0.115 mL, 1.17 mmol). The reaction mixture was stirred until a yellow solution resulted, then concentrated under reduced pressure after 1 h. Potassium carbonate (220 mg, 1.59 mmol) and DMF (4 mL) were added to the concentrate, and the reaction mixture was heated to 70° C. for 3 h, cooled to room temperature, and allowed to stand overnight. The next day the reaction mixture was poured into water, and the solid that formed was collected by filtration, washed with water, dissolved in methylene chloride and concentrated under reduced pressure to give title compound which was placed on high vac to remove residual solvent. MS (ESP): 400 (M+H$^+$) for $C_{16}H_{18}INO_3$; NMR: 0.90 (t, J=7 Hz, 3H), 1.28 (t, J=6 Hz, 3H), 1.33 (m, 2H), 1.71 (m, 2H), 4.22 (q, J=7 Hz, 2H), 4.35 (m, 2H), 7.64 (m, 1H), 8.05 (m, 1H), 8.50 (m, 1H), 8.70 (s, 1H).

Intermediate 23

Ethyl 2-(2-fluoro-5-iodobenzoyl)-3-(2-morpholinoethylamino)acrylate

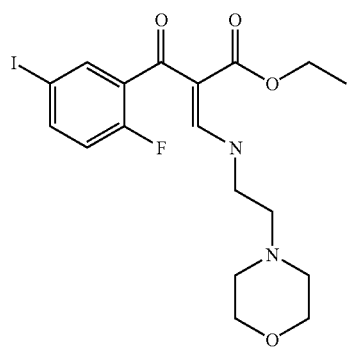

A suspension of ethyl 3-(dimethylamino)-2-(2-fluoro-5-iodobenzoyl)acrylate (WO2006/010733, 294 mg, 0.75 mmol) in ethanol (2.500 mL) and diethyl ether (5 mL) was cooled 0° C. and 4-(2-aminoethyl)morpholine (103 mg, 0.79 mmol) was added dropwise. The reaction mixture was stirred for 3 h, then concentrated under reduced pressure to give the desired product (358 mg). MS (ESP): 477 (M+H$^+$) for $C_{18}H_{22}FIN_2O_4$.

Intermediate 24

Ethyl 6-iodo-1-(2-morpholinoethyl)-4-oxo-1,4-dihydroquinoline-3-carboxylate

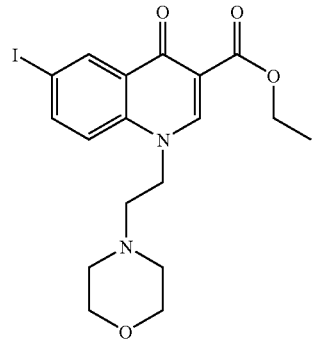

A solution of ethyl 2-(2-fluoro-5-iodobenzoyl)-3-(2-morpholinoethylamino)acrylate (Intermediate 23, 358 mg, 0.75 mmol) and potassium carbonate (208 mg, 1.50 mmol) in DMF (7 mL) was heated to 100° C. for 4 h. The reaction mixture was cooled to room temperature, filtered, and concentrated under reduced pressure. The solid that formed was placed under high vacuum overnight (328 mg) to yield the desired product. MS (ESP): 457 (M+H$^+$) for $C_{18}H_{21}IN_2O_4$; NMR: 1.28 (t, J=7 Hz, 3H), 2.43 (m, 4H), 2.61 (m, 2H), 3.50 (m, 4H), 4.22 (q, J=7 Hz, 2H), 4.46 (m, 2H), 7.67 (d, J=9 Hz, 1H), 8.05 (m, 1H), 8.50 (s, 1H), 8.63 (s, 1H).

Intermediate 25

Ethyl 1-(2,2-difluoroethyl)-6-iodo-4-oxo-1,4-dihydroquinoline-3-carboxylate

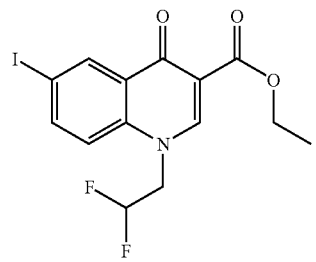

A suspension of ethyl 3-(dimethylamino)-2-(2-fluoro-5-iodobenzoyl)acrylate (335 mg, 0.86 mmol) and 2,2-difluoroethylamine (76 mg, 0.94 mmol) in ethanol (3 mL) was stirred at room temperature for 30 minutes. The reaction mixture was concentrated under reduced pressure and dissolved in DMF (3 mL). Potassium carbonate (178 mg, 1.28 mmol) was added to the reaction mixture and the reaction was heated to 70° C. for 3 h, then cooled to room temperature and poured into water. The title compound formed a precipitate which was collected by filtration and placed upon lyophilizer overnight to remove residual water. MS (ESP): 408 (M+H$^+$) for $C_{14}H_{12}F_2INO_3$; NMR: 1.29 (t, J=7 Hz, 3H), 4.25 (q, J=7 Hz, 2H), 4.96 (m, 2H), 6.50 (t, J=20 Hz, 1H), 7.73 (m, 1H), 8.08 (m, 1H), 8.50 (m, 1H), 8.70 (s, 1H).

Intermediate 26

Ethyl 2-Chloro-4-dimethylcarbamoyl-thiazole-5-carboxylate

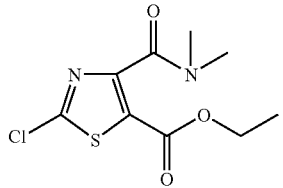

To a stirred solution of 2-chloro-5 (ethoxy carbonyl)-1,3-thiazole-4-carboxylic acid (Intermediate 7, 2 g, 8.01 mmol) in dry dichloromethane (20 mL) was added oxalyl chloride (1.37 mL, 16.02 mmol) and 2 drops of dry dimethylformamide. The reaction mixture was heated to 45° C. for 90 minutes. After the completion of the reaction, the reaction mixture was evaporated to dryness under reduced pressure. The residue was dissolved in dry dichloromethane (20 mL) and was cooled to 0° C., then 2,6-lutidine (0.97 mL, 8.4 mmol) was added followed by addition of N,N-dimethylamine (2 M solution in tetra hydro furan, 4.19 mL, 8.4 mmol). After completion of the reaction, the reaction mixture was concentrated to dryness and the residue was extracted with ethyl acetate (2×50 mL). The organic layer was washed with 1 N hydrochloric acid, water and brine (1×50 mL), and concentrated after drying over anhydrous sodium sulfate to afford 1.6 g (72.7%) of the title compound as a thick syrup.

MS (APCI): 263 (M+H$^+$) for $C_9H_{11}ClN_2O_3S$; NMR: δ 1.34 (t, 3H), δ 2.89 (s, 3H), δ 3.13 (s, 3H), δ 4.33 (q, 2H)

Intermediate 27

Ethyl 2-chloro-4-propylcarbamoyl-thiazole-5-carboxylate

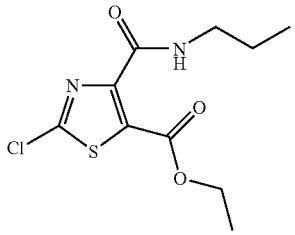

To a stirred solution of 2-chloro-5 (ethoxycarbonyl)-1,3-thiazole-4-carboxylic acid (Intermedate 7, 1.0 g, 4.23 mM) in dry dichloromethane (20 mL) was added oxalyl chloride (0.729 mL, 8.4 mM) and 2 drops of dry dimethylformamide. The reaction mixture was refluxed to 45° C. for 1½ h. After the completion of the reaction (which was monitored by converting a small sample in to methyl ester via contacting it with methanol), the reaction mixture was evaporated to dryness under reduced pressure. The residue was dissolved in dry dichloromethane (20 mL) and cooled to 0° C., then 2,6-lutidine (0.485 mL, 4.23 mM) was added followed by addition of propyl amine (0.348 mL, 4.23 mM). After completion of the reaction, the reaction mixture was concentrated to dryness and the residue was extracted with ethyl acetate (2×50 mL). The organic layer was washed with 1 N hydrochloric acid (1×50 mL), then dried over anhydrous sodium sulfate and concentrated under vacuum to afford 1.10 g (94%) of the title compound as a thick syrup. MS (APCI): 271 (M+H$^+$) for $C_{10}H_{13}ClN_2O_3S$; NMR: 0.92 (t, 3H), δ 1.38 (t, 3H), δ 1.63 (m, 2H), δ 3.40 (q, 2H), 4.40 (q, 2H), 7.9 (br s, 1H).

Intermediate 28

Ethyl 2-chloro-4-isopropylcarbamoyl-thiazole-5-carboxylate

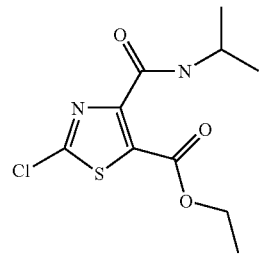

To a stirred solution of 2-chloro-5 (ethoxycarbonyl)-1,3-thiazole-4-carboxylic acid (Intermediate 7, 1.0 g, 4.2 mmol) in dry dichloromethane (20 mL) was added oxalyl chloride (0.73 mL, 8.4 mmol) and 2 drops of dry dimethylformamide. The reaction mixture was refluxed to 45° C. for 1½ h. The reaction mixture was cooled to room temperature, and then evaporated to dryness under reduced pressure. The residue was dissolved in dry dichloromethane (20 mL) and cooled to 0° C., then 2,6-lutidine (0.493 mL, 4.237 mmol) was added followed by addition of isopropyl amine (0.360 mL, 4.237 mmol). After completion of the reaction, the reaction mixture was concentrated to dryness and the residue was extracted with ethyl acetate (2×50 mL). The organic layer was washed with 1 N hydrochloric acid (1×50 mL), then dried over anhydrous sodium sulfate and concentrated under vacuum to afford 1.13 g (96%) of the title compound as a thick syrup. NMR: 1.26 (d, 6H), 1.38 (t, 3H), 4.24 (m, 1H), 4.40 (q, 2H), 7.51 (br s, 1H).

Intermediate 29

N-ethyl-N'-(5-fluoro-3,4'-bipyridin-2'-yl)urea

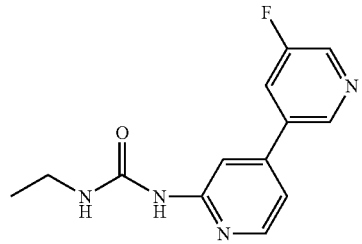

N-(4-bromopyridin-2-yl)-N'-ethylurea (Intermediate 33, 0.50 g, 2.05 mmol), 2-fluoro-5-(4,4,5,5-tetramethyl-1,3,2-dioxaborolan-2-yl)pyridine (0.318 g, 2.25 mmol), tetrakis triphenyl phosphine palladium (0.118 g, 0.10 mmol), and cesium carbonate (0.667 g, 2.05 mmol) were taken in a microwave vial and degassed with nitrogen. Dioxane:water (4:1, 5 mL) was added to the vial and the reaction mixture was heated to 100° C. for 30 minutes via microwave. The reaction mixture was partitioned between water and ethyl acetate and layers separated. The organic layer was washed with saturated sodium bicarbonate solution, water, brine and dried over magnesium sulfate. The solvent was removed and the residue was washed with acetonitrile to give the title compound as a white solid (386 mg). MS (ESP): 261 (M+H$^+$) for $C_{13}H_{13}FN_4O$; NMR: 1.09 (t, 3H), 3.19 (q, 2H), 7.33 (dd, 1H), 7.74 (d, 1H), 7.94 (t, 1H), 8.02-8.11 (m, 1H), 8.29 (d, 1H), 8.69 (d, 1H), 8.76 (t, 1H), 9.26 (s, 1H).

Intermediate 30

N-(5'-bromo-5-fluoro-3,4'-bipyridin-2'-yl)-N'-ethylurea

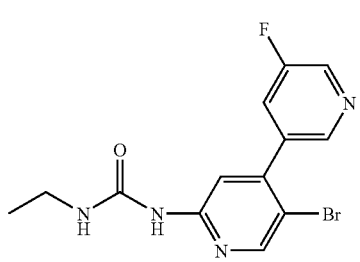

To a solution of N-ethyl-N'-(5-fluoro-3,4'-bipyridin-2'-yl)urea (Intermediate 29, 386 mg, 1.48 mmol) in DMF (7 mL), N-bromosuccinamide (396 mg, 2.22 mmol) was added. The resulting solution was heated to 80° C. and stirred at that temperature for 8 hours. The reaction mixture was partitioned between water and ethyl acetate. The layers were separated and the organic layer was washed with 5% sodium thiosulfate solution, water and brine. The organic layer was dried over sodium sulfate and concentrated under reduced pressure. The resulting solid was washed with acetonitrile and dried to give the title compound as an off-white solid (340 mg). MS (ESP): 340 (M+H$^+$) for $C_{13}H_{12}BrFN_4O$; NMR: 1.06 (t, 3H), 3.14 (q, 2H), 7.35 (t, 1H), 7.69 (s, 1H), 7.91-7.97 (m, 1H), 8.48 (s, 1H), 8.51 (t, 1H), 8.71 (d, 1H), 9.37 (s, 1H).

Intermediate 31

N-(5'-Bromo-6-fluoro-3,4'-bipyridin-2'-yl)-N'-ethylurea

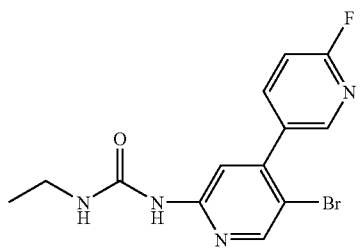

To a solution of N-ethyl-N'-(6-fluoro-3,4'-bipyridin-2'-yl)urea (Intermediate 32, 360 mg, 1.38 mmol) in DMF (7 mL), N-bromosuccinamide (246 mg, 1.38 mmol) was added. The resulting solution was heated to 80° C. and stirred at that temperature for 2 hours. Then the reaction was partitioned between water and ethyl acetate. The layers separated, and the organic layer was washed with 5% sodium thiosulfate solution, water and brine, then dried over magnesium sulfate and concentrated. The solid obtained was washed with acetonitrile and dried to give the title compound as an off-white solid (390 mg). MS (ESP): 340 (M+1) for $C_{13}H_{12}FN_4O$; NMR: 1.07 (t, 3H); 3.12-3.18 (m, 2H); 7.36-7.40 (m, 2H); 7.68 (s, 1H); 8.15 (t, 1H); 8.34 (d, 1H); 8.47 (s, 1H); 9.36 (s, 1H).

Intermediate 32

N-Ethyl-N'-(6-fluoro-3,4'-bipyridin-2'-yl)urea

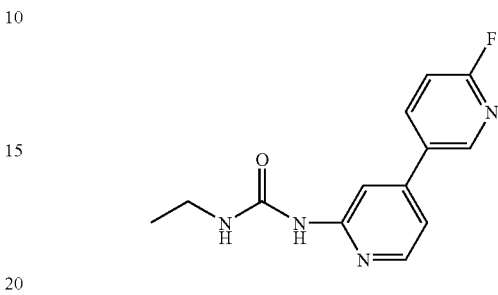

N-(4-bromopyridin-2-yl)-N'-ethylurea (Intermediate 33, 0.40 g, 1.64 mmol), 2-fluoro-5-(4,4,5,5-tetramethyl-1,3,2-dioxaborolan-2-yl)pyridine (1.057 g, 4.92 mmol), tetrakis triphenyl phosphine palladium (0.189 g, 0.16 mmol), and cesium carbonate (1.16 g, 4.92 mmol) were taken in a microwave vial and degassed with nitrogen. A dioxane:water (4:1, 10 mL) solution was added to the vial and the mixture was microwaved at 110° C. for half an hour. The palladium was filtered off, and the reaction was partitioned between water and ethyl acetate. The layers were separated, and the organic layer was washed with saturated sodium bicarbonate solution, water and brine, then dried over magnesium sulfate, and concentrated. The residue obtained was washed with acetonitrile to give the title compound as a white solid (360 mg).

MS (ESP): 261 (M+1) for $C_{13}H_{13}N_4O$

Intermediate 33

N-(4-Bromopyridin-2-yl)-N'-ethylurea

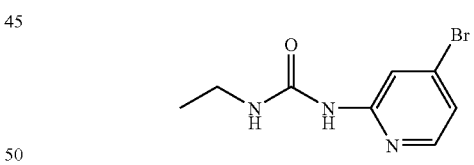

To a mixture of 4-bromopyridin-2-amine (2 g, 11.56 mmol) in chloroform (10 mL), isocyanatoethane (0.913 mL, 11.56 mmol) was added, and the resulting reaction mixture was heated at 110° C. for 2 h. The reaction mixture was concentrated under reduced pressure and triturated with acetonitrile, then collected by filtered to give the title compound as a white solid (2.15 g).

MS (ESP): 243 (M+1) for $C_8H_{10}BrN_3O$ $^1$H-NMR (DMSO-d$_6$) δ: 1.08 (t, 3H); 3.12-3.18 (m, 2H); 7.16 (dd, 1H); 7.65 (br s, 1H); 7.74 (s, 1H); 8.07 (d, 1H); 9.29 (s, 1H)

Intermediates 34-36

Intermediates 34-36 were synthesized as described for Intermediate 31 from the indicated starting materials.

| Int | Compound | Data | SM |
|---|---|---|---|
| 34 | N-(5'-Bromo-3,4'-bipyridin-2'-yl)-N'-ethylurea | MS (ESP): 322 (M + 1) for $C_{13}H_{13}BrN_4O$ | Intermediate 37 |
| 35 | N-(5-Bromo-4-phenylpyridin-2-yl)-N'-ethylurea | MS (ESP): 321 (M + 1) for $C_{14}H_{14}BrN_3O$; NMR ($CDCl_3$): 1.21 (t, 3H); 3.33-3.42 (m, 2H); 6.90 (s, 1H); 7.25 (s, 1H); 7.42-7.46 (m, 5H); 8.34 (s, 1H); 8.84 (s, 1H) | Intermediate 38 |
| 36 | N-{5-Bromo-4-[4-(trifluoromethyl)-1,3-thiazol-2-yl]pyridin-2-yl}-N'-isopropylurea | MS (ESP): 410 (M + 1) for $C_{13}H_{12}BrF_3N_4OS$ | Intermediate 40 and TFAA and TFA |

Intermediates 37-38

Intermediates 37-38 were synthesized as described for Intermediate 32 using the starting materials as indicated.

| Int | Compound | Data | SM |
|---|---|---|---|
| 37 | N-3,4'-Bipyridin-2'-yl-N'-ethylurea | MS (ESP): 243 (M + 1) for $C_{13}H_{14}N_4O$ | Intermediate 34 and 3-(4,4,5,5-tetramethyl-1,3,2-dioxaborolan-2-yl)pyridine |
| 38 | N-Ethyl-N'-(4-phenylpyridin-2-yl)urea | MS (ESP): 242 (M + 1) for $C_{14}H_{15}N_3O$ | Intermediate 34 and phenylboronic acid |

Intermediate 39

N-{5-Bromo-4-[4-(trifluoromethyl)-1,3-thiazol-2-yl]pyridin-2-yl}-N'-ethylurea

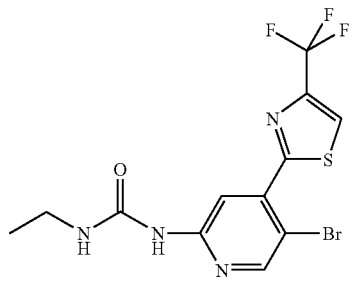

To a mixture of 1-(5-bromo-4-(4-hydroxy-4-(trifluoromethyl)-4,5-dihydrothiazol-2-yl)pyridin-2-yl)-3-ethylurea (Intermediate 41, 2.2 g, 5.32 mmol) in DCM (30 mL), TFAA (1.128 mL, 7.99 mmol) followed by TEA (1.113 mL, 7.99 mmol) were added. The reaction mixture was allowed to stir overnight at room temperature, then another 150 uL of TEA and TFAA were added and the reaction mixture was stirred for additional 3 h. The reaction was concentrated under reduced pressure, and the residue was partitioned between water and ethyl acetate. The layers were separated, and the organic layer was washed with sodium bicarbonate solution, water and brine, then dried over magnesium sulfate and concentrated under reduced pressure. The light yellow solid obtained was purified by normal phase (1% MeOH in dichloromethane to 3% MeOH in dichloromethane) to give 520 mg of the product. MS (ESP): 396 (M+1) for $C_{12}H_{10}BrN_3O$; NMR: 1.07 (t, 3H); 3.11-3.17 (m, 2H); 7.24 (t, 1H); 8.35 (s, 1H); 8.50 (s, 1H); 8.77 (s, 1H); 9.34 (s, 1H)

Intermediate 40

1-(5-Bromo-4-(4-hydroxy-4-(trifluoromethyl)-4,5-dihydrothiazol-2-yl)pyridin-2-yl)-3-isopropylurea

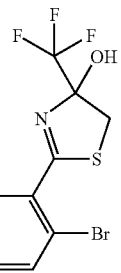

Intermediate 40 was synthesized by a method analogous to Intermediate 39 synthesis starting with Intermediate 45 and treating it with 3-bromo-1,1,1-trifluoropropan-2-one in acetonitrile.

MS (ESP): 410 (M+1) for $C_{13}H_{12}BrF_3N_4OS$

Intermediate 41

1-(5-Bromo-4-(4-hydroxy-4-(trifluoromethyl)-4,5-dihydrothiazol-2-yl)pyridin-2-yl)-3-ethylurea

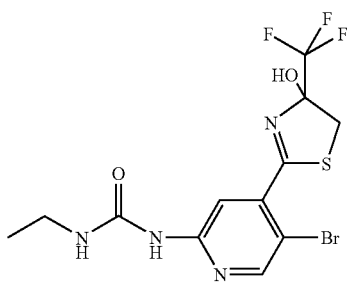

3-Bromo-1,1,1-trifluoropropan-2-one (2.260 mL, 21.77 mmol) was added to a mixture of 5-bromo-2-(3-ethylureido)pyridine-4-carbothioamide (Intermediate 42, 1.1 g, 3.63 mmol) in acetonitrile (25 mL), and the reaction mixture was heated at 80° C. for 4 h. After a clear solution resulted within an hour, and the solution was concentrated under reduced pressure and the resulting residue was partitioned between water and ethyl acetate. The organic layer was washed with water and brine, dried over magnesium sulfate, then concentrated under reduced pressure to give light yellow solid, which was purified by normal phase column chromatography (silica, 2% MeOH in dichloromethane to 5% MeOH in dichloromethane) to give the title compound as a white solid (470 mg). MS (ESP): 414 (M+1) for $C_{12}H_{12}BrF_3N_4O_2S$; NMR: 1.06 (t, 3H); 3.12-3.18 (m, 2H); 3.60 (dd, 1H); 3.90 (dd, 1H); 7.13 (brs, 1H); 7.98 (s, 1H); 8.47 (s, 1H); 9.41 (s, 1H).

Intermediate 42

5-Bromo-2-(3-ethylureido)pyridine-4-carbothioamide

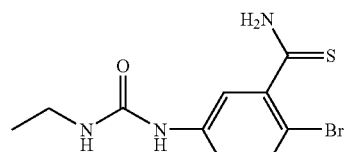

To a mixture of 5-bromo-2-(3-ethylureido)isonicotinamide (Intermediate 43, 1.25 g, 4.35 mmol) in THF (20 mL), was added Lawessons reagent (1.761 g, 4.35 mmol). The reaction mixture was then heated to 70° C. overnight. The solid that formed was collected by filtration and washed with THF to provide 1 g of desired product. MS (ESP): 304 (M+1) for $C_{19}H_{11}BrN_4OS$ Intermediate 43

5-Bromo-2-(3-ethylureido)isonicotinamide

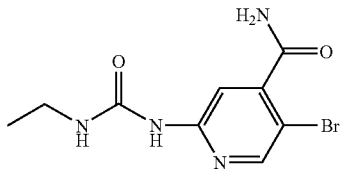

Isocyanatoethane (1.122 mL, 14.28 mmol) was added to a mixture of methyl 2-amino-5-bromoisonicotinate (3 g, 12.98 mmol) and chloroform (12 mL) in a microwave vial, and the resulting mixture was heated at 110° C. for 3 h. The reaction mixture was concentrated under reduced pressure, and 50 mL of 7N ammonia in MeOH was added. The resulting mixture was stirred at room temperature overnight and concentrated under reduced pressure. The residue obtained was washed with acetonitrile to give the title compound as a white solid (3.5 g). MS (ESP): 287 (M+1) for $C_{19}H_{11}BrN_4O_2$ Intermediate 44

N-[5-Bromo-4-(4-ethyl-1,3-thiazol-2-yl)pyridin-2-yl]-N'-ethylurea

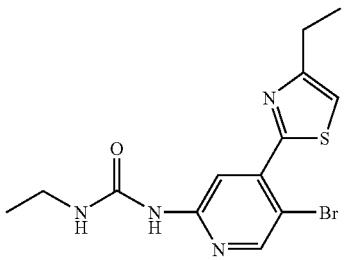

To a mixture of 5-bromo-2-(3-ethylureido)pyridine-4-carbothioamide (Intermediate 42, 1 g, 3.30 mmol) in ethanol (25 mL), 1-bromobutan-2-one (0.337 mL, 3.30 mmol) was added, and the reaction mixture was heated to 80° for 4 h, then cooled to room temperature, concentrated under reduced pressure, and the resulting solid was washed with acetonitrile to give the title compound as an off-white solid (431 mg). MS (ESP): 356 (M+1) for $C_{13}H_{15}BrN_4OS$; NMR: 1.09 (t, 3H); 1.29 (t, 3H); 2.84 (q, 2H); 3.15-3.20 (m, 2H); 7.34 (br s, 1H); 7.66 (s, 1H); 8.38 (s, 1H); 8.50 (s, 1H); 9.36 (s, 1H).

Intermediate 45

5-Bromo-2-(3-isopropylureido)pyridine-4-carbothioamide

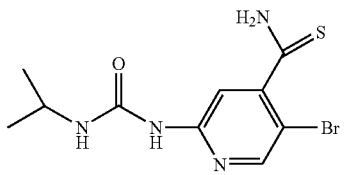

The title compound was synthesized by a method analogous to the synthesis of Intermediate 42 starting with Intermediate 46 and Lawesson's reagent in THF.
MS (ESP): 318 (M+1) for $C_{10}H_{13}BrN_4OS$ Intermediate 46

5-Bromo-2-(3-ethylureido)isonicotinamide

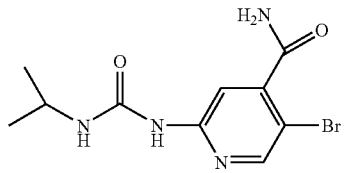

The compound was synthesized by a method analogous to the synthesis of Intermediate 43 starting with methyl 2-amino-5-bromoisonicotinate and 2-isocyanatopropane and ammonia solution (7N, MeOH). MS (ESP): 303 (M+1) for $C_{10}H_{13}BrN_4O_2$ Intermediate 47

N-{5-Bromo-4-[4-(trifluoromethyl)-1,3-thiazol-2-yl]pyridin-2-yl}-N'-(sec-butyl)urea

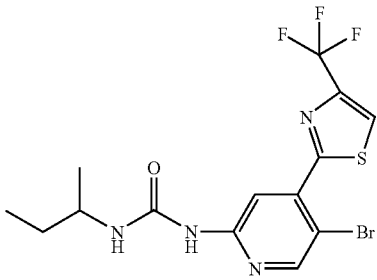

The above compound was synthesized by a method analogous to the synthesis of Intermediate 31 starting with Intermediate 48 and treating it with TFAA and TEA. MS (ESP): 424 (M+1) for $C_{14}H_{14}BrF_3N_4OS$ Intermediate 48

1-(5-Bromo-4-(4-hydroxy-4-(trifluoromethyl)-4,5-dihydrothiazol-2-yl)pyridin-2-yl)-3-sec-butylurea

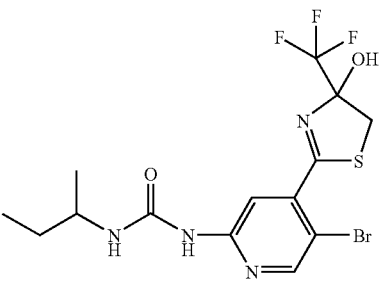

The title compound was synthesized by a method analogous to the synthesis of Intermediate 39 starting with Intermediate 49 and 3-bromo-1,1,1-trifluoropropan-2-one in acetonitrile.
MS (ESP): 442 (M+1) for $C_{14}H_{16}BrN_4O_2S$ Intermediate 49

5-Bromo-2-(3-sec-butylureido)pyridine-4-carbothioamide

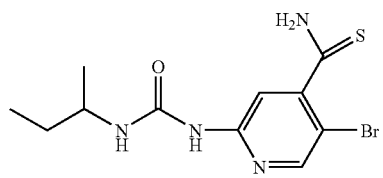

The title compound was synthesized by a method analogous to the synthesis of Intermediate 42 starting with Intermediate 50 and Lawessons reagent in THF. MS (ESP): 332 (M+1) for $C_{11}H_{15}BrN_4OS$ Intermediate 50

5-Bromo-2-(3-sec-butylureido)isonicotinamide

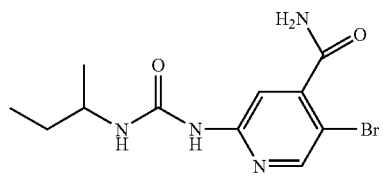

The compound was synthesized by a method analogous to the synthesis of Intermediate 43 starting with methyl 2-amino-5-bromoisonicotinate, 2-isocyanatobutane and ammonia solution (7N, MeOH). MS (ESP): 303 (M+1) for $C_{10}H_{13}BrN_4O_2$ Intermediate 51

1-Ethyl-3-(5-(4,4,5,5-tetramethyl-1,3,2-dioxaborolan-2-yl)-4-(4-(trifluoromethyl)thiazol-2-yl)pyridin-2-yl)urea

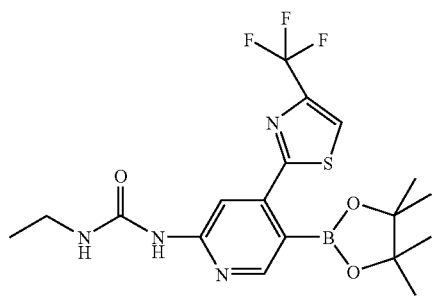

1-(5-bromo-4-(4-(trifluoromethyl)thiazol-2-yl)pyridin-2-yl)-3-ethylurea (200 mg, 0.51 mmol), 4,4,4',4',5,5,5',5'-octamethyl-2,2'-bi(1,3,2-dioxaborolane) (386 mg, 1.52 mmol), potassium acetate (149 mg, 1.52 mmol), and 1,1'-Bis(diphenylphosphino)ferrocene-palladium dichloride (20.72 mg, 0.03 mmol) were mixed in a microwave vial and degassed with argon. DMSO (4 mL) was added and the solution was heated at 90° C. for 5 hour (oil bath). The reaction was partitioned between water and ethyl acetate. The layers were separated, and the organic layer was back extracted three times with ethyl acetate. The organic layer was combined with the extracts, then washed with water and brine, dried over magnesium sulfate and concentrated to give a light brown solid that was a mixture of the title compound (35%), {6-{[(ethylamino)carbonyl]amino}-4-[4-(trifluoromethyl)-1,3-thiazol-2-yl]pyridin-3-yl}boronic acid (25%) and N-ethyl-N'-{4-[4-(trifluoromethyl)-1,3-thiazol-2-yl]pyridin-2-yl}urea (25%) which was used without further purification. MS (ESP): 443 (M+1) for $C_{18}H_{22}BF_3N_4O_3S$ Intermediate 52

N-Ethyl-N'-[4-phenyl-5-(4,4,5,5-tetramethyl-1,3,2-dioxaborolan-2-yl)pyridin-2-yl]urea

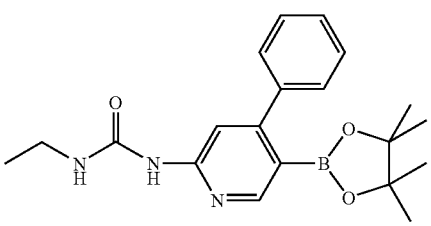

The compound was synthesized by a method analogous to the synthesis of Intermediate 51 starting with Intermediate 35. The product obtained was a mixture that was used without further purification. MS (ESP): 368 (M+1) for $C_{20}H_{26}BN_3O_3$ Intermediate 54

Methyl 2-chloro-4-[1-(2-methoxyethyl)-1H-imidazol-2-yl]-1,3-thiazole-5-carboxylate

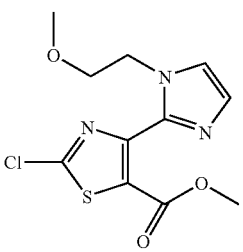

Methyl 2-amino-4-[1-(2-methoxyethyl)-1H-imidazol-2-yl]-1,3-thiazole-5-carboxylate (Intermediate 55; 0.55 g, 2.2 mmol) was suspended in glacial acetic acid (20 ml) and concentrated HCl (30 ml). The solution was cooled to 0° C. and a solution of sodium nitrite in water (15 ml) was added dropwise. After stirring at 0° C. for 10 min, the reaction was slowly warmed to room temperature and stirred for 1 hour. The reaction was followed by LCMS and once complete, a solution of urea (0.25 g) in water (10 ml) was added dropwise. After stirring at room temperature for 30 min, solvent was removed under reduced pressure. The residue was partitioned with sat. NaHCO$_3$ (aq) and EtOAc. Extraction with EtOAc (×3), drying with MgSO$_4$ and concentrating yielded an orange oil which was used without purification (0.20 g). MS (ES) (M+H)$^+$: 302 for $C_{11}H_{12}ClN_3O_3S$; NMR: 3.34 (s, 3H), 3.62 (m, 2H), 3.81 (s, 3H), 4.22 (m, 2H), 7.24 (s, 2H).

Intermediate 55

Methyl 2-amino-4-[1-(2-methoxyethyl)-1H-imidazol-2-yl]-1,3-thiazole-5-carboxylate

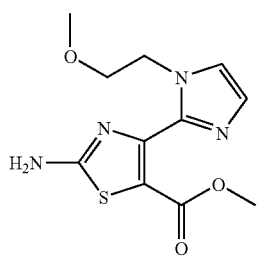

N-Iodosuccinimide (9.3 g, 41 mmol) was added to a mixture of 7.52 g (41 mmol) methyl 3-[1-(2-methoxyethyl)-1H-imidazol-2-yl]-3-oxopropanoate (Intermediate 56) and 7.5 g Amberlyst-15 resin in 400 ml EtOAc followed by stirring for 1 hour at room temperature. The resin was filtered off and rinsed with EtOAc. Solvent was removed from the filtrate and the residue was taken up in diethyl ether. Insoluble material was filtered off and rinsed with additional ether. Solvent was removed from the filtrate and the residue was dissolved in 200 ml MeOH before added 4.7 g (62 mmol) thiourea. The mixture was heated at reflux for 1 hour. Then the solvent was removed and the residue was taken up in aqueous $Na_2CO_3$. Insoluble material was collected by filtration and rinsed well with water. The solids were dried in vacuo affording 4.51 g of the title compound: MS (ES) (M+H)$^+$: 283 for $C_{11}H_{14}N_4O_3S$; NMR: 3.22 (s, 3H), 3.61 (m, 2H), 3.69 (s, 3H), 4.32 (m, 2H), 7.91 (s, 2H), 8.41 (s, 2H).

Intermediate 56

Methyl 3-[1-(2-methoxyethyl)-1H-imidazol-2-yl]-3-oxopropanoate

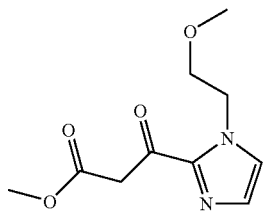

NaH (7.84 g, 196 mmol of a 60% dispersion in oil) was added portionwise to a solution of 6.18 g (Intermediate 57, 34.5 mmol) of 1-[1-(2-methoxyethyl)-1H-imidazol-2-yl]ethanone in 100 ml dimethylcarbonate. The mixture was heated to 90° C. for 2 hour forming a thick slurry. After cooling to room temperature, the mixture was slowly transferred to 1N HCl over ice. The mixture was brought to about pH 7 with $NaHCO_3$, then saturated with NaCl and extracted 4 times with EtOAc. The EtOAc was dried over $MgSO_4$, then concentrated to give an oil that was chromatographed on silica gel (100% DCM followed by gradient elution to 50% EtOAc in DCM) to yield the title compound. MS (ES) (M+H)$^+$: 227 for $C_{10}H_{14}N_2O_4$; NMR: 3.18 (s, 3H), 3.61 (m, 5H), 4.07 (s, 2H), 4.52 (m, 2H), 7.24 (s, 1H), 7.61 (s, 1H).

Intermediate 57

1-[1-(2-Methoxyethyl)-1H-imidazol-2-yl]ethanone

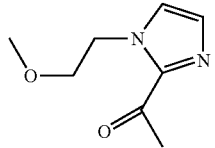

A solution of 30 ml (75 mmol) of 2.5 M n-butyllithium in hexanes was added slowly to a solution of 8.48 g (61.3 mmol) 1-(2-methoxyethyl)-1H-imidazole (WO 2003055876 A1) in 200 ml THF cooled in a dry ice-acetone bath. After stirring 1 h, 8 ml (75 mmol) of N-methoxy-N-methylacetamide was added quickly, and the solution was allowed to warm to room temperature over 30 min. After quenching with aqueous $NH_4Cl$, the mixture was diluted with water and extracted twice with EtOAc. The combined EtOAc layers were which washed with brine, dried over anhydrous $MgSO_4$, and concentrated to give an oil that was chromatographed on silica gel (100% DCM followed by gradient elution to 50% EtOAc in DCM). The title compound (8.5 g) was obtained as a mobile oil. MS (ES) (M+H)$^+$: 169 for $C_8H_{12}CN_2O_2$; NMR: 2.69 (s, 3H), 3.34 (s, 3H), 3.71 (m, 2H), 4.61 (m, 2H), 7.12 (s, 1H), 7.26 (s, 1H).

Intermediate 58

The following compound was synthesized according to the procedure described for Intermediate 54.

| Int | Compound | Data | SM |
|---|---|---|---|
| 58 | Methyl 2-chloro-4-(1-methyl-1H-1,2,4-triazol-5-yl)-1,3-thiazole-5-carboxylate | MS (ES) (M + H)$^+$: 259 for $C_8H_7ClN_4O_2S$ NMR: 3.92 (s, 6H), 8.04 (s, 1H). | Intermediate 59 |

Intermediate 59

The following Intermediate was synthesized as described for Intermediate 55.

| Int | Compound | Data | SM |
|---|---|---|---|
| 59 | Methyl 2-amino-4-(1-methyl-1H-1,2,4-triazol-5-yl)-1,3-thiazole-5-carboxylate | MS (ES) (M + H)$^+$: 240 for $C_8H_9N_5O_2S$ NMR: 3.61 (s, 3H), 3.71 (s, 3H), 7.96 (s, 1H), 8.10 (s, 2H). | Intermediate 60 |

Intermediate 60

Methyl 3-(1-methyl-1H-1,2,4-triazol-5-yl)-3-oxopropanoate

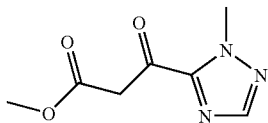

NaH (7.84 g, 196 mmol of a 60% dispersion in oil) was added portionwise to a solution of 6.18 g (34.5 mmol) of 1-(1-methyl-1H-1,2,4-triazol-5-yl)ethanone (Ohta, S.; Kawasaki, I.; Fukuno, A.; Yamashita, M.; Tada, T.; Kawabata, T. *Chem. Pharm. Bull*. (1993), 41(7), 1226-31) in 100 ml dimethylcarbonate. The mixture was heated to 90° C. for 2 hour forming a thick slurry. After cooling to room temperature, the mixture was slowly transferred to 1N HCl over ice. The mixture was brought to about pH 7 with NaHCO$_3$, then saturated with NaCl and extracted 4 times with EtOAc. The combined EtOAc layers were dried over anhydrous MgSO$_4$, then concentrated to give an oil that was chromatographed on silica gel (100% DCM followed by gradient elution to 50% EtOAc in DCM). The title compound (5.3 g) was obtained as an oil. NMR: 3.78 (s, 3H), 4.11 (s, 2H), 4.22 (s, 3H), 7.94 (s, 1H).

Intermediate 60

The following compound was synthesized according to the procedure described for Intermediate 54.

| Int | Compound | Data | SM |
|---|---|---|---|
| 61 | Methyl 2-chloro-4-(1-methyl-1H-imidazol-2-yl)-1,3-thiazole-5-carboxylate | MS (ES) (M + H)$^+$: 258 for C$_9$H$_8$ClN$_3$O$_2$S NMR: 3.73 (s, 3H), 3.81 (s, 3H), 7.03 (s, 1H), 7.21 (s, 1H). | Intermediate 62 |

Intermediate 62

Methyl 2-amino-4-(1-methyl-1H-imidazol-2-yl)-1,3-thiazole-5-carboxylate

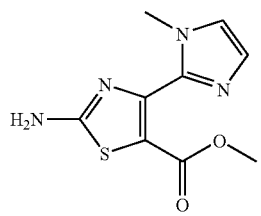

N-Iodosuccinimide (9.3 g, 41 mmol) was added to a mixture of 7.52 g (41 mmol) methyl 3-(1-methyl-1H-imidazol-2-yl)-3-oxopropanoate (Intermediate 63) and 7.5 g Amberlyst-15 resin in 400 ml EtOAc followed by stirring for 1 hour at room temperature. The resin was filtered off and rinsed with EtOAc. Solvent was removed from the filtrate and the residue was taken up in diethyl ether. Insoluble material was filtered off and rinsed with additional ether. Solvent was removed from the filtrate and the residue was dissolved in 200 ml MeOH before addition of 4.7 g (62 mmol) thiourea. The mixture was heated at reflux for 1 hour, then the solvent was removed and the residue was taken up in aqueous Na$_2$CO$_3$. Insoluble material was collected by filtration and rinsed well with water. The solids were dried in vacuo affording 4.51 g of the title compound: MS (ES) (M+H)$^+$: 239 for C$_9$H$_{10}$N$_4$O$_2$S; NMR: 3.48 (s, 3H), 3.57 (s, 3H), 6.90 (s, 1H), 7.12 (s, 1H), 7.98 (s, 2H).

Intermediate 63

The following compound was synthesized according to the procedure described for Intermediate 54.

| Int | Compound | Data | SM |
|---|---|---|---|
| 63 | Methyl 3-(1-methyl-1H-imidazol-2-yl)-3-oxopropanoate | MS (ES) (M + H)$^+$: 183 for C$_8$H$_{10}$N$_2$O$_3$. | 1-(1-Methyl-1H-imidazol-2-yl)ethanone (Abarca-Gonzalez, B.; Jones, R. A.; Medio-Simon, M.; Quilez-Pardo, J.; Sepulveda-Arques, J.; Zaballos-Garcia, E., Synth. Comm. (1990), 20(3), 321-31). |

Intermediate 64

Ethyl 4-[(tert-butylamino)carbonyl]-2-chloro-1,3-thiazole-5-carboxylate

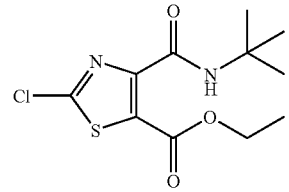

The title compound was synthesized by a method analogous to the synthesis of Intermediate 4 starting with Intermediate 6 and n-butylamine. MS (ESP): 291 (M+1) for C11H15ClN$_2$O$_3$S; NMR (CDCl$_3$: 1.36 (t, 3H); 4.38 (q, 2H); 7.48 (s, 1H).

Intermediate 65

6-Chloro-pyridine-3,4-dicarboxylic acid 3-dimethylamide 4-isopropylamide

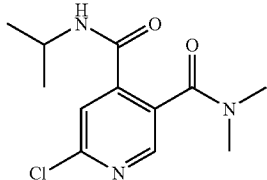

To a stirred a solution of 2-chloro-5-dimethylcarbamoyl-isonicotinic acid (Intermediate 66, 0.15 g, 0.65 mmoles) in dry tetrahydrofuran (5 mL) was added HOBT (0.2 g, 1.31 mM), N-methyl morpholine (0.216 mL, 1.97 mmoles), isopropyl amine (0.0556 mL, 0.65 mmoles) and EDC (0.25 g, 1.31 mmoles), and the mixture was stirred over night at room temperature. After completion of the reaction, the reaction mixture was diluted with ethyl acetate (10 mL) and washed with water (10 mL), and the layers were separated. The organic layer was washed with 2N hydrochloric acid (1×10 mL), sodium bicarbonate solution (2×20 mL), and brine (1×10 mL) respectively, then dried over MgSO$_4$, then concentrated to afford 0.15 g (82.2%) of the title compound. MS (APCI): 270 (M+H$^+$) for C$_{12}$H$_{16}$ClN$_3$O$_2$; NMR: 1.22 (d, 6H), δ 2.8 (s, 3H), δ 3.1 (s, 3H), δ 4.19 (m, 1H), δ 7.66 (s, 1H), δ 8.3 (s, 1H).

Intermediate 66

2-Chloro-5-dimethylcarbamoyl-isonicotinic acid

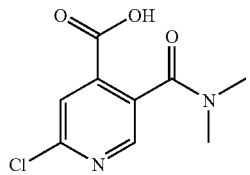

Formic acid (0.628 mL, 16.5 mmoles) and 30% hydrogen per oxide (1.87 mL, 16.5 mmoles) were added to 6-chloro-4-formyl-N,N-dimethyl-nicotinamide (Intermediate 67, 0.7 g. 3.3 mmoles), and the solution was kept at 4° C. for 4 days. The precipitate was filtered and washed with cold water. The solid was heated to reflux in toluene then collected by filtration (2×25 mL) to afford 0.28 g (35.89%) of the title compound as pale yellow solid. MS (APCI): 229 (M+H$^+$) for C$_9$H$_9$ClN$_2$O$_3$; NMR: 2.76 (s, 3H), δ 2.97 (s, 3H), δ 7.84 (s, 1H), δ 8.47 (s, 1H).

Intermediate 67

6-Chloro-4-formyl-N,N-dimethyl-nicotinamide

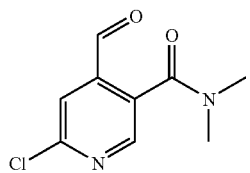

To 6-chloro-4-formyl-nicotinic acid (Intermediate 68, 4.0 g 21.5 mM) was added thionyl chloride (20 mL), and the solution was refluxed for 1½ h at 80° C. The reaction mixture was concentrated to dryness. Chloroform (50 mL) was added and then washed with sodium bicarbonate solution (2×50 mL). Organic layer was dried and concentrated. To the residue dry dichloro methane (30 mL) was added and to this 2,6-lutidine (2.67 mL, 21.5 mM) and 2M solution of N,N dimethyl amine was added and refluxed for 2 h. After completion of the reaction, the reaction mixture was diluted with dichloro methane (20 mL), water (50 mL) was added and the layers were separated. The organic layer was washed with 2N hydrochloric acid (1×50 mL), bicarbonate solution (1×50 mL) and dried, concentrated to afford 4.1 g (89.7%) of the title compound as thick brown syrup. NMR (CDCl$_3$); δ 2.92 (s, 3H), δ 3.19 (s, 3H) δ 7.78 (s, 1H), δ 8.51 (s, 1H), δ 10.07 (s, 1H).

Intermediate 68

6-Chloro-4-formyl-nicotinic acid

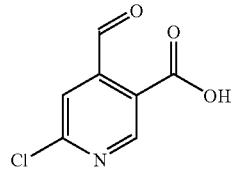

To a stirred solution of tetramethylpiperidine (6.89 mL, 40.8 mM) in dry tetrahydrofuran (20 mL), n-butyl lithium (36.5 mL, 1.12 mL, 40.8 mM) was added drop wise at −78° C. for 15 min. The reaction mixture was stirred at −78° C. for 30 min and at −50° C. for 30 min. 6-Chloro nicotinic acid (1.6 g, 10.2 mM) dissolved in dry tetrahydrofuran (10 mL) was added dropwise to the above reaction mixture for 15 min at −78° C. The reaction mixture was stirred at −78° C. for 30 min and at −50° C. for 30 min. Dry dimethyl formamide (5 mL) was added dropwise at −78° C. for 5 min. The reaction mixture was stirred at −78° C. for 30 min and at −50° C. for 30 min. After the completion of the reaction, reaction mixture was quenched with 2N hydrochloric (30 mL) extracted with ethyl acetate (2×150 mL). Organic layer dried over anhydrous MgSO4, then concentrated. The concentrate was subjected to column chromatography, and the product was eluted with 15% ethyl acetate in petroleum ether to get 1.01 g (53.19%) of the title compound. MS (APCI): 186 (M+H$^+$) for C$_7$H$_4$ClNO$_3$; NMR CD$_3$OD): δ 6.18 (s, 1H), δ 7.75 (s, 1H), δ 8.74 (s, 1H).

Intermediate 69

N-[5-bromo-4-(4-phenyl-1,3-thiazol-2-yl)pyridin-2-yl]-N'-ethylurea

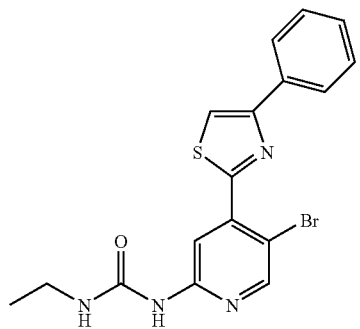

To a mixture of 5-bromo-2-(3-ethylureido)pyridine-4-carbothioamide (Intermediate 42, 0.146 g, 0.48 mmol) in acetonitrile (3 mL), 2-bromo-1-phenylethanone (0.105 g, 0.53 mmol) was added and the reaction mixture was heated to 80° for 16 h. The reaction mixture was cooled to room temperature and concentrated under reduced pressure. The resulting solids were filtered and washed with acetonitrile to yield 164 mg of the title compound as an off-white solid.

LC/MS (ES$^+$)[(M+H)$^+$]: 403, 405 for C$_{17}$H$_{15}$BrN$_4$OS. $^1$H NMR (300 MHz, d$_6$-DMSO): 1.08 (t, 3H), 3.04-3.28 (m, 2H), 7.36 (m, 1H), 7.45 (m, 1H), 7.50 (t, 2H), 8.02-8.10 (m, 2H), 8.47 (s, 1H), 8.50 (s, 1H), 8.53 (s, 1H), 9.39 (s, 1H).

The invention claimed is:
1. A compound of formula (I):

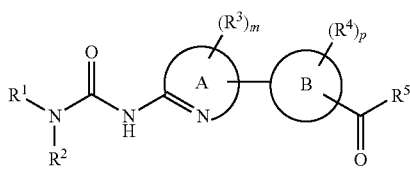

wherein:
R$^1$ is selected from C$_{1-6}$alkyl; wherein R$^1$ may be optionally substituted on carbon by one or more C$_{1-6}$alkyl;
R$^2$ is hydrogen;
each R$^4$ is a substituent on carbon which is independently selected from halo, nitro, cyano, hydroxy, amino, carboxy, carbamoyl, mercapto, sulphamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$alkyl)carbamoyl, N,N—(C$_{1-6}$alkyl)$_2$carbamoyl, N—(C$_{1-6}$alkoxy)carbamoyl, N,N—(C$_{1-6}$alkoxy)$_2$carbamoyl, C$_{1-6}$alkylS(O)$_a$ wherein a is 0 to 2, C$_{1-6}$alkoxycarbonyl, C$_{1-6}$alkoxycarbonylamino, N—(C$_{1-6}$alkyl)sulphamoyl, N,N—(C$_{1-6}$alkyl)$_2$sulphamoyl, C$_{1-6}$alkylsulphonylamino, carbocyclyl-R$^9$— or heterocyclyl-R$^{10}$—; wherein each R$^4$ may be optionally substituted on carbon by one or more independently selected R$^{11}$; and wherein if said heterocyclyl contains an —NH— moiety that nitrogen may be optionally substituted by a group selected from R$^{12}$;
m is 0, and R$^3$ is absent;
p is 0, 1, or 2; wherein the values of R$^4$ may be the same or different;
Ring A is pyridyl; wherein the nitrogen of the pyridyl is ortho to the R$^1$R$^2$NC(O)NH group of formula (I);
Ring B is selected from the group consisting of thiazolyl, pyridyl, 1,3-benzothiazolyl, phenyl, imidazo[1,2-a]pyridinyl, 4-oxo-1H-quinolinyl, and 2-oxo-1H-pyridyl;
R$^5$ is selected from hydroxy, C$_{1-6}$alkoxy, —N(R$^{15}$)(R$^{16}$) and a nitrogen linked heterocyclyl;
wherein said C$_{1-6}$alkoxy may be optionally substituted on carbon by one or more R$^{17}$; and wherein if said nitrogen linked heterocyclyl contains an —NH— moiety that nitrogen may be optionally substituted by a group selected from R$^{18}$;
R$^{11}$ and R$^{17}$ are substituents on carbon and are each independently selected from halo, nitro, cyano, hydroxy, amino, carboxy, carbamoyl, mercapto, sulphamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$alkyl)carbamoyl, N,N—(C$_{1-6}$alkyl)$_2$carbamoyl, C$_{1-6}$alkylS(O)$_a$ wherein a is 0 to 2, C$_{1-6}$alkoxycarbonyl, C$_{1-6}$alkoxycarbonylamino, N—(C$_{1-6}$alkyl)sulphamoyl, N,N—(C$_{1-6}$alkyl)$_2$sulphamoyl, C$_{1-6}$alkylsulphonylamino, carbocyclyl or heterocyclyl; wherein R$^{11}$ and R$^{17}$ independently of each other may be optionally substituted on carbon by one or more R$^{19}$; and wherein if said heterocyclyl contains an —NH— moiety that nitrogen may be optionally substituted by a group selected from R$^{20}$;
R$^{15}$ and R$^{16}$ are independently selected from hydrogen, C$_{1-6}$alkyl, C$_{1-6}$alkoxy, C$_{1-6}$alkanoyl, carbocyclyl or heterocyclyl; wherein R$^{15}$ and R$^{16}$ independently of each other may be optionally substituted on carbon by one or more R$^{21}$; and wherein if said heterocyclyl contains an —NH— moiety that nitrogen may be optionally substituted by a group selected from R$^{22}$;
R$^{12}$, R$^{18}$, R$^{20}$ and R$^{22}$ are independently selected from C$_{1-6}$alkyl, C$_{3-6}$cycloalkyl, C$_{1-6}$alkanoyl, C$_{1-6}$alkylsulphonyl, C$_{1-6}$alkoxycarbonyl, carbamoyl, N—(C$_{1-6}$alkyl)carbamoyl, N,N—(C$_{1-6}$alkyl)carbamoyl, benzyl, benzyloxycarbonyl, benzoyl and phenylsulphonyl; wherein R$^{12}$, R$^{18}$, R$^{20}$ and R$^{22}$ independently of each other may be optionally substituted on carbon by one or more R$^{23}$;
R$^9$ and R$^{10}$ are independent selected from a direct bond, —O—, —N(R$^{24}$)—, —C(O)—, —N(R$^{25}$)C(O)—, —C(O)N(R$^{26}$)—, —S(O)$_s$—, —SO$_2$N(R$^{27}$)— or —N(R$^{28}$)SO$_2$—; wherein R$^{24}$, R$^{25}$, R$^{26}$, R$^{27}$ and R$^{28}$ are independently selected from hydrogen or C$_{1-6}$alkyl and s is 0-2; and
R$^{19}$, R$^{21}$ and R$^{23}$ are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;
or a pharmaceutically acceptable salt thereof.
2. A compound of formula (I):

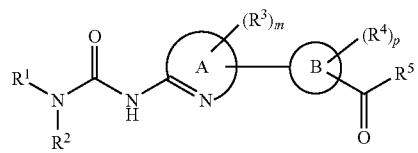

wherein:
R$^1$ is selected from C$_{1-6}$alkyl; wherein R$^1$ may be optionally substituted on carbon by one or more C$_{1-6}$alkyl;
R$^2$ is hydrogen;
R$^3$ is selected from the group consisting of pyridyl, phenyl, and thiazolyl, wherein the pyridyl, phenyl or thiazolyl may be optionally substituted on one or more carbon atoms with one or more R$^{11}$;
each R$^4$ is a substituent on carbon which is each independently selected from halo, nitro, cyano, hydroxy, amino, carboxy, carbamoyl, mercapto, sulphamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$alkyl)carbamoyl, N,N—(C$_{1-6}$alkyl)$_2$carbamoyl, N—(C$_{1-6}$alkoxy)carbamoyl, N,N—(C$_{1-6}$alkoxy)$_2$carbamoyl, C$_{1-6}$alkylS(O)$_a$ wherein a is 0 to 2, C$_{1-6}$alkoxycarbonyl, C$_{1-6}$alkoxycarbonylamino, N—(C$_{1-6}$alkyl)sulphamoyl, N,N—(C$_{1-6}$alkyl)$_2$sulphamoyl, C$_{1-6}$alkylsulphonylamino, carbocyclyl-R$^9$— or heterocyclyl-R$^{10}$—; wherein each R$^4$ may be optionally substituted on carbon by one or more independently selected R$^{11}$; and wherein if said heterocyclyl contains an —NH— moiety that nitrogen may be optionally substituted by a group selected from R$^{12}$;
m is 1;

p is 0, 1, or 2; wherein the values of $R^4$ may be the same or different;

Ring A is pyridyl; wherein the nitrogen of the pyridyl is ortho to the $R^1R^2NC(O)NH$ group of formula (I);

Ring B is selected from the group consisting of thiazolyl, pyridyl, 1,3-benzothiazolyl, phenyl, imidazo[1,2-a]pyridinyl, 4-oxo-1H-quinolinyl, and 2-oxo-1H-pyridyl;

$R^5$ is selected from hydroxy, $C_{1-6}$alkoxy, —$N(R^{15})(R^{16})$ and a nitrogen linked heterocyclyl; wherein said $C_{1-6}$alkoxy may be optionally substituted on carbon by one or more $R^{17}$; and wherein if said nitrogen linked heterocyclyl contains an —NH— moiety that nitrogen may be optionally substituted by a group selected from $R^{18}$;

$R^{11}$ and $R^{17}$ are substituents on carbon and are each independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^{11}$ and $R^{17}$ independently of each other may be optionally substituted on carbon by one or more $R^{19}$; and wherein if said heterocyclyl contains an —NH— moiety that nitrogen may be optionally substituted by a group selected from $R^{20}$;

$R^{15}$ and $R^{16}$ are independently selected from hydrogen, $C_{1-6}$alkyl, $C_{1-6}$alkoxy, $C_{1-6}$alkanoyl, carbocyclyl or heterocyclyl; wherein $R^{15}$ and $R^{16}$ independently of each other may be optionally substituted on carbon by one or more $R^{21}$; and wherein if said heterocyclyl contains an —NH— moiety that nitrogen may be optionally substituted by a group selected from $R^{22}$;

$R^{12}$, $R^{18}$, $R^{20}$ and $R^{22}$ are independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^{12}$, $R^{18}$, $R^{20}$ and $R^{22}$ independently of each other may be optionally substituted on carbon by one or more $R^{23}$;

$R^9$ and $R^{10}$ are independent selected from a direct bond, —O—, —N($R^{24}$)—, —C(O)—, —N($R^{25}$)C(O)—, —C(O)N($R^{26}$)—, —S(O)$_s$—, —SO$_2$N($R^{27}$)— or —N($R^{28}$)SO$_2$—; wherein $R^{24}$, $R^{25}$, $R^{26}$, $R^{27}$ and are independently selected from hydrogen or $C_{1-6}$alkyl and s is 0-2; and $R^{19}$, $R^{21}$ and $R^{23}$ are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof.

3. A compound according to claim 2, wherein $R^{11}$, for each occurrence, when substituted on $R^3$ is independently selected from the group consisting of a halo, a $C_{1-4}$alkyl, and a $C_{1-4}$haloalkyl.

4. A compound according to claim 2, wherein p is 0.

5. A compound according to claim 2, wherein:
p is 1; and
$R^4$ is selected from the group consisting of carbamoyl, an N—($C_{1-6}$alkyl)carbamoyl, an N,N—($C_{1-6}$alkyl)carbamoyl, a $C_{1-6}$alkoxycarbonyl, carboxy, oxo, hydroxy, a $C_{1-6}$alkyl, a $C_{1-6}$alkanoyl, a N—($C_{1-6}$alkoxy)carbamoyl, an imidazolyl, and a 1H-1,2,4-triazolyl, wherein the N—($C_{1-6}$alkyl)carbamoyl, N,N—($C_{1-6}$alkyl)carbamoyl, $C_{1-6}$alkoxycarbonyl, $C_{1-6}$alkyl, $C_{1-6}$alkanoyl, N—($C_{1-6}$alkoxy)carbamoyl, imidazolyl, and 1H-1,2,4-triazolyl may be optionally substituted on one or more carbon atoms with one or more $R^{11}$; and wherein the hydrogen of the NH— of the imidazoyly and 1H-1,2,4-triazolyl optionally may be replaced with $R^{12}$.

6. A compound according to claim 5, wherein $R^{11}$, for each occurrence, when substituted on $R^4$ is independently selected from the group consisting of a $C_{1-4}$alkyl, a $C_{1-4}$alkoxy, and a $C_{1-4}$alkoxyC$_{1-4}$alkyl; and $R^{12}$, for each occurrence is independently selected from the group consisting of $C_{1-4}$alkyl and a $C_{1-4}$alkoxyC$_{1-4}$alkyl.

7. A compound of formula (XVIII):

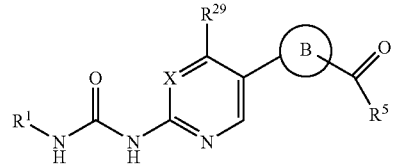

(XVIII)

or a pharmaceutically acceptable salt thereof, wherein:

$R^1$ is selected from $C_{1-6}$alkyl; wherein $R^1$ may be optionally substituted on carbon by one or more $C_{1-6}$alkyl;

$R^5$ is selected from hydroxy, $C_{1-6}$alkoxy, —$N(R^{15})(R^{16})$ and a nitrogen linked heterocyclyl; wherein said $C_{1-6}$alkoxy may be optionally substituted on carbon by one or more $R^{17}$; and wherein if said nitrogen linked heterocyclyl contains an —NH— moiety that nitrogen may be optionally substituted by a group selected from $R^{18}$;

Ring B is selected from the group consisting of thiazolyl, pyridyl, 1,3-benzothiazolyl, phenyl, imidazo[1,2-a]pyridinyl, 4-oxo-1H-quinolinyl, and 2-oxo-1H-pyridyl, which may be optionally substituted by a group selected from $R^{14}$;

X is CH; and $R^{29}$ is a 6-membered aryl or a 5- or 6-membered heteroaryl, wherein the aryl or heteroaryl is optionally substituted on one or more carbon atom with one or more $R^{11}$; and wherein if the heteroaryl comprises a NH— moiety the hydrogen may be optionally substituted with a group selected from $R^8$;

$R^{17}$ is a substituent on carbon and is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^{17}$ may be optionally substituted on carbon by one or more $R^{19}$; and wherein if said heterocyclyl contains an —NH— moiety that nitrogen may be optionally substituted by a group selected from $R^{20}$;

$R^8$ is independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein each $R^8$ independently of each other may be optionally substituted on carbon by one or more $R^{23}$;

$R^{14}$, $R^{18}$, $R^{20}$ and $R^{22}$ are independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^{14}$, $R^{18}$, $R^{20}$ and $R^{22}$ independently of each other may be optionally substituted on carbon by one or more $R^{23}$;

$R^{15}$ and $R^{16}$ are independently selected from hydrogen, $C_{1-6}$alkyl, $C_{1-6}$alkoxy, $C_{1-6}$alkanoyl, carbocyclyl or heterocyclyl; wherein $R^{15}$ and $R^{16}$ independently of each other may be optionally substituted on carbon by one or more $R^{21}$; and wherein if said heterocyclyl contains an —NH— moiety that nitrogen may be optionally substituted by a group selected from $R^{22}$; and $R^{19}$, $R^{21}$ and $R^{23}$ are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl.

8. A compound according to claim 7, wherein:

Ring B is selected from the group consisting of phenyl, pyridyl, and thiazolyl;

$R^5$ is hydroxy, amino, a $C_{1-4}$alkoxy, an N—($C_{1-4}$alkyl)amino, an N,N—($C_{1-4}$alkyl)amino, or an N—($C_{3-6}$cycloalkyl)amino, wherein the $C_{1-4}$alkoxy is optionally substituted on one or more carbon atoms with one or more $R^{17}$; and wherein N—($C_{1-4}$alkyl)amino, N,N—($C_{1-4}$alkyl)amino, or N—($C_{3-6}$cycloalkyl)amino may be optionally substituted on one or more carbon atoms with one or more $R^{21}$; and $R^{29}$ is selected from the group consisting of pyridyl, thiazolyl, and phenyl, wherein the pyridyl, thiazolyl or phenyl may be optionally substituted on one or more carbon atom with one or more $R^{11}$.

9. A compound according to claim 8, wherein said compound is a compound in accord with formula (XIX):

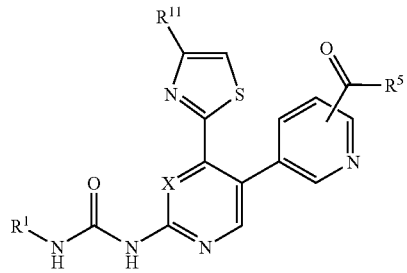

(XIX)

or a pharmaceutically acceptable salt thereof.

10. A compound according to claim 9, wherein $R^{11}$ is a halo, a $C_{1-4}$alkyl, or a $C_{1-4}$haloalkyl.

11. A compound according to claim 8, wherein said compound is a compound in accord with formula (XX):

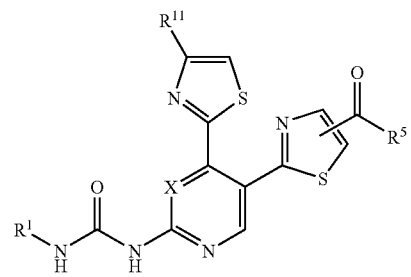

(XX)

or a pharmaceutically acceptable salt thereof.

12. A compound according to claim 11, wherein $R^{11}$ is a halo, a $C_{1-4}$alkyl, or a $C_{1-4}$haloalkyl.

13. A pharmaceutical composition comprising a compound of claim 2, or a pharmaceutically acceptable salt thereof, and a pharmaceutically acceptable excipient or carrier.

14. A compound according to claim 1, wherein p is 0.

15. A compound according to claim 1, wherein:

p is 1; and $R^4$ is selected from the group consisting of carbamoyl, an N—($C_{1-6}$alkyl)carbamoyl, an N,N—($C_{1-6}$alkyl)carbamoyl, a $C_{1-6}$alkoxycarbonyl, carboxy, oxo, hydroxy, a $C_{1-6}$alkyl, a $C_{1-6}$alkanoyl, a N—($C_{1-6}$alkoxy)carbamoyl, an imidazolyl, and a 1H-1,2,4-triazolyl, wherein the N—($C_{1-6}$alkyl)carbamoyl, N,N—($C_{1-6}$alkyl)carbamoyl, $C_{1-6}$alkoxycarbonyl, $C_{1-6}$alkyl, $C_{1-6}$alkanoyl, N—($C_{1-6}$alkoxy)carbamoyl, imidazolyl, and 1H-1,2,4-triazolyl may be optionally substituted on one or more carbon atoms with one or more $R^{11}$; and wherein the hydrogen of the NH— of the imidazoyly and 1H-1,2,4-triazolyl optionally may be replaced with $R^{12}$.

16. A compound according to claim 15, wherein $R^{11}$, for each occurrence, when substituted on $R^4$ is independently selected from the group consisting of a $C_{1-4}$alkyl, a $C_{1-4}$alkoxy, and a $C_{1-4}$alkoxy$C_{1-4}$alkyl; and $R^{12}$, for each occurrence is independently selected from the group consisting of $C_{1-4}$alkyl and a $C_{1-4}$alkoxy$C_{1-4}$alkyl.

17. A pharmaceutical composition comprising a compound of claim 1, or a pharmaceutically acceptable salt thereof, and a pharmaceutically acceptable excipient or carrier.

* * * * *